(12) United States Patent
Hibner et al.

(10) Patent No.: US 10,743,850 B2
(45) Date of Patent: Aug. 18, 2020

(54) SURGICAL INSTRUMENT WITH LOCKING ARTICULATION DRIVE WHEEL

(71) Applicant: Ethicon LLC, Guaynabo, PR (US)

(72) Inventors: John A. Hibner, Mason, OH (US); Barry C. Worrell, Centerville, OH (US); Gregory W. Johnson, Milford, OH (US); Benjamin D. Dickerson, Cincinanti, OH (US); Daniel J. Mumaw, Liberty Township, OH (US)

(73) Assignee: Ethicon LLC, Guaynabo, PR (US)

( * ) Notice: Subject to any disclaimer, the term of this patent is extended or adjusted under 35 U.S.C. 154(b) by 532 days.

(21) Appl. No.: 15/089,741

(22) Filed: Apr. 4, 2016

(65) Prior Publication Data

US 2017/0281219 A1 Oct. 5, 2017

(51) Int. Cl.
*A61B 17/00* (2006.01)
*A61B 17/29* (2006.01)
*A61B 17/32* (2006.01)

(52) U.S. Cl.
CPC .... *A61B 17/00234* (2013.01); *A61B 17/2909* (2013.01); *A61B 17/320092* (2013.01);
(Continued)

(58) Field of Classification Search
CPC ...... A61B 17/320092; A61B 17/00234; A61B 17/2909; A61B 2017/00327;
(Continued)

(56) References Cited

U.S. PATENT DOCUMENTS 5,322,055 A   6/1994  Davison et al.
5,823,066 A * 10/1998  Huitema .......... A61B 17/07207
                                                74/527
(Continued)

FOREIGN PATENT DOCUMENTS

EP    0 702 937 A1    3/1996
EP    0 736 285 A2   10/1996
(Continued)

OTHER PUBLICATIONS

U.S. Appl. No. 14/258,179, filed Apr. 22, 2014.
(Continued)

*Primary Examiner* — Jing Rui Ou
(74) *Attorney, Agent, or Firm* — Frost Brown Todd LLC

(57) ABSTRACT

A surgical instrument includes a shaft assembly and an articulation control assembly. The shaft assembly includes an articulation section that is configured to deflect a distal end portion from the longitudinal axis. The articulation control assembly includes an articulation control member and a transmission assembly. The articulation control member is rotatably mounted relative to the shaft assembly. The transmission assembly is operatively connected between the articulation control member and the articulation section of the shaft assembly. The transmission assembly is configured to transmit selective manipulation of the articulation control member to the articulation section and selectively actuate the articulation section. The articulation control assembly is configured to lock without selective manipulation of the articulation control member to thereby inhibit actuation of the articulation section and unlock with selective manipulation of the articulation control member to thereby actuate the articulation section.

10 Claims, 34 Drawing Sheets

(52) U.S. Cl.
CPC .............. *A61B 2017/00327* (2013.01); *A61B 2017/00424* (2013.01); *A61B 2017/2905* (2013.01); *A61B 2017/2913* (2013.01); *A61B 2017/2916* (2013.01); *A61B 2017/2923* (2013.01); *A61B 2017/2927* (2013.01); *A61B 2017/2929* (2013.01); *A61B 2017/2946* (2013.01); *A61B 2017/320094* (2017.08); *A61B 2017/320095* (2017.08)

(58) Field of Classification Search
CPC .. A61B 2017/00424; A61B 2017/2905; A61B 2017/2913; A61B 2017/2916; A61B 2017/2923; A61B 2017/2929; A61B 2017/2946

See application file for complete search history.

(56) References Cited

U.S. PATENT DOCUMENTS

| | | | |
|---|---|---|---|
| 5,873,873 A | 2/1999 | Smith et al. | |
| 5,873,886 A | 2/1999 | Larsen et al. | |
| 5,897,523 A | 4/1999 | Wright et al. | |
| 5,980,510 A | 11/1999 | Tsonton et al. | |
| 5,989,264 A | 11/1999 | Wright | |
| 6,063,098 A | 5/2000 | Houser et al. | |
| 6,090,120 A | 7/2000 | Wright et al. | |
| 6,325,811 B1 | 12/2001 | Messerly | |
| 6,454,782 B1 | 9/2002 | Schwemberger | |
| 6,589,200 B1 | 7/2003 | Schwemberger et al. | |
| 6,752,815 B2 | 6/2004 | Beaupre | |
| 6,773,444 B2 | 8/2004 | Messerly | |
| 6,783,524 B2 | 8/2004 | Anderson et al. | |
| 7,135,030 B2 | 11/2006 | Schwemberger et al. | |
| 7,621,930 B2 | 11/2009 | Houser | |
| 8,461,744 B2 | 6/2013 | Wiener et al. | |
| 8,573,463 B2 | 11/2013 | Scirica et al. | |
| 8,591,536 B2 | 11/2013 | Robertson | |
| 8,623,027 B2 | 1/2014 | Price et al. | |
| 8,663,220 B2 | 3/2014 | Wiener et al. | |
| 8,986,302 B2 | 3/2015 | Aldridge et al. | |
| 9,023,071 B2 | 5/2015 | Miller et al. | |
| 9,095,367 B2 | 8/2015 | Olson et al. | |
| 2005/0006434 A1* | 1/2005 | Wales | A61B 17/07207 227/180.1 |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2009/0101692 A1* | 4/2009 | Whitman | A61B 17/07207 227/175.1 |
| 2011/0290853 A1* | 12/2011 | Shelton, IV | A61B 17/07207 227/177.1 |
| 2012/0078247 A1 | 3/2012 | Worrell et al. | |
| 2012/0112687 A1 | 5/2012 | Houser et al. | |
| 2012/0116265 A1 | 5/2012 | Houser et al. | |
| 2013/0023868 A1* | 1/2013 | Worrell | A61B 17/07207 606/33 |
| 2013/0289592 A1 | 10/2013 | Stulen et al. | |
| 2014/0000411 A1* | 1/2014 | Shelton, IV | A61B 34/30 74/650 |
| 2014/0005701 A1 | 1/2014 | Olson et al. | |
| 2014/0005703 A1 | 1/2014 | Stulen et al. | |
| 2014/0243801 A1* | 8/2014 | Fanelli | A61B 17/07207 606/1 |
| 2015/0080924 A1 | 3/2015 | Stulen et al. | |
| 2015/0141981 A1 | 5/2015 | Price et al. | |
| 2015/0320437 A1* | 11/2015 | Worrell | A61B 18/1445 606/169 |

FOREIGN PATENT DOCUMENTS

| | | |
|---|---|---|
| EP | 0 807 409 A1 | 11/1997 |
| EP | 2 090 236 A2 | 8/2009 |

OTHER PUBLICATIONS

U.S. Appl. No. 14/688,458, filed Apr. 16, 2015.
U.S. Appl. No. 14/688,663, filed Apr. 16, 2015.
U.S. Appl. No. 61/410,603, filed Nov. 5, 2010.
International Search Report and Written Opinion dated Sep. 22, 2017 for Application No. PCT/US2017/025944, 18 pgs.

* cited by examiner

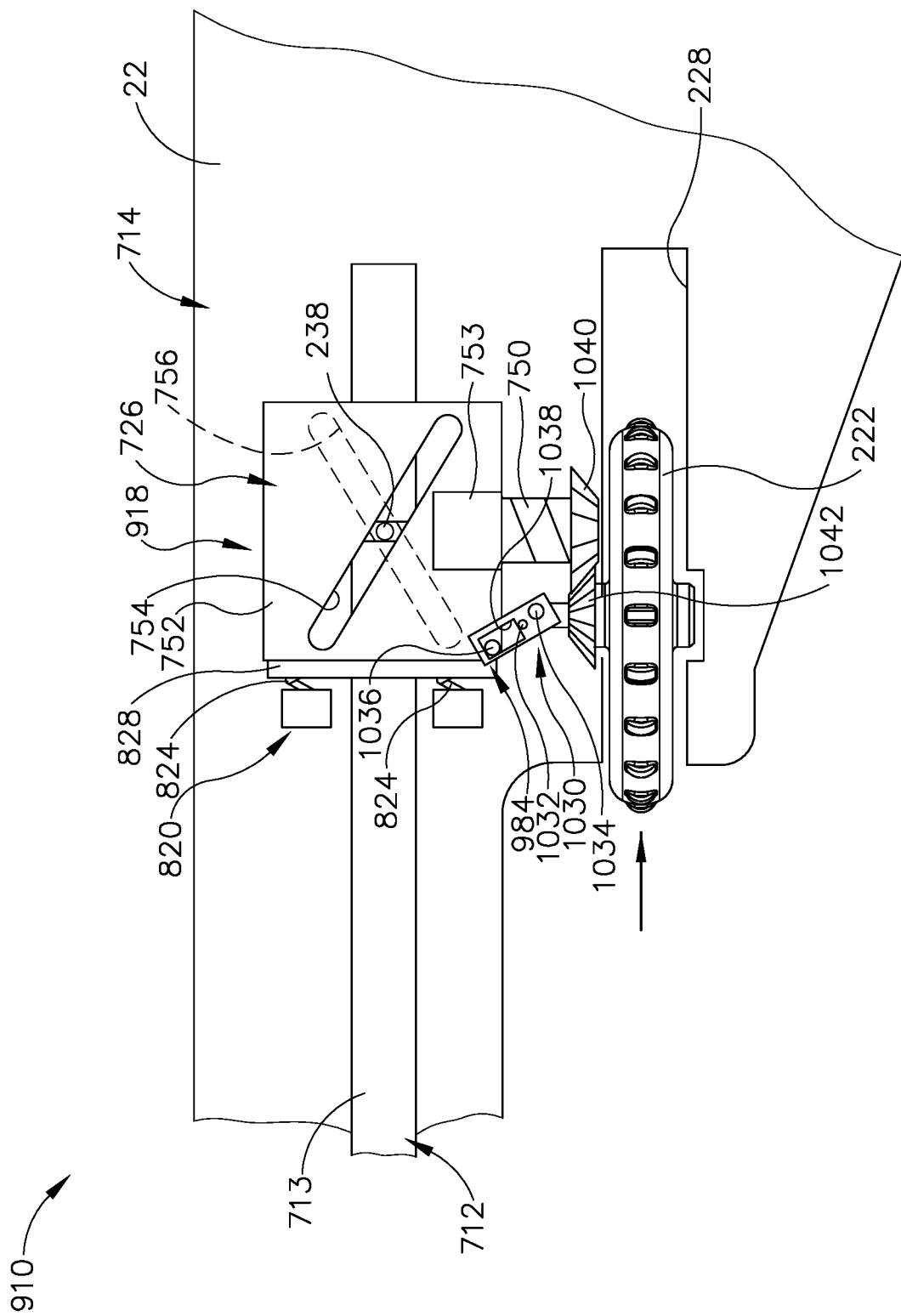

SURGICAL INSTRUMENT WITH LOCKING ARTICULATION DRIVE WHEEL

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; and U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section and/or a bendable ultrasonic waveguide. Examples of such ultrasonic surgical instruments are disclosed in U.S. Pat. No. 5,897,523, entitled "Articulating Ultrasonic Surgical Instrument," issued Apr. 27, 1999, the disclosure of which is incorporated by reference herein; U.S. Pat. No. 5,989,264, entitled "Ultrasonic Polyp Snare," issued Nov. 23, 1999, the disclosure of which is incorporated by reference herein; U.S. Pat. No. 6,063,098, entitled "Articulable Ultrasonic Surgical Apparatus," issued May 16, 2000, the disclosure of which is incorporated by reference herein; U.S. Pat. No. 6,090,120, entitled "Articulating Ultrasonic Surgical Instrument," issued Jul. 18, 2000, the disclosure of which is incorporated by reference herein; U.S. Pat. No. 6,454,782, entitled "Actuation Mechanism for Surgical Instruments," issued Sep. 24, 2002, the disclosure of which is incorporated by reference herein; U.S. Pat. No. 6,589,200, entitled "Articulating Ultrasonic Surgical Shears," issued Jul. 8, 2003, the disclosure of which is incorporated by reference herein; U.S. Pat. No. 6,752,815, entitled "Method and Waveguides for Changing the Direction of Longitudinal Vibrations," issued Jun. 22, 2004, the disclosure of which is incorporated by reference herein; U.S. Pat. No. 7,135,030, entitled "Articulating Ultrasonic Surgical Shears," issued Nov. 14, 2006; U.S. Pat. No. 7,621,930, entitled "Ultrasound Medical Instrument Having a Medical Ultrasonic Blade," issued Nov. 24, 2009, the disclosure of which is incorporated by reference herein; U.S. Pub. No. 2014/0005701, published Jan. 2, 2014, issued as U.S. Pat. No. 9,393,037 on Jul. 19, 2016, entitled "Surgical Instruments with Articulating Shafts," the disclosure of which is incorporated by reference herein; U.S. Pub. No. 2014/0005703, entitled "Surgical Instruments with Articulating Shafts," published Jan. 2, 2014, issued as U.S. Pat. No. 9,408,622 on Aug. 9, 2016, the disclosure of which is incorporated by reference herein; U.S. Pub. No. 2014/0114334, entitled "Flexible Harmonic Waveguides/Blades for Surgical Instruments," published Apr. 24, 2014, issued as U.S. Pat. No. 9,095,367 on Aug. 4, 2015, the disclosure of which is incorporated by reference herein; U.S. Pub. No. 2015/0080924, entitled "Articulation Features for Ultrasonic Surgical Instrument," published Mar. 19, 2015, issued as U.S. Pat. No. 10,172,636 on Jan. 8, 2019, the disclosure of which is incorporated by reference herein; and U.S. patent application Ser. No. 14/258,179, converted to U.S. Provisional App. No. 62/176,880, entitled "Ultrasonic Surgical Device with Articulating End Effector," filed Apr. 22, 2014, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 33B depicts the enlarged side sectional view of the surgical instrument of FIG. 33A, with the shaft control assembly in an unlocked articulation position;

Figure 1:
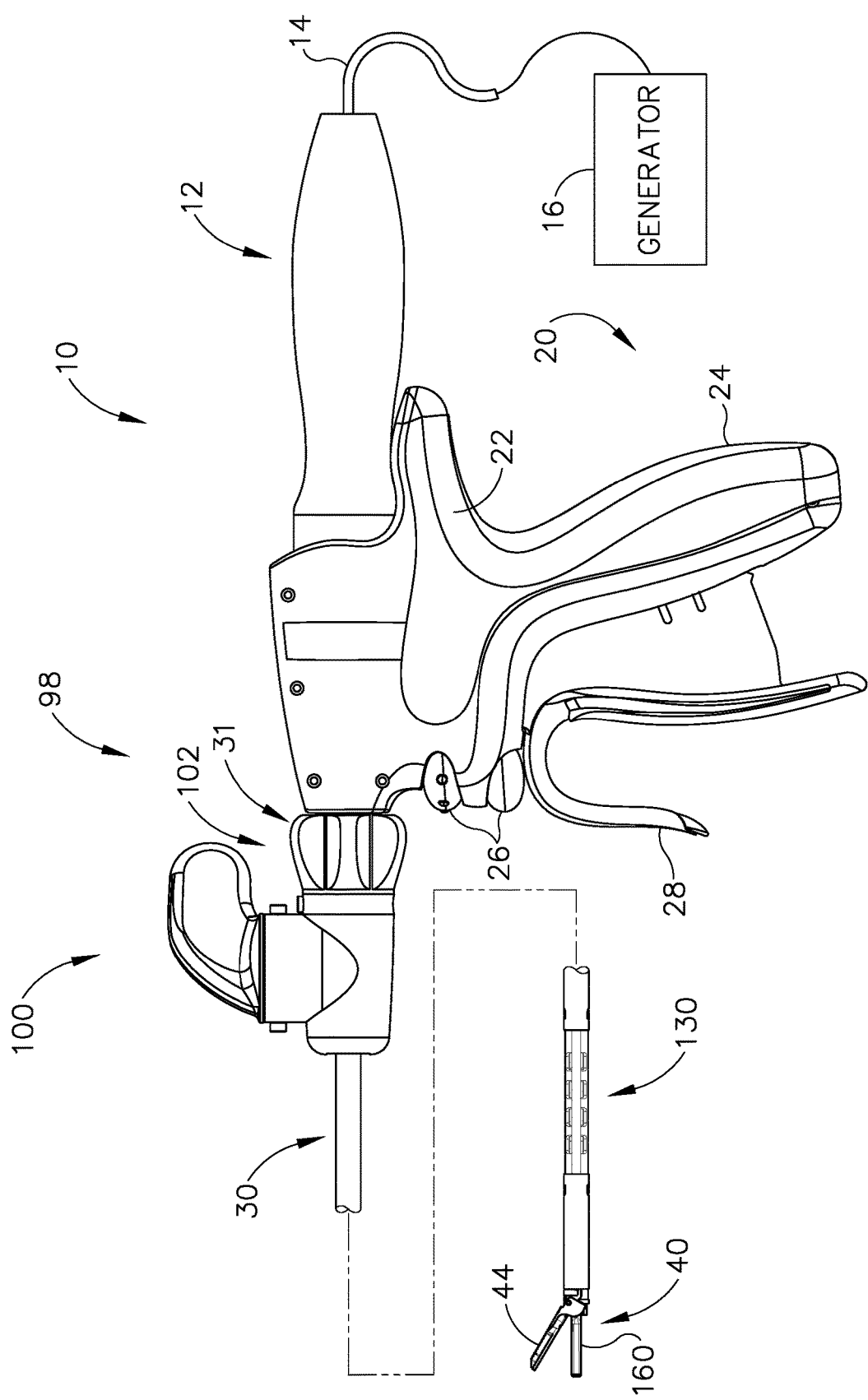
FIG. 1 depicts a side elevational view of a first exemplary ultrasonic surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal," "distal," "upper," and "lower" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. The terms "proximal," "distal," "upper," and "lower" are thus relative terms and not intended to unnecessarily limit the invention described herein.

I. EXEMPLARY ULTRASONIC SURGICAL INSTRUMENT

FIG. 1 shows an exemplary ultrasonic surgical instrument (10). At least part of instrument (10) may be constructed and operable in accordance with at least some of the teachings of any of the various patents, patent application publications, and patent applications that are cited herein. As described therein and as will be described in greater detail below, instrument (10) is operable to cut tissue and seal or weld tissue (e.g., a blood vessel, etc.) substantially simultaneously.

Instrument (10) of the present example comprises a handle assembly (20), a shaft assembly (30), and an end effector (40). Handle assembly (20) comprises a body (22) including a pistol grip (24) and a pair of buttons (26). Handle assembly (20) also includes a trigger (28) that is pivotable toward and away from pistol grip (24). It should be understood, however, that various other suitable configurations may be used, including but not limited to a scissor grip configuration. End effector (40) includes an ultrasonic blade (160) and a pivoting clamp arm (44). Clamp arm (44) is coupled with trigger (28) such that clamp arm (44) is pivotable toward ultrasonic blade (160) in response to pivoting of trigger (28) toward pistol grip (24); and such that clamp arm (44) is pivotable away from ultrasonic blade (160) in response to pivoting of trigger (28) away from pistol grip (24). Various suitable ways in which clamp arm (44) may be coupled with trigger (28) will be apparent to those of ordinary skill in the art in view of the teachings herein. In some versions, one or more resilient members are used to bias clamp arm (44) and/or trigger (28) to the open position shown in FIG. 1.

An ultrasonic transducer assembly (12) extends proximally from body (22) of handle assembly (20). Transducer assembly (12) is coupled with a generator (16) via a cable (14), such that transducer assembly (12) receives electrical power from generator (16). Piezoelectric elements in transducer assembly (12) convert that electrical power into ultrasonic vibrations. Generator (16) may include a power source and control module that is configured to provide a power profile to transducer assembly (12) that is particularly suited for the generation of ultrasonic vibrations through transducer assembly (12). By way of example only, generator (16) may comprise a GEN04, GEN11, or GEN 300 sold by Ethicon Endo-Surgery, Inc. of Cincinnati, Ohio. In addition or in the alternative, generator (16) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should also be understood that at least some of the functionality of generator (16) may be integrated into handle assembly (20), and that handle assembly (20) may even include a battery or other on-board power source such that cable (14) is omitted. Still other suitable forms that generator (16) may take, as well as various features and operabilities that generator (16) may provide, will be apparent to those of ordinary skill in the art in view of the teachings herein.

A. Exemplary End Effector and Acoustic Drivetrain

Figure 2:
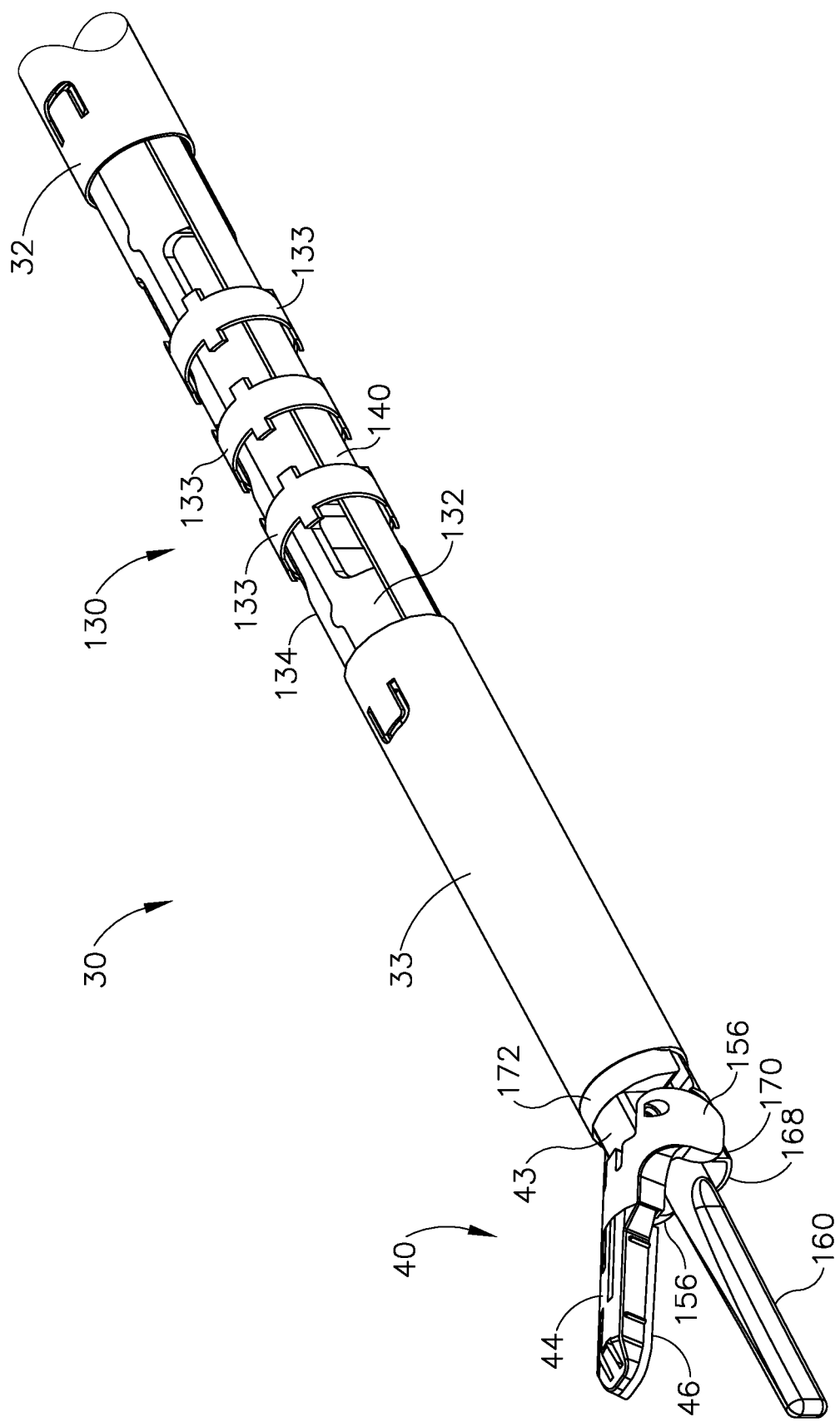
FIG. 2 depicts a perspective view of an articulation section of a shaft assembly and an end effector of the surgical instrument of FIG. 1.
Figure 3:
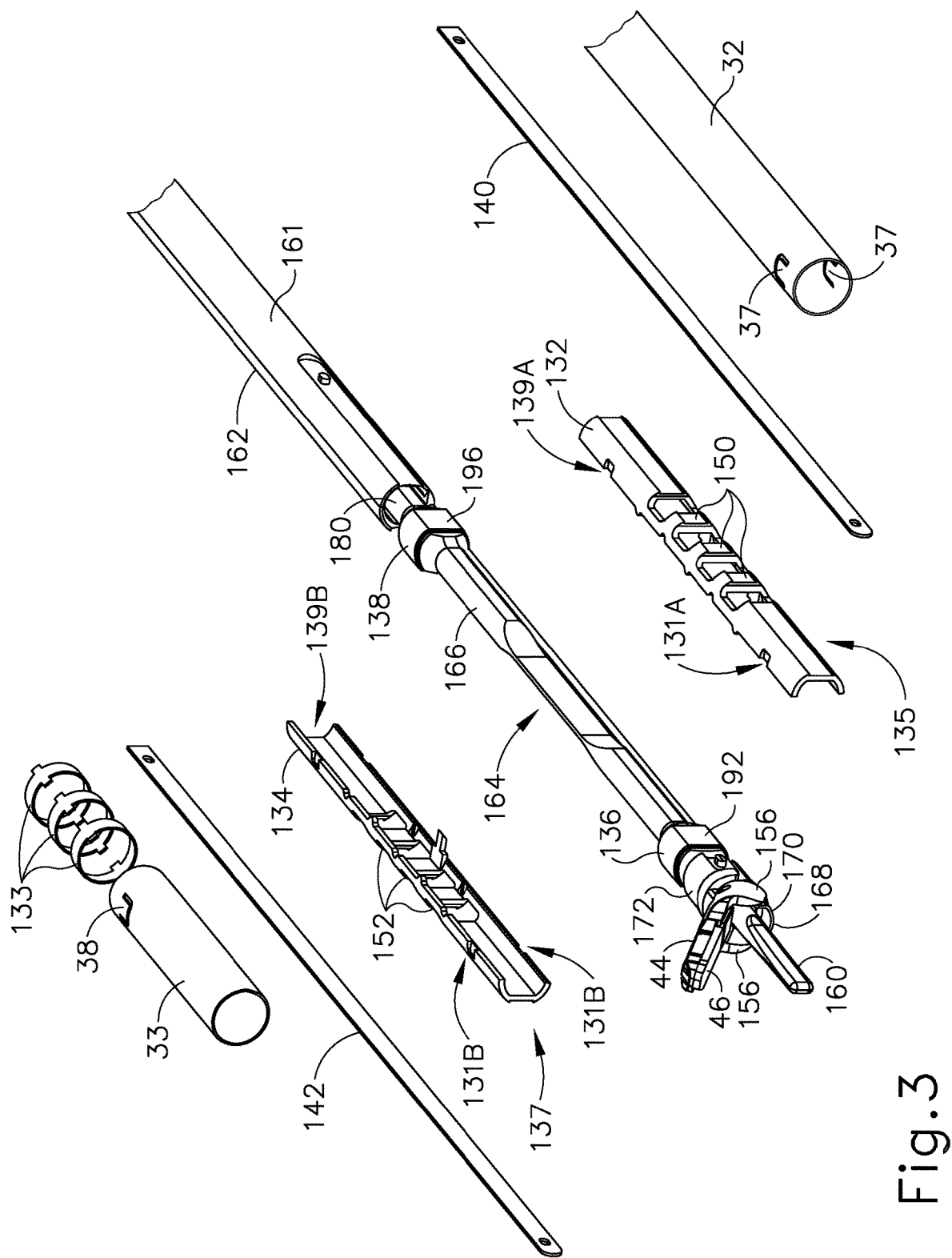
FIG. 3 depicts an exploded perspective view of an articulation section of the shaft assembly of FIG. 2.
Figure 4:
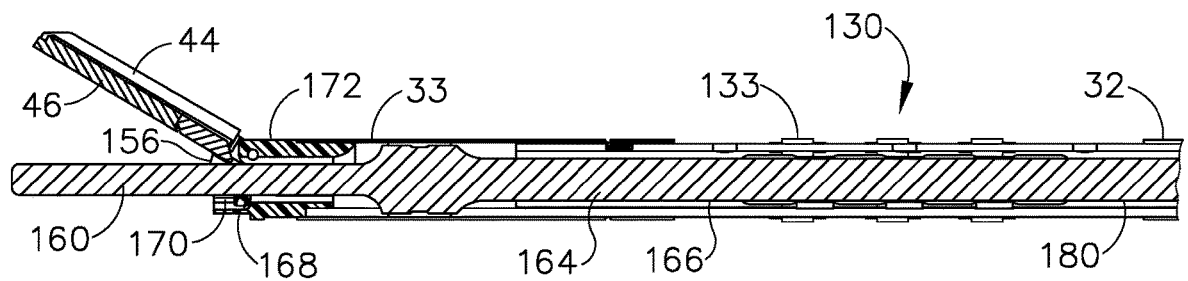
FIG. 4 depicts a cross-sectional side view of the shaft assembly and end effector of FIG. 2.

As best seen in FIGS. 2-4, end effector (40) of the present example comprises clamp arm (44) and ultrasonic blade (160). Clamp arm (44) includes a clamp pad (46) that is secured to the underside of clamp arm (44), facing blade (160). Clamp pad (46) may comprise polytetrafluoroethylene (PTFE) and/or any other suitable material(s). Clamp arm

(44) is pivotally secured to a distally projecting tongue (43) of an upper distal shaft element (172), which is fixedly secured within a distal portion of a distal outer sheath (33). Clamp arm (44) is operable to selectively pivot toward and away from blade (160) to selectively clamp tissue between clamp arm (44) and blade (160). A pair of arms (156) extend transversely from clamp arm (44) and are pivotally secured to a lower distal shaft element (170), which is slidably disposed within the distal portion of distal outer sheath (33).

Figure 7:
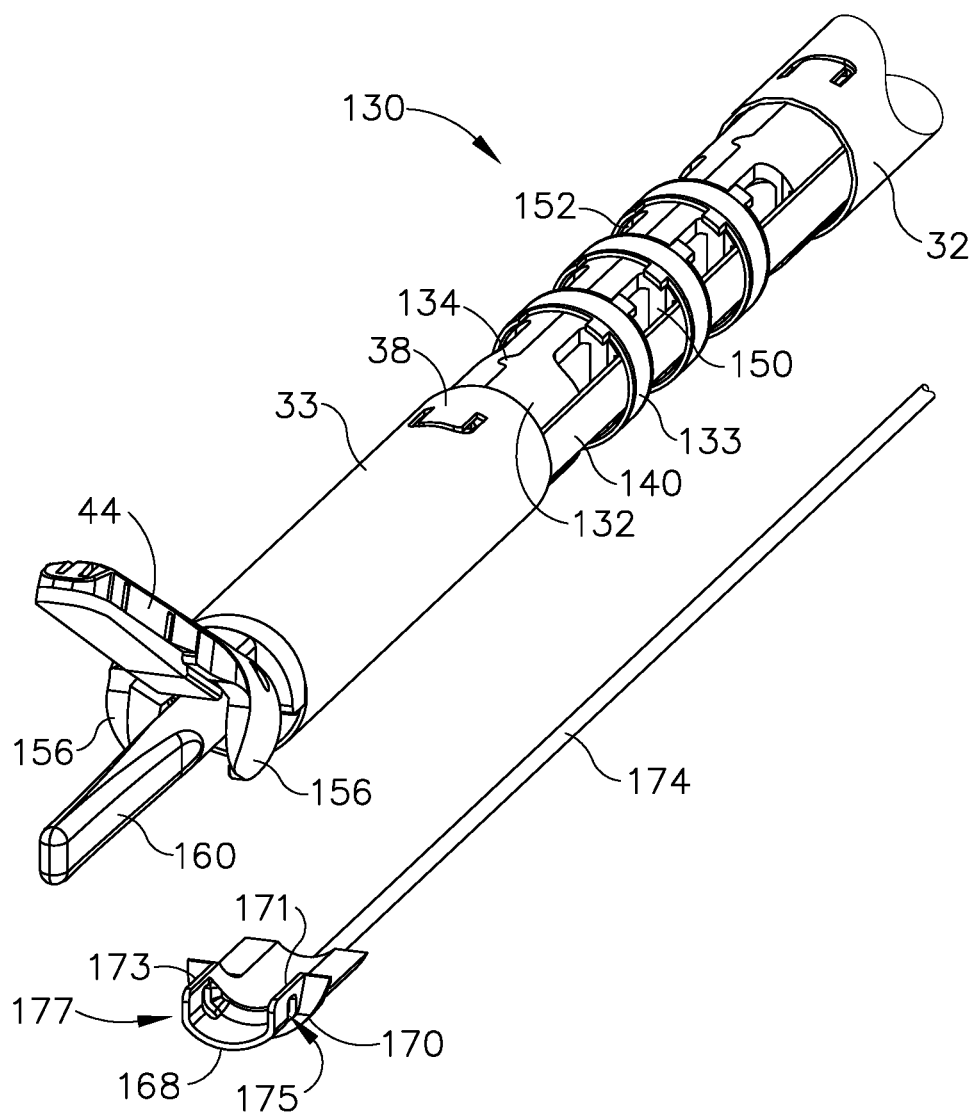
FIG. 7 depicts a partially exploded perspective view of the shaft assembly and end effector of FIG. 2.
Figure 8:
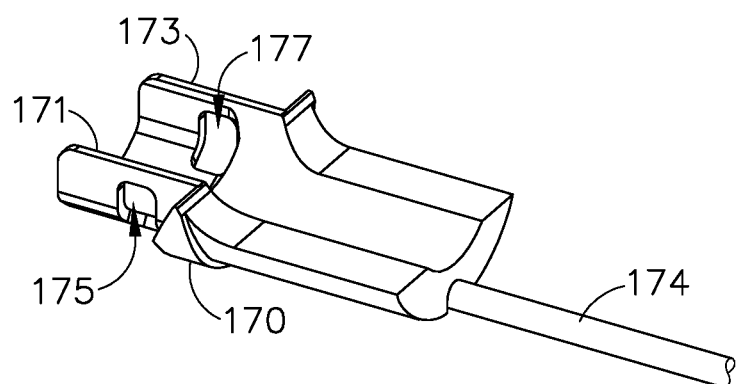
FIG. 8 depicts a perspective view of a distal collar and a drive cable of the shaft assembly of FIG. 2.

As best seen in FIGS. 7-8, a cable (174) is secured to lower distal shaft element (170). Cable (174) is operable to translate longitudinally relative to an articulation section (130) of shaft assembly (30) to selectively pivot clamp arm (44) toward and away from blade (160). In particular, cable (174) is coupled with trigger (28) such that cable (174) translates proximally in response to pivoting of trigger (28) toward pistol grip (24), and such that clamp arm (44) thereby pivots toward blade (160) in response to pivoting of trigger (28) toward pistol grip (24). In addition, cable (174) translates distally in response to pivoting of trigger (28) away from pistol grip (24), such that clamp arm (44) pivots away from blade (160) in response to pivoting of trigger (28) away from pistol grip (24). Clamp arm (44) may be biased toward the open position, such that (at least in some instances) the operator may effectively open clamp arm (44) by releasing a grip on trigger (28).

Figure 10A:
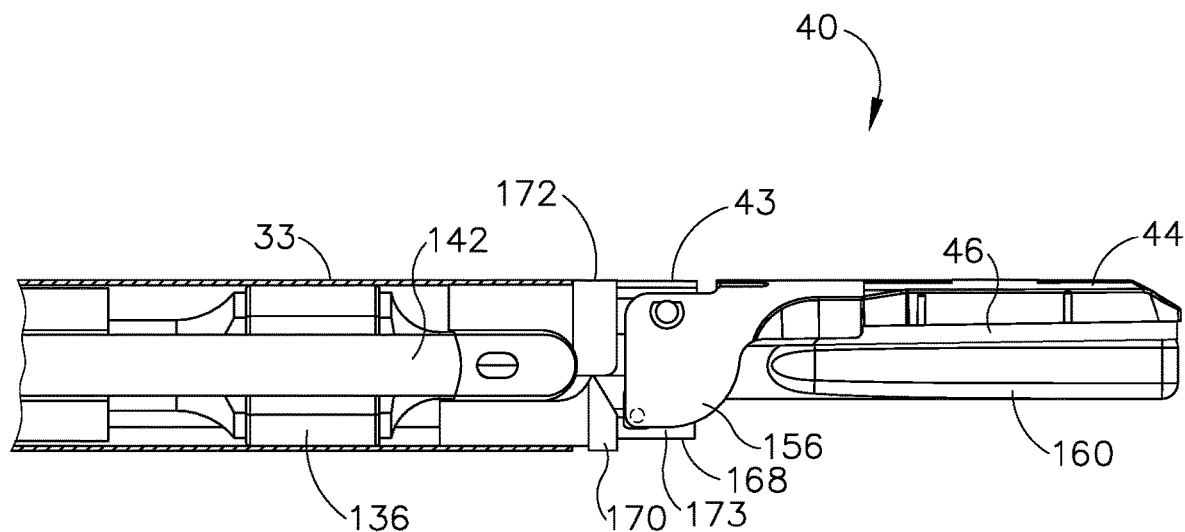
FIG. 10A depicts a side elevational view of the end effector and the distal portion of the shaft assembly of FIG. 2, with a clamp arm of the end effector in a closed position, and with an outer sheath shown in cross-section to reveal components within the outer sheath.
Figure 10B:
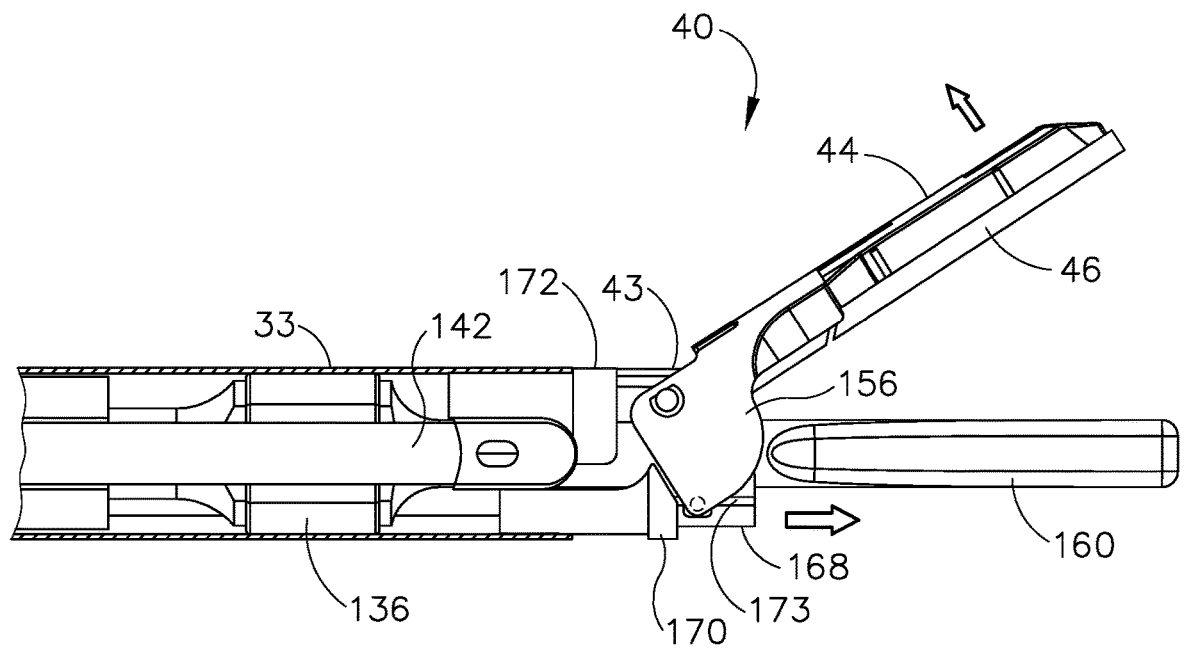
FIG. 10B depicts a side elevational view of the shaft assembly and end effector of FIG. 10A, with the clamp arm moved to a fully open position.

As shown in FIGS. 7-8, cable (174) is secured to a proximal end of lower distal shaft element (170). Lower distal shaft element (170) comprises a pair of distal flanges (171, 173) extending from a semi-circular base (168). Flanges (171, 173) each comprise a respective opening (175, 177). Clamp arm (44) is rotatably coupled to lower distal shaft element (170) via a pair of inwardly extending integral pins (41, 45). Pins (41, 45) extend inwardly from arms (156) of clamp arm (44) and are rotatably disposed within respective openings (175, 177) of lower distal shaft element (170). As shown in FIGS. 10A-10B, longitudinal translation of cable (174) causes longitudinal translation of lower distal shaft element (170) between a proximal position (FIG. 10A) and a distal position (FIG. 10B). Longitudinal translation of lower distal shaft element (170) causes rotation of clamp arm (44) between a closed position (FIG. 10A) and an open position (FIG. 10B).

Blade (160) of the present example is operable to vibrate at ultrasonic frequencies in order to effectively cut through and seal tissue, particularly when the tissue is being compressed between clamp pad (46) and blade (160). Blade (160) is positioned at the distal end of an acoustic drivetrain. This acoustic drivetrain includes transducer assembly (12) and an acoustic waveguide (180). Acoustic waveguide (180) comprises a flexible portion (166). As noted above, transducer assembly (12) is operable to convert electrical power into ultrasonic vibrations, which are then transmitted along waveguide (180), including flexible portion (166) of waveguide (180) to blade (160) in accordance with known configurations and techniques. By way of example only, this portion of the acoustic drivetrain may be configured in accordance with various teachings of various references that are cited herein.

As best seen in FIG. 3, flexible portion (166) of waveguide (180) includes a distal flange (136), a proximal flange (138), and a narrowed section (164) located between flanges (136, 138). In the present example, flanges (136, 138) are located at positions corresponding to nodes associated with resonant ultrasonic vibrations communicated through flexible portion (166) of waveguide (180). Narrowed section (164) is configured to allow flexible portion (166) of waveguide (180) to flex without significantly affecting the ability of flexible portion (166) of waveguide (180) to transmit ultrasonic vibrations. By way of example only, narrowed section (164) may be configured in accordance with one or more teachings of U.S. Pub. No. 2014/0005701, issued as U.S. Pat. No. 9,393,037 on Jul. 19, 2016, and/or U.S. Pub. No. 2014/0114334, issued as U.S. Pat. No. 9,095,367 on Aug. 4, 2015, the disclosures of which are incorporated by reference herein. It should be understood that waveguide (180) may be configured to amplify mechanical vibrations transmitted through waveguide (180). Furthermore, waveguide (180) may include features operable to control the gain of the longitudinal vibrations along waveguide (180) and/or features to tune waveguide (180) to the resonant frequency of the system. Various suitable ways in which waveguide (180) may be mechanically and acoustically coupled with transducer assembly (12) will be apparent to those of ordinary skill in the art in view of the teachings herein.

In the present example, the distal end of blade (160) is located at a position corresponding to an anti-node associated with resonant ultrasonic vibrations communicated through flexible portion (166) of waveguide (180), in order to tune the acoustic assembly to a preferred resonant frequency $f_o$ when the acoustic assembly is not loaded by tissue. When transducer assembly (12) is energized, the distal end of blade (160) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through waveguide (180) to reach blade (160), thereby providing oscillation of blade (160) at the resonant ultrasonic frequency. Thus, when tissue is secured between blade (160) and clamp pad (46), the ultrasonic oscillation of blade (160) may simultaneously sever the tissue and denature the proteins in adjacent tissue cells, thereby providing a coagulative effect with relatively little thermal spread.

In some versions, end effector (40) is operable to apply radiofrequency (RF) electrosurgical energy to tissue in addition to applying ultrasonic energy to tissue. By way of example only, end effector (40) may be configured and operable in accordance with at least some of the teachings of U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein; and/or U.S. Pat. No. 8,663,220, entitled "Ultrasonic Electrosurgical Instruments," issued Mar. 4, 2014, the disclosure of which is incorporated by reference herein.

Other suitable configurations for an acoustic transmission assembly and transducer assembly (12) will be apparent to one or ordinary skill in the art in view of the teachings herein. Similarly, other suitable configurations for end effector (40) will be apparent to those of ordinary skill in the art in view of the teachings herein.

B. Exemplary Shaft Assembly and Articulation Section

Shaft assembly (30) of the present example extends distally from handle assembly (20). As shown in FIGS. 2-7, shaft assembly (30) includes distal outer sheath (33) and a proximal outer sheath (32) that enclose clamp arm (44) drive features and the above-described acoustic transmission features. Shaft assembly (30) further includes an articulation section (130), which is located at a distal portion of shaft assembly (30), with end effector (40) being located distal to articulation section (130). As shown in FIG. 1, a rotation control assembly (102) has rotation control member in the form of rotation control knob (31), which is secured to a proximal portion of proximal outer sheath (32). Knob (31) is rotatable relative to body (22), such that shaft assembly (30) is rotatable about the longitudinal axis defined by outer sheath (32), relative to handle assembly (20). Such rotation may provide rotation of end effector (40), articulation section (130), and shaft assembly (30) unitarily. Of course, rotatable features may simply be omitted if desired.

Articulation section (130) is operable to selectively position end effector (40) at various lateral deflection angles relative to a longitudinal axis defined by outer sheath (32). Articulation section (130) may take a variety of forms. By way of example only, articulation section (130) may be configured in accordance with one or more teachings of U.S. Pub. No. 2012/0078247, issued as U.S. Pat. No. 9,402,682 on Aug. 2, 2016, the disclosure of which is incorporated by reference herein. As another merely illustrative example, articulation section (130) may be configured in accordance with one or more teachings of U.S. Pub. No. 2014/0005701, issued as U.S. Pat. No. 9,393,037 on Jul. 19, 2016and/or U.S. Pub. No. 2014/0114334, issued as U.S. Pat. No. 9,095,367 on Aug. 4, 2015, the disclosures of which are incorporated by reference herein. Various other suitable forms that articulation section (130) may take will be apparent to those of ordinary skill in the art in view of the teachings herein.

As best seen in FIGS. 2-6B articulation section (130) of this example comprises a set of three retention collars (133) and a pair of ribbed body portions (132, 134), with a pair of articulation bands (140, 142) extending along respective channels (135, 137) defined between interior surfaces of retention collars (133) and exterior surfaces of ribbed body portions (132, 134). Ribbed body portions (132, 134) are longitudinally positioned between flanges (136, 138) of flexible portion (166) of waveguide (180). In some versions, ribbed body portions (132, 134) snap together about flexible portion (166) of waveguide (180). Ribbed body portions (132, 134) are configured to flex with flexible portion (166) of waveguide (180) when articulation section (130) bends to achieve an articulated state.

FIG. 3 shows ribbed body portions (132, 134) in greater detail. In the present example, ribbed body portions (132, 134) are formed of a flexible plastic material, though it should be understood that any other suitable material may be used. Ribbed body portion (132) comprises a set of three ribs (150) that are configured to promote lateral flexing of ribbed body portion (132). Of course, any other suitable number of ribs (150) may be provided. Ribbed body portion (132) also defines a channel (135) that is configured to receive articulation band (140) while allowing articulation band (140) to slide relative to ribbed body portion (132). Similarly, ribbed body portion (134) comprises a set of three ribs (152) that are configured to promote lateral flexing of ribbed body portion (134). Of course, any other suitable number of ribs (152) may be provided. Ribbed body portion (134) also defines a channel (137) that is configured to receive articulation band (142) while allowing articulation band (142) to slide relative to ribbed body portion (137).

Figure 5:
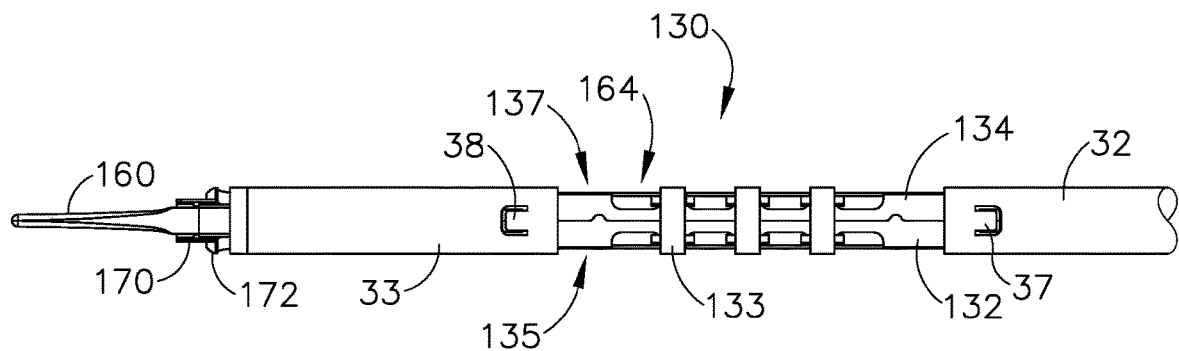
FIG. 5 depicts a top plan view of the shaft assembly and end effector of FIG. 2.

As best seen in FIG. 5, ribbed body portions (132, 134) are laterally interposed between articulation bands (140, 142) and flexible portion (166) of waveguide (180). Ribbed body portions (132, 134) mate with each other such that they together define an internal passage sized to accommodate flexible portion (166) of waveguide (180) without contacting waveguide (180). In addition, when ribbed body portions (132, 134) are coupled together, a pair of complementary distal notches (131A, 131B) formed in ribbed body portions (132, 134) align to receive a pair of inwardly projecting resilient tabs (38) of distal outer sheath (33). This engagement between tabs (38) and notches (131A, 131B) longitudinally secures ribbed body portions (132, 134) relative to distal outer sheath (33). Similarly, when ribbed body portions (132, 134) are coupled together, a pair of complementary proximal notches (139A, 139B) formed in ribbed body portions (132, 134) align to receive a pair of inwardly projecting resilient tabs (37) of proximal outer sheath (32). This engagement between tabs (37) and notches (139A, 139B) longitudinally secures ribbed body portions (132, 134) relative to proximal outer sheath (32). Of course, any other suitable kinds of features may be used to couple ribbed body portions (132, 134) with proximal outer sheath (32) and/or distal outer sheath (33).

Figure 6A:
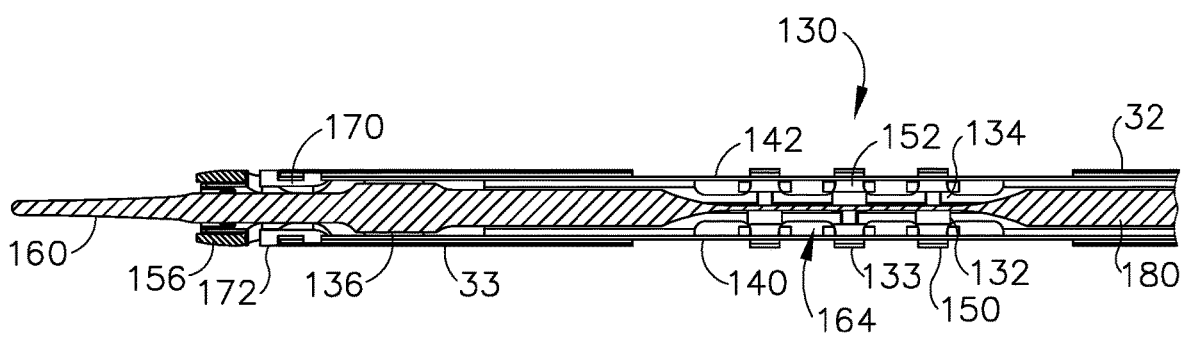
FIG. 6A depicts a cross-sectional top view of the shaft assembly and end effector of FIG. 2 in a straight configuration.
Figure 6B:
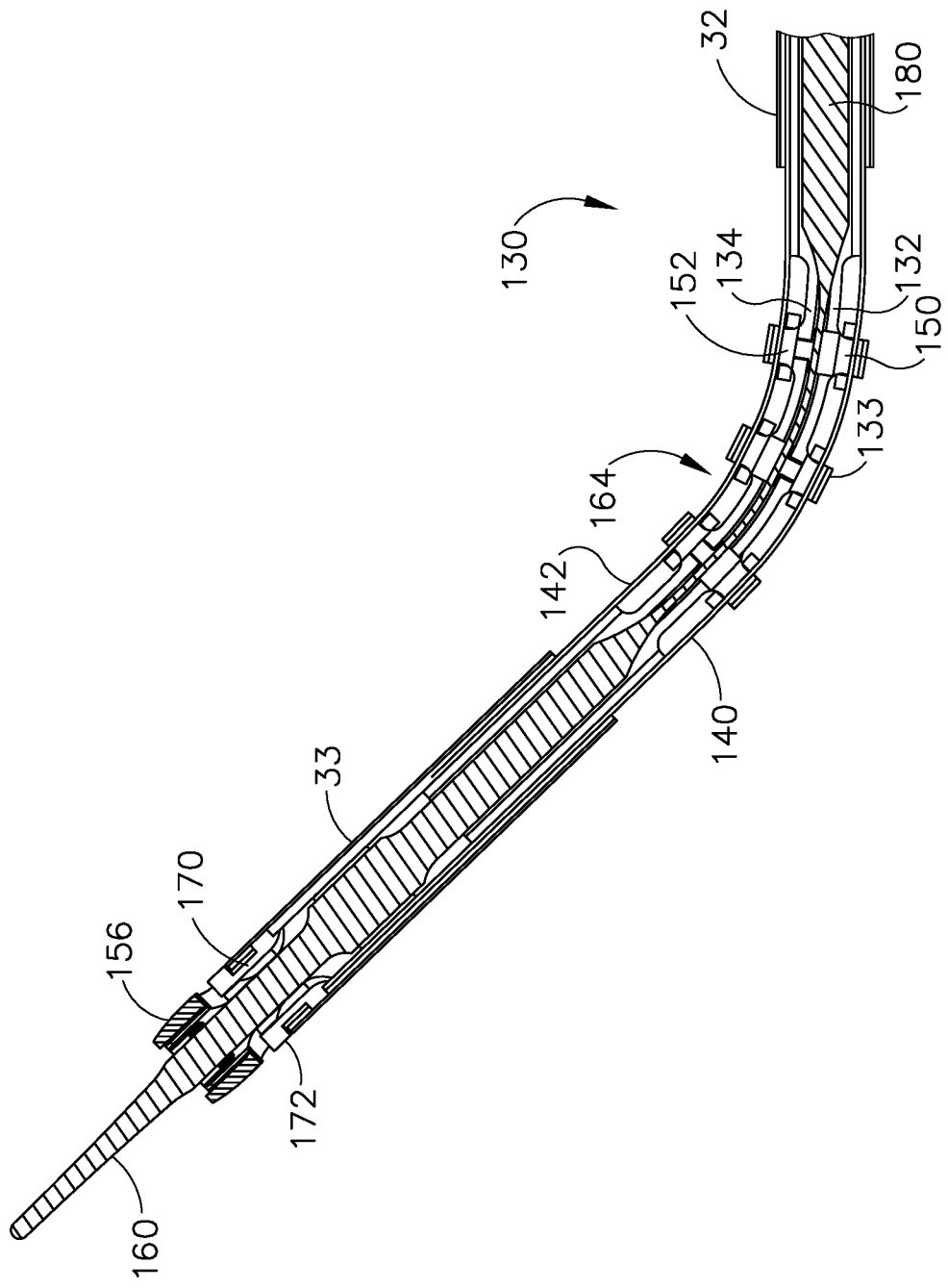
FIG. 6B depicts a cross-sectional top view of the shaft assembly and end effector of FIG. 2 in an articulated configuration.

The distal ends of articulation bands (140, 142) are unitarily secured to upper distal shaft element (172). When articulation bands (140, 142) translate longitudinally in an opposing fashion, this will cause articulation section (130) to bend, thereby laterally deflecting end effector (40) away from the longitudinal axis of shaft assembly (30) from a straight configuration as shown in FIG. 6A to an articulated configuration as shown in FIG. 6B. In particular, end effector (40) will be articulated toward the articulation band (140, 142) that is being pulled proximally. During such articulation, the other articulation band (140, 142) may be pulled distally by upper distal shaft element (172). Alternatively, the other articulation band (140, 142) may be driven distally by an articulation control. Ribbed body portions (132, 134) and narrowed section (164) are all sufficiently flexible to accommodate the above-described articulation of end effector (40). Furthermore, flexible acoustic waveguide (166) is configured to effectively communicate ultrasonic vibrations from waveguide (180) to blade (160) even when articulation section (130) is in an articulated state as shown in FIG. 6B.

As best seen in FIG. 3, each flange (136, 138) of waveguide (180) includes a respective pair of opposing flats (192, 196). Flats (192, 196) are oriented along vertical planes that are parallel to a vertical plane extending through narrowed section (164) of flexible portion (166). Flats (192, 196) are configured to provide clearance for articulation bands (140, 142). In particular, flats (196) of proximal flange (138) accommodate articulation bands (140, 142) between proximal flange (138) and the inner diameter of proximal outer sheath (32): while flats (192) of distal flange (136) accommodate articulation bands (140, 142) between distal flange (136) and the inner diameter of distal outer sheath (33). Of course, flats (192, 196) could be substituted with a variety of features, including but not limited to slots, channels, etc., with any suitable kind of profile (e.g., square, flat, round, etc.). In the present example, flats (192, 196) are formed in a milling process, though it should be understood that any other suitable process(es) may be used. Various suitable alternative configurations and methods of forming flats (192, 196) will be apparent to those of ordinary skill in the art in view of the teachings herein. It should also be understood that waveguide (180) may include flats formed in accordance with at least some of the teachings of U.S. Pub. No. 2013/0289592, entitled "Ultrasonic Device for Cutting and Coagulating," filed Apr. 23, 2013, issued as U.S. Pat. No. 10,238,416 on Mar. 26, 2019, the disclosure of which is incorporated by reference herein.

In the present example, outer rings (133) are located at longitudinal positions corresponding to ribs (150, 152), such that three rings (133) are provided for three ribs (150, 152). Articulation band (140) is laterally interposed within channel (135) between rings (133) and ribbed body portion (132); while articulation band (142) is laterally interposed within channel (137) between rings (133) and ribbed body portion (134). Rings (133) are configured to keep articulation bands (140, 142) in a parallel relationship, particularly when articulation section (130) is in a bent configuration (e.g., similar to the configuration shown in FIG. 6B). In other words, when articulation band (140) is on the inner diameter of a curved configuration presented by a bent articulation section (130), rings (133) may retain articulation band (140) such that articulation band (140) follows a curved path that complements the curved path followed by articulation band (142). It should be understood that channels (135, 137) are sized to accommodate respective articulation bands (140, 142) in such a way that articulation bands (140, 142) may still freely slide through articulation section (130), even with rings (133) being secured to ribbed body portions (150, 152). It should also be understood that rings (133) may be secured to ribbed body portions (132, 134) in various ways, including but not limited to interference fitting, adhesives, welding, etc.

When articulation bands (140, 142) are translated longitudinally in an opposing fashion, a moment is created and applied to a distal end of distal outer sheath (33) via upper distal shaft element (172). This causes articulation section (130) and narrowed section (164) of flexible portion (166) of waveguide (180) to articulate, without transferring axial forces in articulation bands (140, 142) to waveguide (180). It should be understood that one articulation band (140, 142) may be actively driven distally while the other articulation band (140, 142) is passively permitted to retract proximally. As another merely illustrative example, one articulation band (140, 142) may be actively driven proximally while the other articulation band (140, 142) is passively permitted to advance distally. As yet another merely illustrative example, one articulation band (140, 142) may be actively driven distally while the other articulation band (140, 142) is actively driven proximally. Various suitable ways in which articulation bands (140, 142) may be driven will be apparent to those of ordinary skill in the art in view of the teachings herein.

Figure 9:
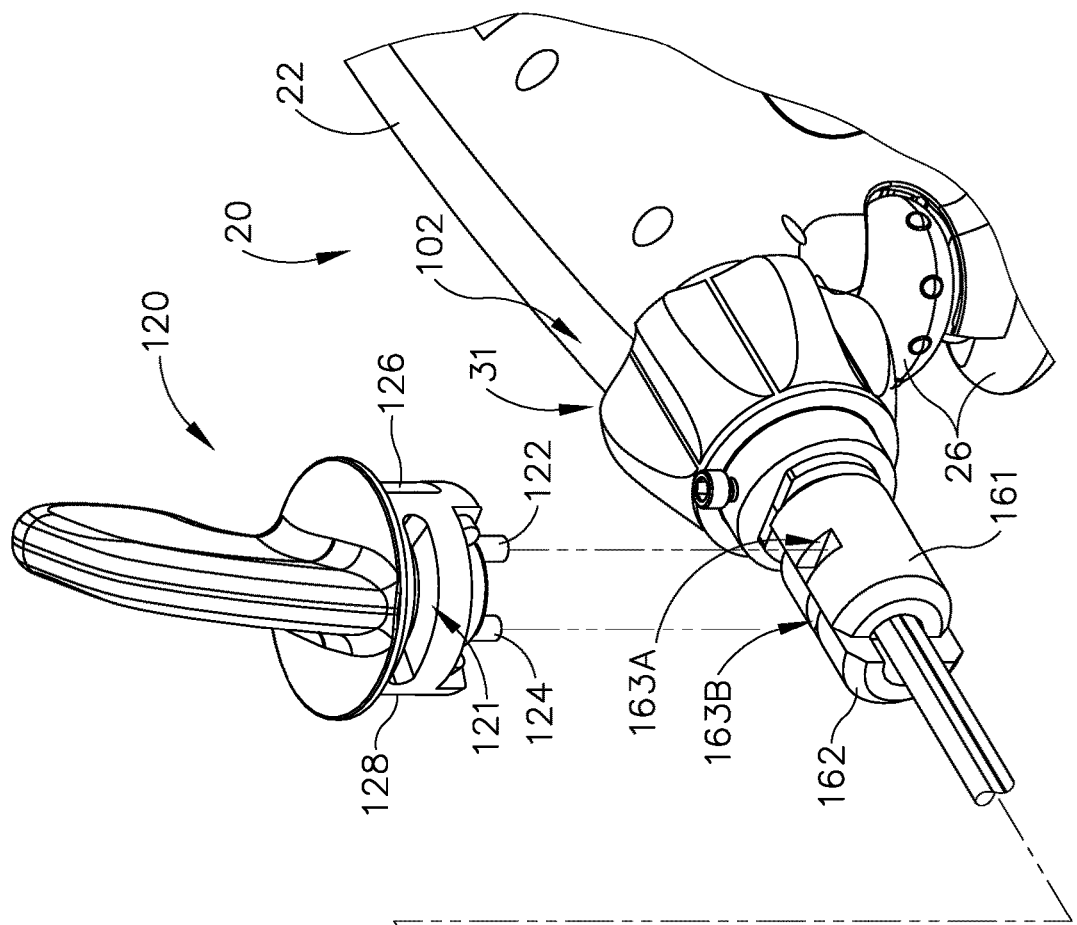
FIG. 9 depicts a partially exploded perspective view of an shaft control assembly of the instrument of FIG. 1.
Figure 9:
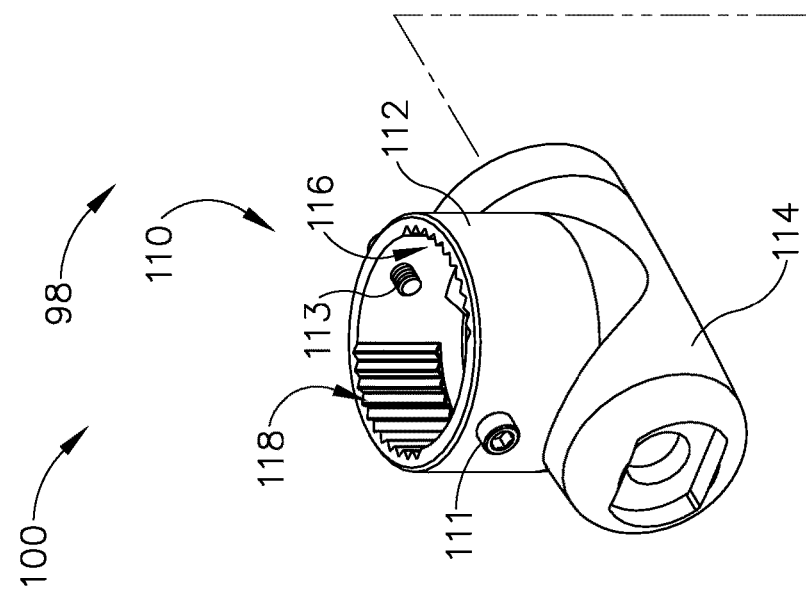

As best seen in FIG. 9, an articulation control assembly (100) is secured to a proximal portion of outer sheath (32). Articulation control assembly (100) comprises a housing (110) and an articulation control member in the form of a rotatable articulation control knob (120). As shown and described herein, exemplary articulation control assembly (100) and exemplary rotation control assembly (102), which is discussed above in greater detail, collectively define a shaft control assembly (98). Housing (110) comprises a pair of perpendicularly intersecting cylindrical portions (112, 114). Knob (120) is rotatably disposed within a first hollow cylindrical portion (112) of housing (110) such that knob (120) is operable to rotate within cylindrical portion (112) of housing (110). Shaft assembly (30) is slidably and rotatably disposed within a second hollow cylindrical portion (114). Shaft assembly (30) comprises a pair of translatable members (161, 162), both of which extend slidably and longitudinally through the proximal portion of outer sheath (32). Translatable members (161, 162) are longitudinally translatable within second cylindrical portion (114) between a distal position and a proximal position. Translatable members (161, 162) are mechanically coupled with respective articulation bands (140, 142) such that longitudinal translation of translatable member (161) causes longitudinal translation of articulation band (140), and such that longitudinal translation of translatable member (162) causes longitudinal translation of articulation band (142).

Knob (120) comprises a pair of pins (122, 124) extending downwardly from a bottom surface of knob (120). Pins (122, 124) extend into second cylindrical portion (114) of housing (110) and are rotatably and slidably disposed within a respective pair of channels (163A, 163B) formed in top surfaces of translatable members (161, 162). Channels (163A, 163B) are positioned on opposite sides of an axis of rotation of knob (120), such that rotation of knob (120) about that axis causes opposing longitudinal translation of translatable members (161, 162). For instance, rotation of knob (120) in a first direction causes distal longitudinal translation of translatable member (161) and articulation band (140), and proximal longitudinal translation of translatable member (162) and articulation band (142); and rotation of knob (120) in a second direction causes proximal longitudinal translation of translatable member (161) and articulation band (140), and distal longitudinal translation of translatable member (162) and articulation band (142). Thus, it should be understood that rotation of rotation knob (120) causes articulation of articulation section (130).

Housing (110) of articulation control assembly (100) comprises a pair of set screws (111, 113) extending inwardly from an interior surface of first cylindrical portion (112). With knob (120) rotatably disposed within first cylindrical portion (112) of housing (110), set screws (111, 113) are slidably disposed within a pair of arcuate channels (121, 123) formed in knob (120). Thus, it should be understood that rotation of knob (120) will be limited by movement of set screws (111, 113) within channels (121, 123). Set screws (111, 113) also retain knob (120) in housing (110), preventing knob (120) from traveling vertically within first cylindrical portion (112) of housing (110).

An interior surface of first cylindrical portion (112) of housing (110) comprises a first angular array of teeth (116) and a second angular array of teeth (118) formed in an interior surface of first cylindrical portion (112). Rotation knob (120) comprises a pair of outwardly extending engagement members (126, 128) that are configured to engage teeth (116, 118) of first cylindrical portion (112) in a detent relationship to thereby selectively lock knob (120) in a particular rotational position. The engagement of engagement members (126, 128) with teeth (116, 118) may be overcome by a user applying sufficient rotational force to knob (120); but absent such force, the engagement will suffice to maintain the straight or articulated configuration of articulation section (130). It should therefore be understood that the ability to selectively lock knob (120) in a particular rotational position lock will enable an operator to selectively lock articulation section (130) in a particular deflected position relative to the longitudinal axis defined by outer sheath (32).

In addition to or in lieu of the foregoing, articulation section (130) and/or articulation control assembly (100) may be constructed and/or operable in accordance with at least some of the teachings of U.S. patent application Ser. No. 14/688,458, entitled "Ultrasonic Surgical Instrument with Rigidizing Articulation Drive Members," filed on Apr. 16, 2015, issued as U.S. Pat. No. 10,034,683 on Jul. 31, 2018. Alternatively, articulation section (130) and/or articulation control assembly (100) may be constructed and/or operable in any other suitable fashion.

II. EXEMPLARY ALTERNATIVE SHAFT CONTROL ASSEMBLIES

In some versions of surgical instrument (10, 210, 310, 410, 510, 710, 910) it may be desirable to provide features that are configured to selectively provide rigidity to articulation section (130) and thereby prevent inadvertent deflection of articulation section (130). For instance, because of various factors such as manufacturing tolerances, design limitations, material limitations, and/or other factors, some versions of articulation section (130) may be susceptible to some "play" or other small movement of the articulation section despite being relatively fixed in a given position, such that articulation section (130) is not entirely rigid. It may be desirable to reduce or eliminate such play in articulation section (130), particularly when articulation section (130) is in a straight, non-articulated configuration. Similarly, it may be desirable to selectively lock articulation control features to prevent inadvertent actuation of such articulation control features. Features may thus be provided to selectively rigidize and/or otherwise lock articulation section (130). Various examples of features that are configured to selectively provide rigidity to articulation section (130) and/or to limit, inhibit, or effectively prevent inadvertent deflection of end effector (40) will be described in greater detail below. Other examples will be apparent to those of ordinary skill in the art according to the teachings herein. It should be understood that the examples of shaft assemblies and/or articulation sections described below may function substantially similar to shaft assembly (30) discussed above. To this end, like numbers indicate like features.

It should also be understood that articulation section (130) may still be at least somewhat rigid before being modified to include the features described below, such that the features described below actually just increase the rigidity of articulation section (130) rather than introducing rigidity to an otherwise non-rigid articulation section (130). For instance, an articulation section (130) in the absence of features as described below may be rigid enough to substantially maintain a straight or articulated configuration; yet may still provide "play" of about 1 mm or a fraction thereof (e.g., when end effector (40) is pressed laterally against a fixed structure), esuch that the already existing rigidity of articulation section (130) may be increased. Thus, terms such as "provide rigidity" and "providing rigidity" shall be understood to include just increasing rigidity that is already present in some degree. The terms "provide rigidity" and "providing rigidity" should not be read as necessarily requiring articulation section (130) to completely lack rigidity before the rigidity is "provided."

Figure 11:
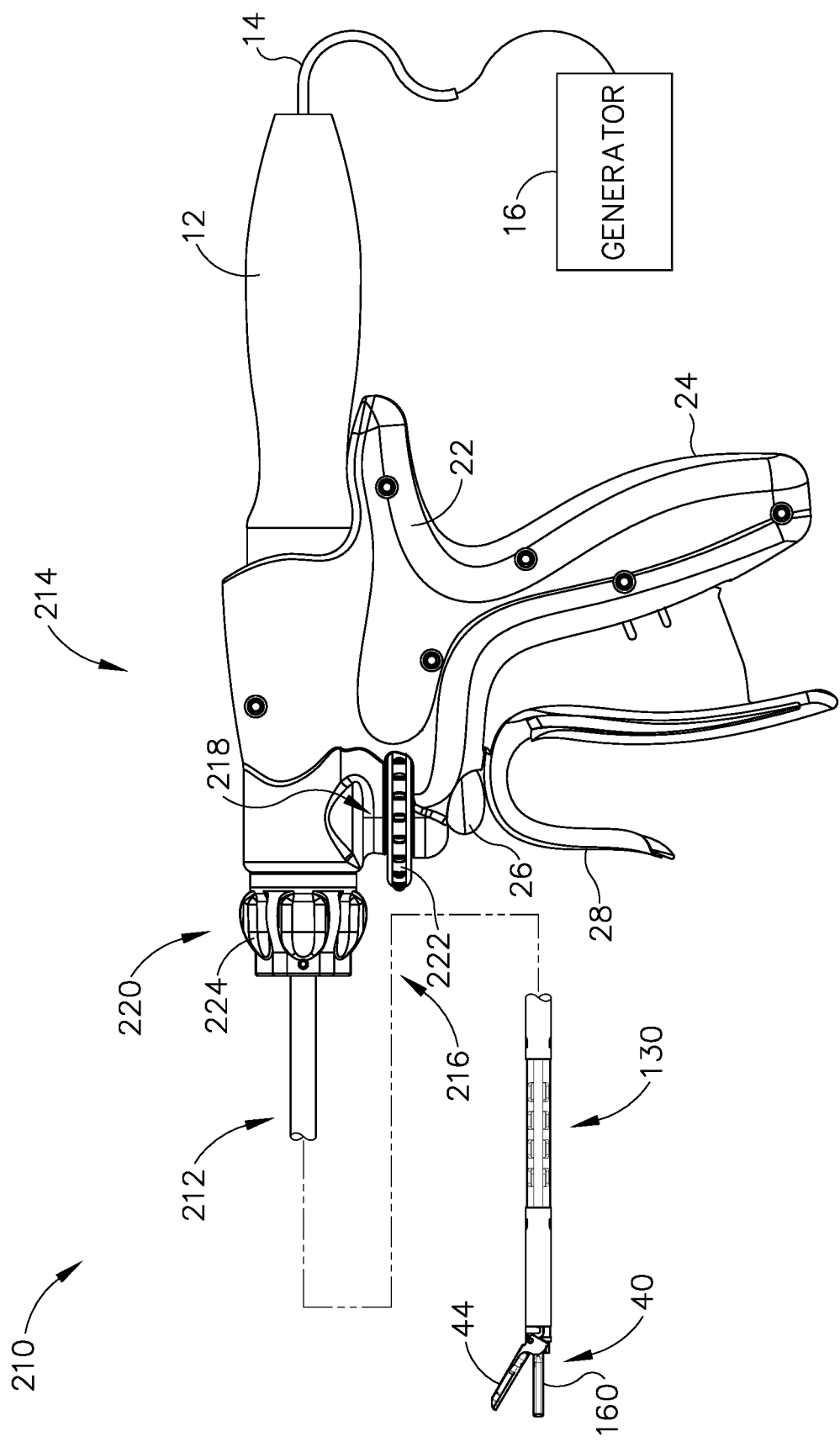
FIG. 11 depicts a side elevational view of a second exemplary ultrasonic surgical instrument having a shaft control assembly.
Figure 12:
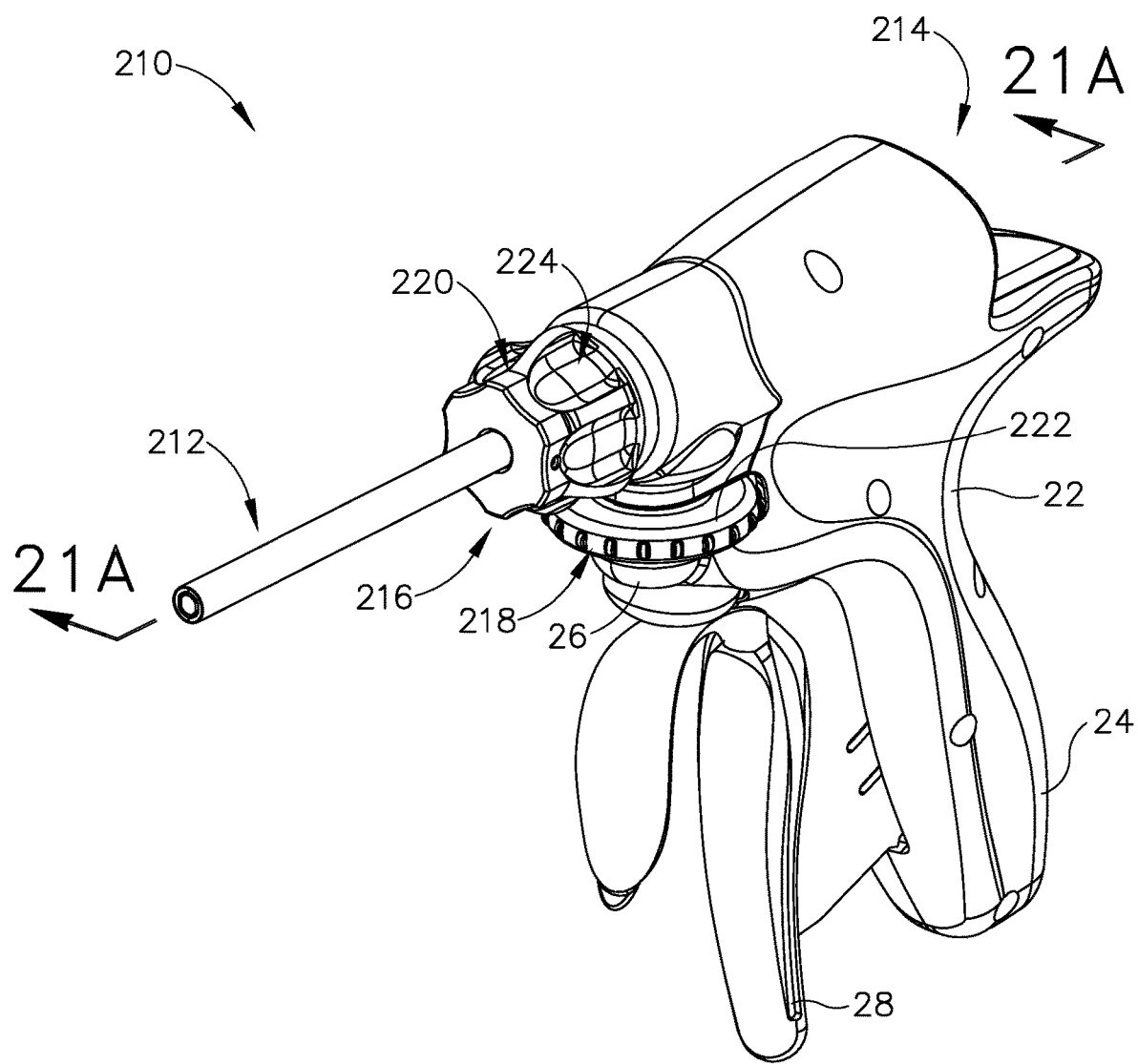
FIG. 12 depicts a perspective view of the surgical instrument of FIG. 11.

A. Exemplary Articulation Control Assembly with a Transmission Assembly including Bevel Gears FIGS. 11 and 12 show a second ultrasonic surgical instrument (210) having a shaft assembly (212), a handle assembly (214), end effector (40), and acoustic waveguide (80) extending therealong. As discussed above, acoustic waveguide (80) is operatively connected to generator (16) and shaft assembly (212), which includes articulation section (130) for positioning end effector (40) during a surgical procedure. To this end, surgical instrument (210) includes a shaft control assembly (216). Shaft control assembly (216) is operable to rotate shaft assembly (212) about the longitudinal axis of shaft assembly (212). Shaft control assembly (216) is also operable to articulate articulation section (130) to thereby deflect end effector (40) laterally away from the longitudinal axis of shaft assembly (212).

Shaft control assembly (216) more particularly includes an articulation control assembly (218) that is operatively connected to the articulation section (130); and a rotation control assembly (220) operatively connected to shaft assembly (212). Control assemblies (218, 220) are configured to be manipulated by the operator for selectively articulating and rotating shaft assembly (212) via respective articulation and rotation control members (222, 224). Articulation control assembly (218) further includes a transmission assembly (226) that is configured to transmit selective manipulation of articulation control member (222) to shaft assembly (212) for flexing articulation section (130). In order to provide rigidity to shaft assembly (212) and inhibit flexing of articulation section (130), articulation control assembly (218) is configured to lock when articulation control member (222) is not being selectively manipulated by the operator. However, articulation control assembly (218) unlocks when the articulation control member (222) is being selectively manipulated by the operator to flex articulation section (130).

Figure 13:
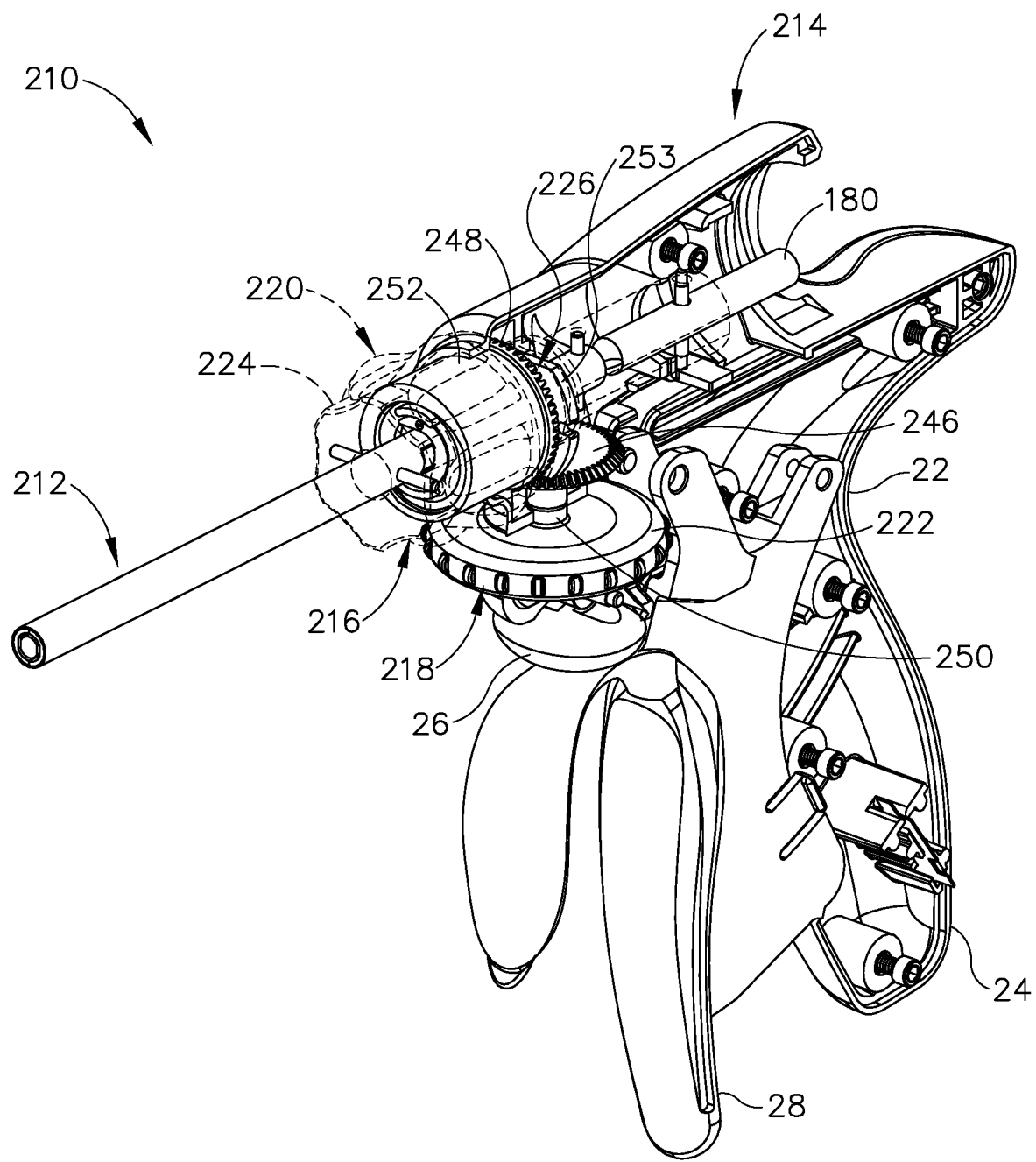
FIG. 13 depicts the perspective view of the surgical instrument of FIG. 11, with various components removed for clarity.

A proximal portion of shaft control assembly (216) is contained within housing (22) of handle assembly (214), whereas a distal portion of shaft control assembly (216) extends along a proximal portion of shaft assembly (212) exterior of housing (22). With respect to FIG. 13, a lateral side portion (not shown) of housing (22) is removed to more clearly illustrate the proximal portion of shaft control assembly (216). In the present example, rotation and articulation control members (224, 222) are respectively in the form of a selectively rotatable rotation control knob (224) and a selectively rotatable articulation control knob (222). Rotation control knob (224) extends along the longitudinal axis of shaft assembly (212) and is configured to rotate about the longitudinal axis. In contrast, articulation control knob (222) extends along a transverse axis and is configured to rotate about the transverse axis. Rotation and articulation control knobs (224, 222) thus rotate about respective axes that are perpendicular to each other.

Control knobs (224, 222) are also positioned proximate to trigger (28) of handle assembly (214) such that the operator can simultaneously access and manipulate trigger (28), rotation control knob (224), and articulation control knob (222). In the present example, articulation control knob (222) is received within a knob slot (228) (see FIG. 21A) transversely positioned between rotation control knob (224) and trigger (28). More details regarding the rotatable mounting of articulation control knob (222) to handle assembly (214) will be provided below with reference to FIG. 21A. While the above description positions exemplary shaft control assembly (216) at least partially within handle assembly (214), with the positions of the rotation and articulation control knobs (224, 222) proximate to trigger (28), it will be appreciated that one or more portions of shaft control assembly (216) may be alternatively positioned for operative connection with shaft assembly (212). Thus, the invention is not intended to be unnecessarily limited to the specific orientation and placement of the shaft control assembly (216) as described herein.

Figure 14:
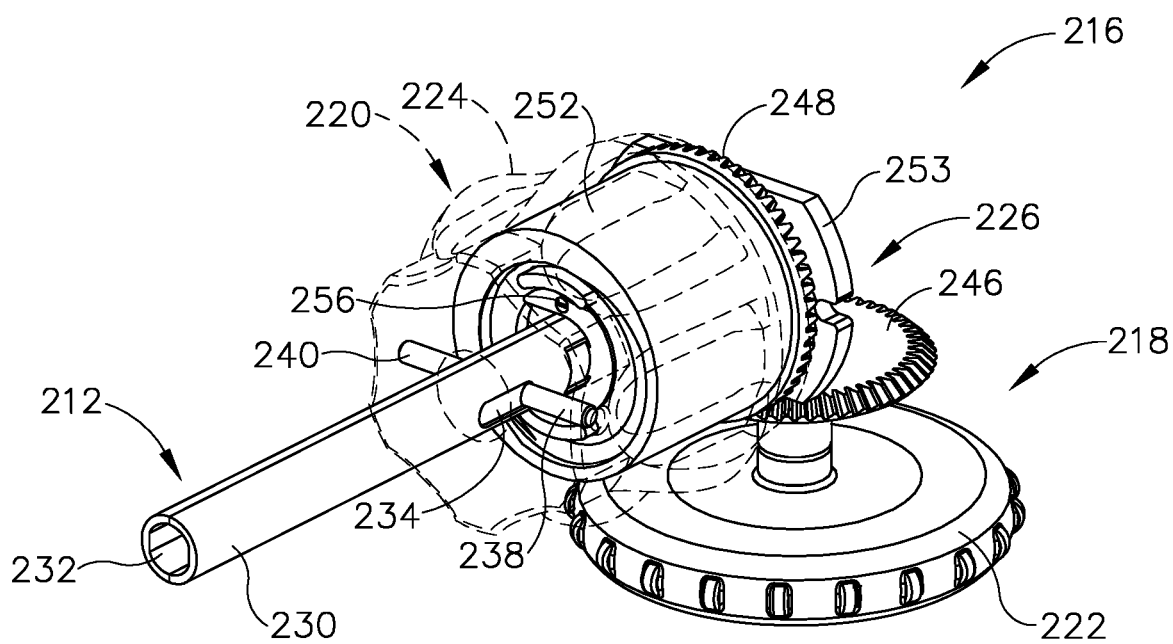
FIG. 14 depicts a front perspective view of the shaft control assembly of the surgical instrument of FIG. 11.
Figure 15:
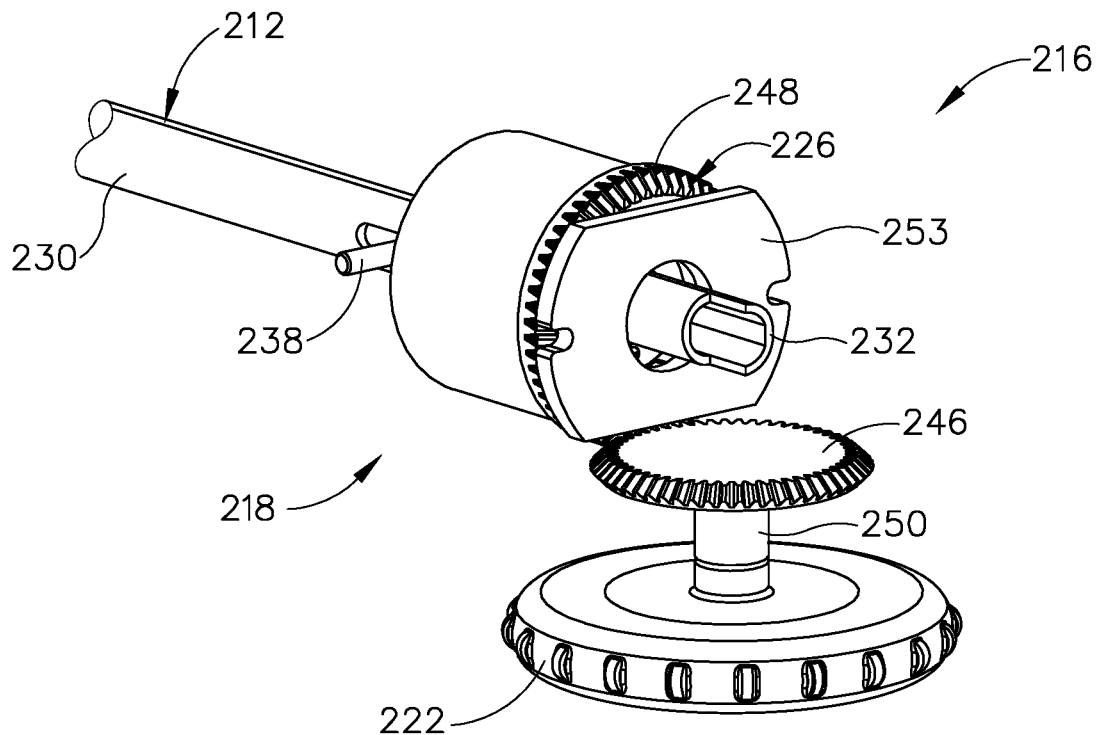
FIG. 15 depicts a rear perspective view of the shaft control assembly of FIG. 14.
Figure 16:
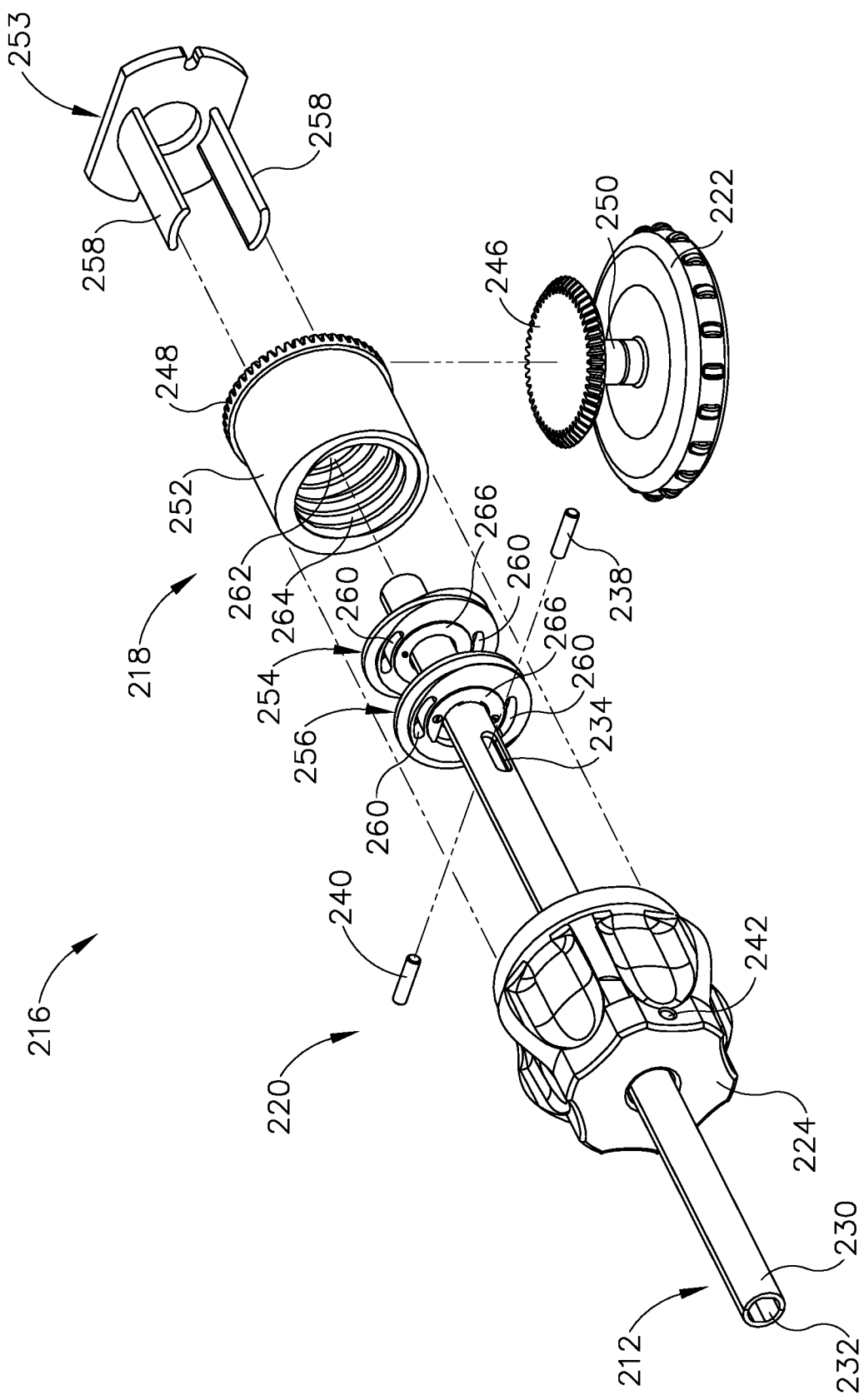
FIG. 16 depicts a partially exploded front perspective view of the shaft control assembly of FIG. 14.
Figure 17:
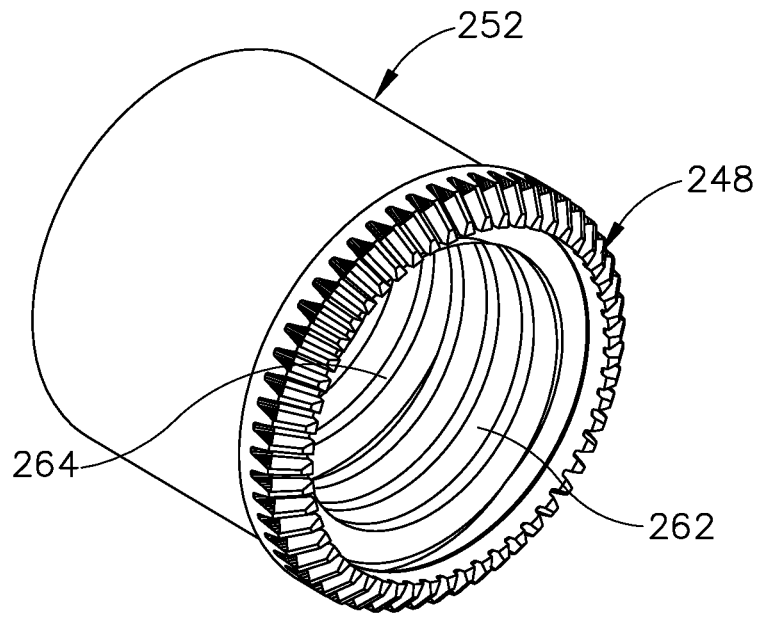
FIG. 17 depicts a rear perspective view of a drive housing of the shaft control assembly of FIG. 14.
Figure 18:
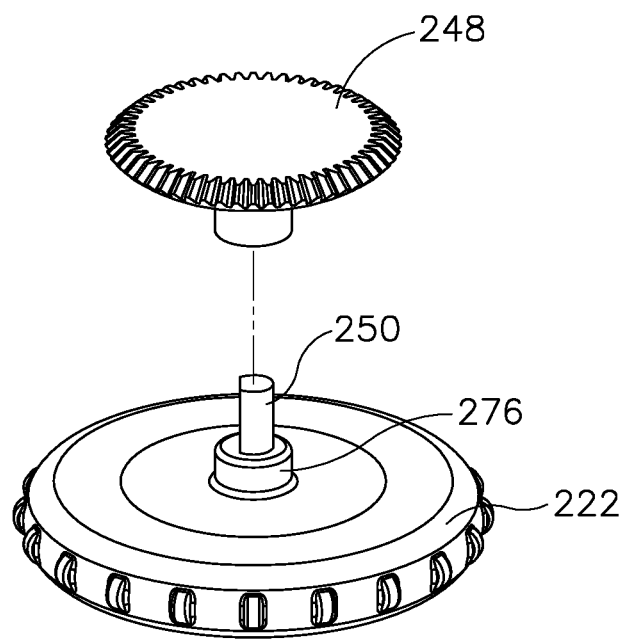
FIG. 18 depicts an exploded perspective view of an articulation control knob of the shaft control assembly of FIG. 14.
Figure 19:
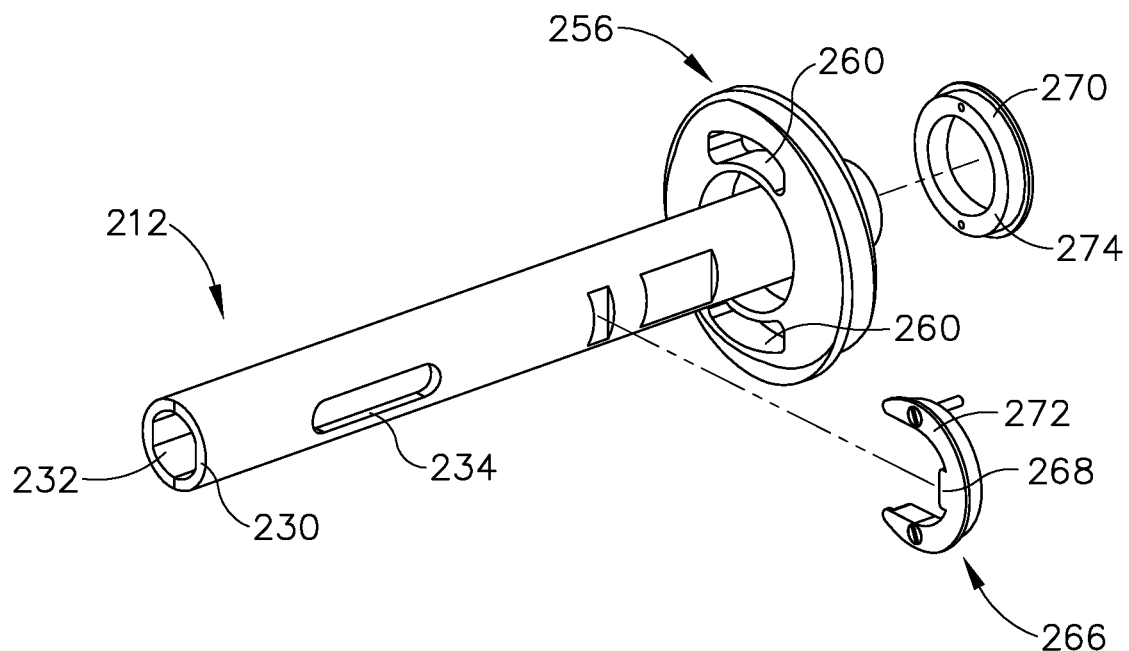
FIG. 19 depicts an exploded front perspective view of a lead screw of the shaft control assembly of FIG. 14.
Figure 20:
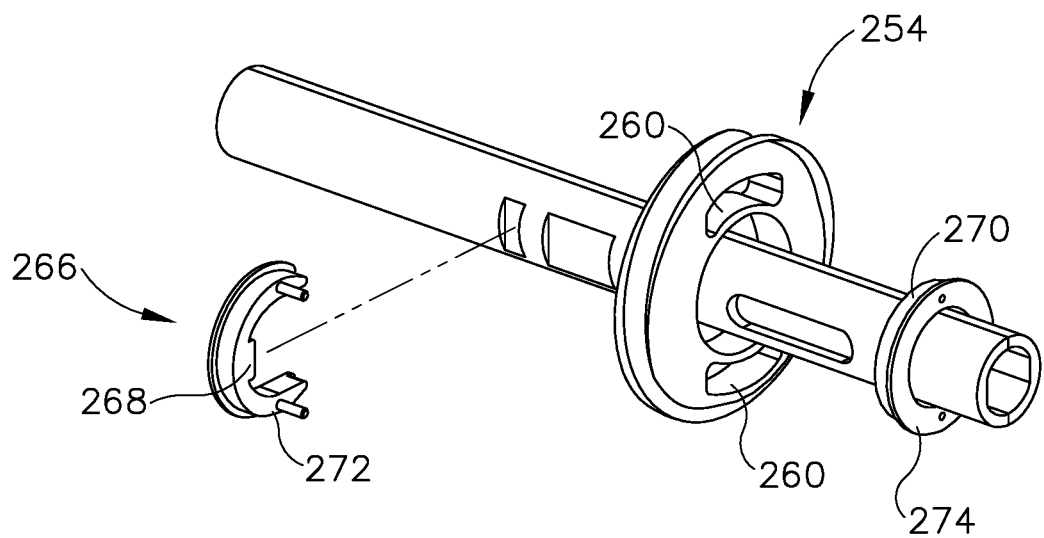
FIG. 20 depicts an exploded rear perspective view of another lead screw of the shaft control assembly of FIG. 14.

FIGS. 14-15 illustrate shaft control assembly (216) and a pair of translatable members (230, 232), which extend to respective articulation bands (140, 142) for directing articulation along shaft assembly (216) as discussed above with respect to shaft assembly (30) (see FIG. 3). Translatable members (230, 232) differ from translatable members (161, 162) by at least having a pair of longitudinal slots (234, 236) that extend laterally through translatable members (230, 232) to respectively receive pins (238, 240). Pins (238, 240) extend through pin holes (242) in rotation control knob (224) such that pins (238, 240) secure rotation control knob (224) to translatable members (230, 232). Thus, as the operator selectively rotates rotation control knob (224), rotation control knob (224) causes rotation of translatable members (230, 232) and the other relevant portions of shaft assembly (212) as discussed above with respect to surgical instrument (10) (see FIG. 1). Additional components of rotation control assembly (220) will be discussed below in further detail.

Transmission assembly (226) is configured to transmit selective movement, such as rotational input by the operator via articulation control knob (222), to shaft assembly (212) for articulating articulation section (130) (see FIG. 11). Transmission assembly (226) includes a drive gear in the form of a bevel drive gear (246) and a bevel driven gear (248) as shown in FIGS. 15-18. In the present example, bevel drive gear (246) is secured to a rigid drive shaft (250), which extends along the transverse axis for selective rotation by the operator. Bevel drive gear (246), in turn, also rotates about the transverse axis. Bevel drive gear (246) engages with bevel driven gear (248), such that the respective pluralities of teeth on each gear (246, 248) mesh for transferring force therethrough. Bevel driven gear (248) is secured to a proximal end of a drum (252) such that each surrounds and is configured to rotate about the longitudinal axis. Bevel drive gear (246) and bevel driven gear (248) are configured to transfer the operator's rotation input about the transverse axis to rotation of drum (252) about the longitudinal axis. While the arrangement of bevel gears (246, 248) is configured to transfer this rotation 90 degrees for driving drum (252), it will be appreciated that alternative configurations may transfer such motion in alternative orientation for accommodating an alternatively positioned drum (252) and/or articulation control knob. Furthermore, articulation control knob (222) of the present example is generally shaped like a wheel having a plurality of angularly spaced projections extending radially outward therefrom. Such a wheel shape may be convenient for indicating rotation and articulation, and the plurality of projections may be configured to provide greater grip to the operator. However, it will be appreciated that articulation control knob (222) may be a variety of shapes and sizes for being gripped and rotated by the operator.

As shown in FIGS. 16-17 and FIGS. 19-20, articulation control assembly (216) further includes a frame (253), a proximal lead screw (254), and a distal lead screw (256) received within drum (252) for converting rotation of drum (252) to linear movement of lead screws (254, 256) to articulate articulation section (130) (see FIG. 11). In the present example, frame (253) has a pair of generally parallel and offset longitudinal tracks (258) received within respective recesses (260). Tracks (258) are configured to prevent rotation of proximal and distal lead screws (254, 256) while allowing for translation of lead screws (254, 256) along the longitudinal axis. Rotation of drum (216) will cause translation of lead screws (254, 256). More particularly, proximal lead screw (254) threadably engages proximal inner threads (262), while distal lead screw (256) threadably engages distal inner threads (264). Proximal and distal inner threads (262, 264) have opposing pitches relative to each other such that rotation of drum (252) will translate proximal and distal lead screws (254, 256) simultaneously in opposing directions.

In addition, lead screws (254, 256) are respectively connected to translatable members (230, 232) via respective tensioners (266). Each tensioner (266) has a key (268) engaged with the respective translatable member (230, 232) to direct movement of translatable members (230, 232) distally or proximally along the longitudinal axis via articulation control knob (222). However, each tensioner (266) also rotatably receives its respective lead screw (254, 256) within an annular channel (270) such that each lead screw (254, 256) and drum (252) are collectively configured to be rotated via rotation control knob (224) when rotating shaft assembly (212) without affecting articulation. By way of example, each tensioner (266) is defined by a C-shaped component (272), which includes key (268), and an annular component (274). In addition to the foregoing, drum (252), lead screws (254, 256), and other features articulation control assembly (218) may be constructed and operable in accordance with at least some of the teachings of U.S. patent application Ser. No. 14/688,663 entitled "Ultrasonic Surgical Instrument with Opposing Thread Drive for End Effector Articulation," filed on Apr. 16, 2015, issued as U.S. Pat. No. 10,342,567 on Jul. 9, 2019, the disclosure of which is incorporated by reference herein in its entirety.

Figure 21A:
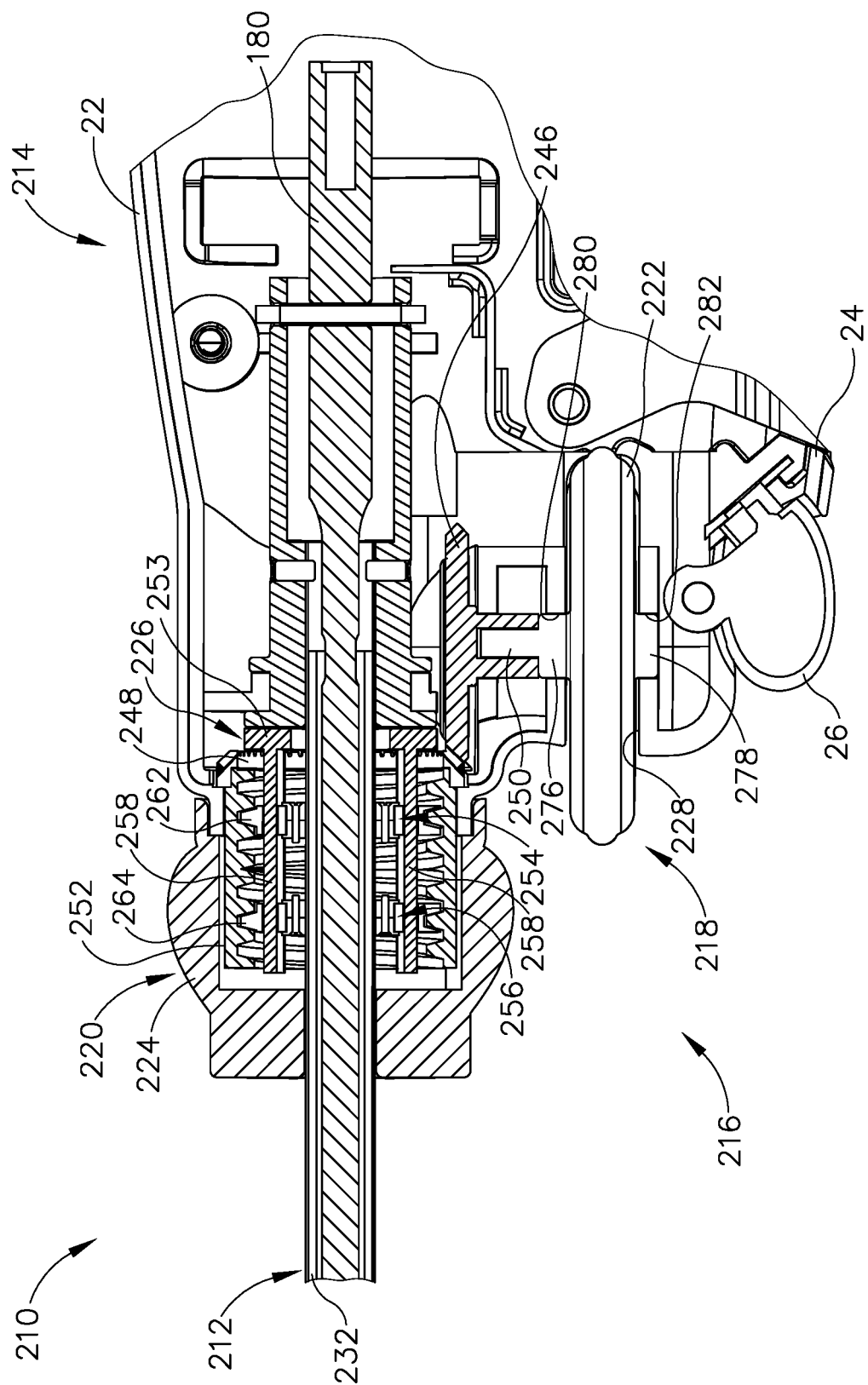
FIG. 21A depicts an enlarged cross-sectional view of the ultrasonic surgical instrument of FIG. 11 taken along section line 21A-21A of FIG. 12, with the shaft control assembly in a straight position such that a shaft assembly is in a straight configuration.

FIG. 21A shows the distal end portion of handle assembly (214) with articulation control assembly (218) in a straight position such that shaft assembly (212) is in a straight configuration. As discussed briefly above, knob slot (228) receives articulation control knob (222) such that a portion of articulation control knob (222) projects distally from knob slot (228). More particularly, articulation control knob (222) has an upper mount shaft (276) and an opposing lower mount shaft (278) extending in opposite directions along the transverse axis of articulation control knob (222). Upper and lower mount shafts (276, 278) are each rotatably received within upper and lower cylindrical mount channels (280, 282) of housing (22) for translatably affixing articulation control knob (222) relative to housing (22). Rigid drive shaft (250) extends upwardly from upper mount shaft (276) to bevel drive gear (246) for selectively driving transmission assembly (226).

On one hand, articulation control knob (222) may be selectively rotated by the operator to articulate articulation section (130) (see FIG. 11) through transmission assembly (226). On the other hand, transmission assembly (226) is configured to inhibit inadvertent articulation of articulation control assembly (218) by operatively locking transmission assembly (226) when articulation control knob (222) is not being rotated. In other words, rotation of articulation control knob (222) effectively unlocks articulation control assembly (218), otherwise transmission assembly (226) effectively locks articulation of articulation section (130) (see FIG. 11). By way of example, locking of transmission assembly (226) occurs because lead screws (254, 256) may not be forced via shaft assembly (212) to translate with sufficient mechanical advantage to rotate drum (252). However, rotating drum (252) via articulation control knob (222) unlocks movement with sufficient mechanical advantage over lead screws (254, 256) to translate lead screws (254, 256) and thereby articulate articulation section (130) (see FIG. 11).

Figure 21B:
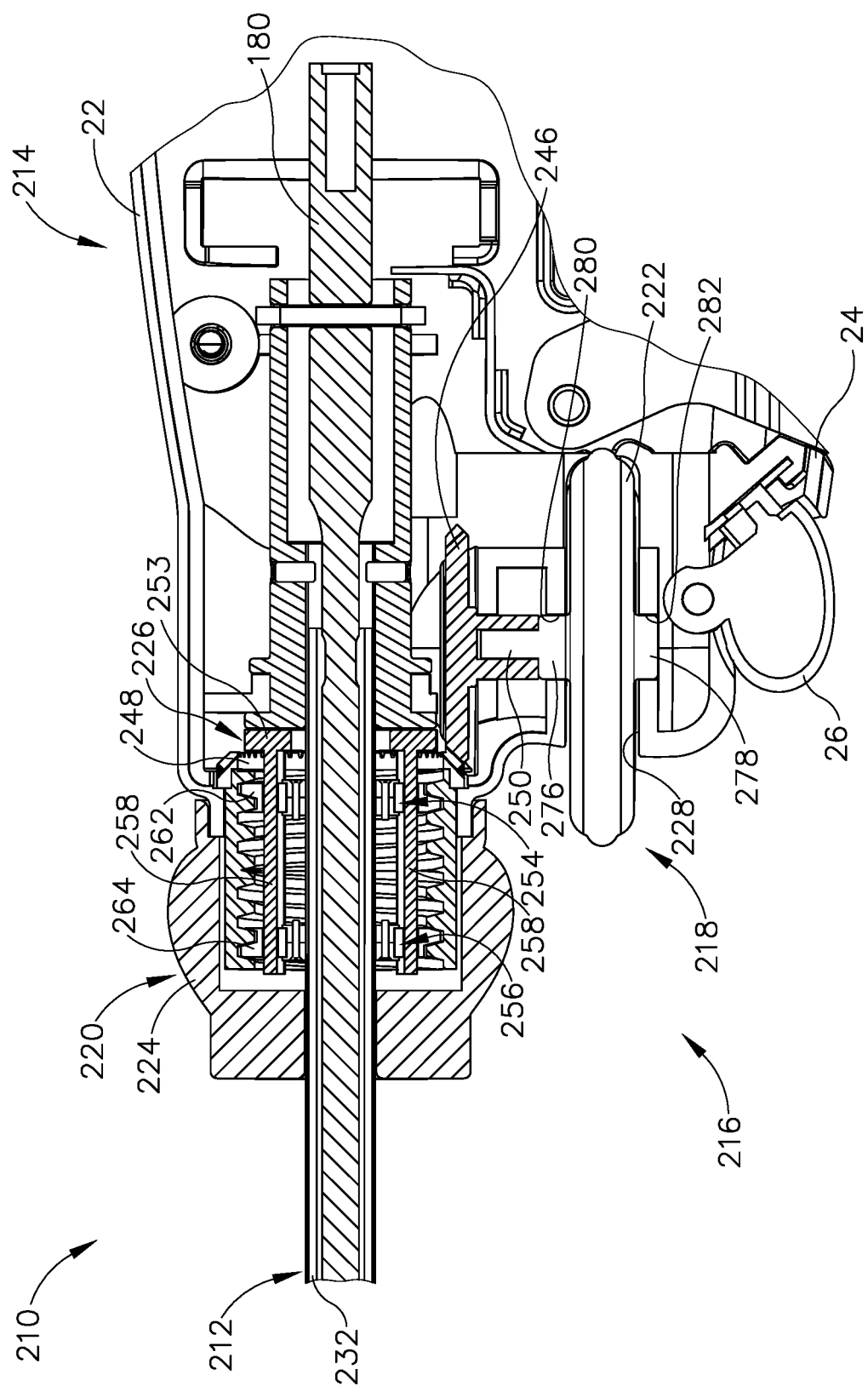
FIG. 21B depicts an enlarged cross-sectional view of the ultrasonic surgical instrument of FIG. 11 taken along section line 21A-21A of FIG. 12, with the shaft control assembly in a right position such that the shaft assembly is in a right articulated configuration.
Figure 21C:
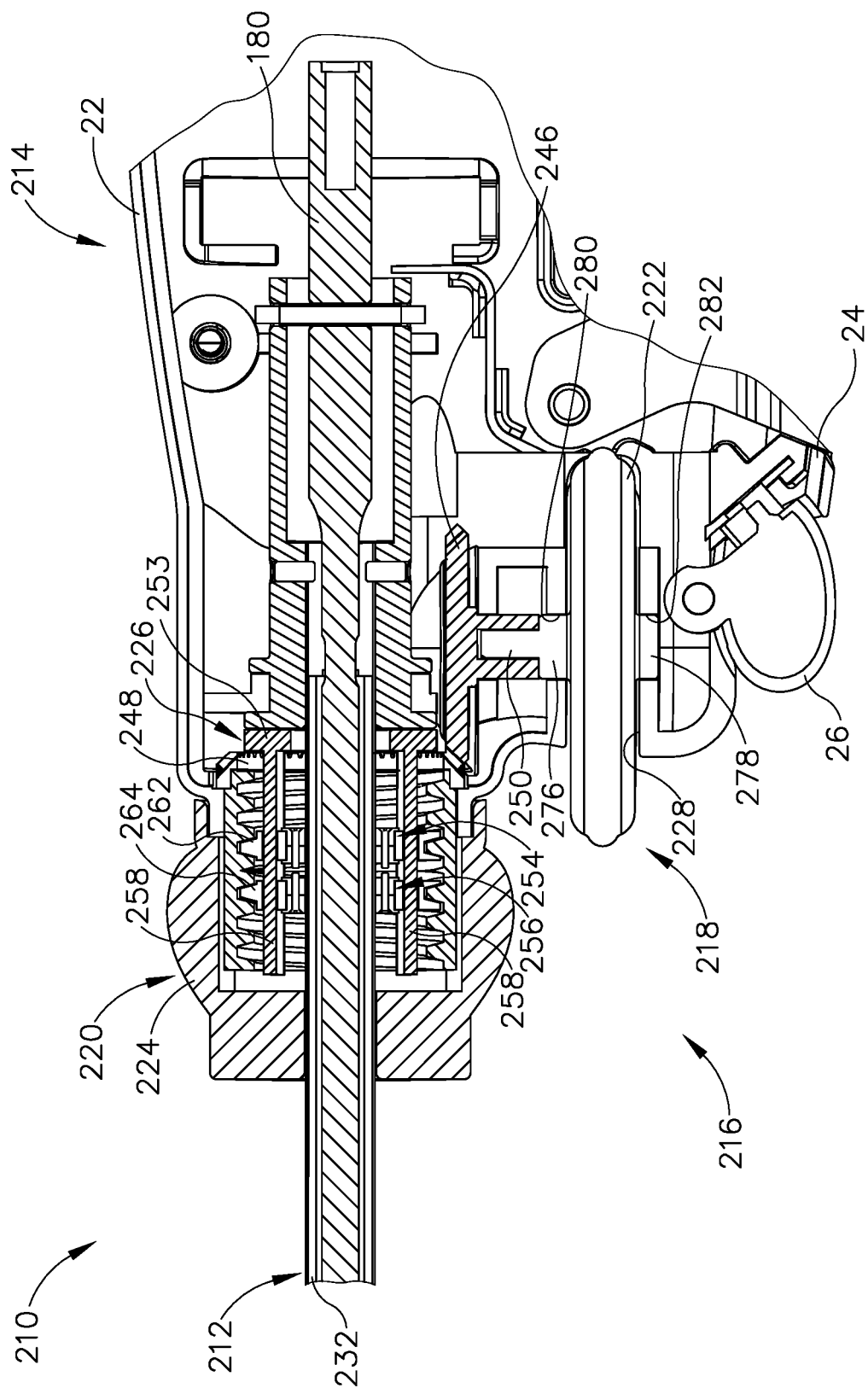
FIG. 21C depicts an enlarged cross-sectional view of the ultrasonic surgical instrument of FIG. 11 taken along section line 21A-21A of FIG. 12, with the shaft control assembly in a left position such that the shaft assembly is in a left articulated configuration.

In use, FIG. 21B and FIG. 21C respectively show articulation control assembly (218) in right and left positions with articulation section (130) (see FIG. 11) in right and left articulated configurations. From the straight position shown in FIG. 22A, the operator rotates articulation control knob (222) clockwise (when viewed by the operator from above) to similarly rotate bevel drive gear (246). Bevel drive gear (246) rotates bevel driven gear (248) and the rigidly attached drum (252). As drum (252) rotates counterclockwise (when viewed by the operator proximally positioned therefrom), distal lead screw (256) moves distally, whereas proximal lead screw (254) moves proximally. Distal and proximal lead screws (256, 254) thereby direct translatable members (230, 232) to articulate articulation section laterally to the right from the longitudinal axis for flexing shaft assembly (212).

Figure 22A:
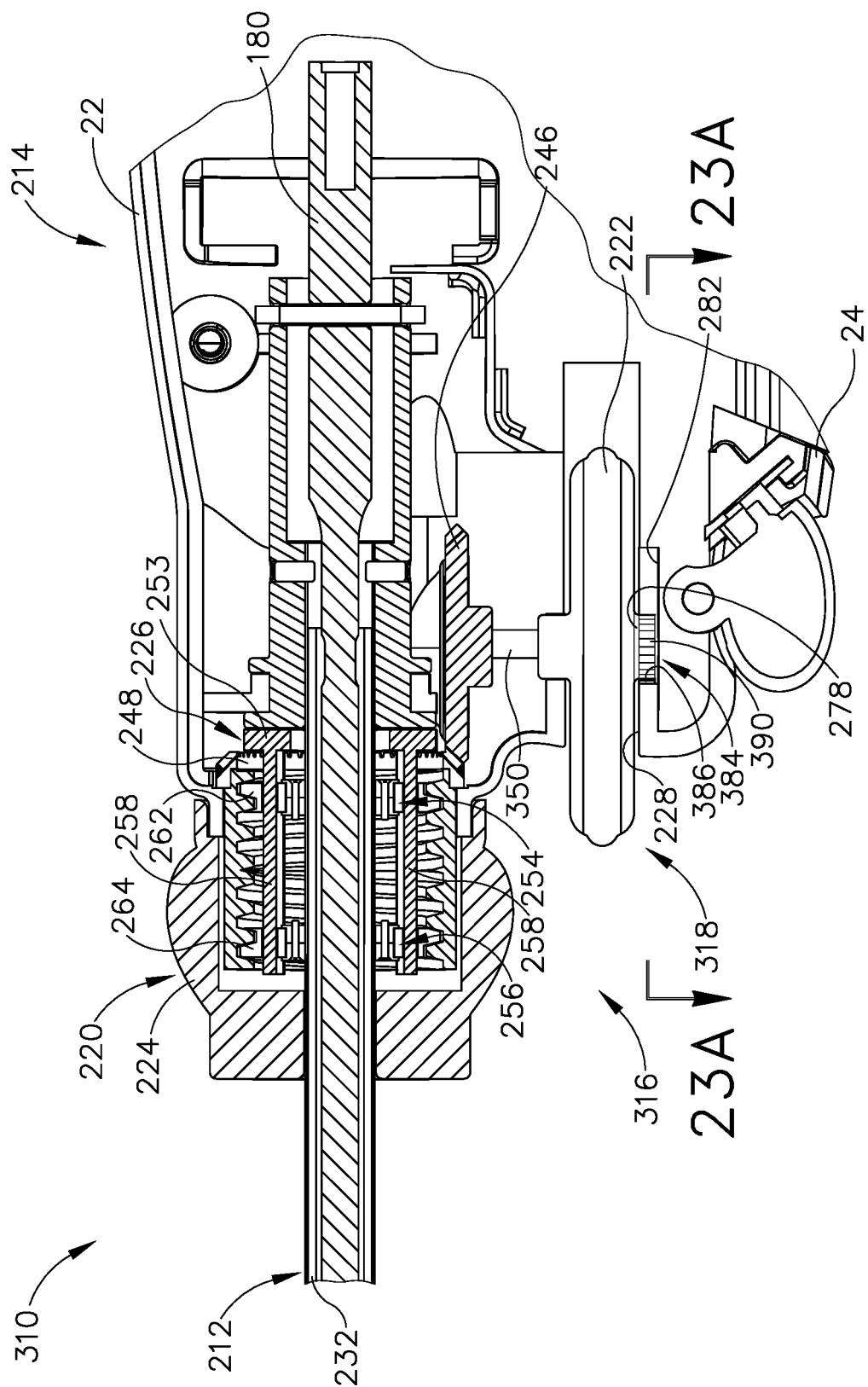
FIG. 22A depicts an enlarged side sectional view of a third exemplary ultrasonic surgical instrument having a shaft control assembly in a locked articulation position.

From the straight position shown in FIG. 22A, the operator rotates articulation control knob (222) counterclockwise (when viewed by the operator from above) to similarly rotate bevel drive gear (246). Bevel drive gear (246) rotates bevel driven gear (248) and the rigidly attached drum (252). As drum (252) rotates clockwise (when viewed by the operator proximally positioned therefrom), distal lead screw (256) moves proximally, whereas proximal lead screw (254) moves distally. Distal and proximal lead screws (256, 254) thereby direct translatable members (230, 232) to articulate articulation section laterally to the left from the longitudinal axis for flexing shaft assembly (212).

B. Exemplary Articulation Control Assembly with a Locking Articulation Control Knob and a Resilient Drive Shaft FIGS. 22A-23B show a third ultrasonic surgical instrument (310) having shaft assembly (212), handle assembly (214), and a shaft control assembly (316). Shaft control assembly (316) includes rotation control assembly (220) as discussed above, and an articulation control assembly (318). Generally, articulation control assembly (318) has transmission assembly (226) with bevel drive and driven gears (248, 250) similar to articulation control assembly (218), but also includes an articulation control lock (384), which directly secures articulation control knob (222) relative to housing (22) for inhibiting articulation of articulation section (130) (see FIG. 11).

To this end, housing (22) has an elongated lower mount channel (382) and articulation control assembly (318) has a resilient drive shaft (350) that is biased toward a locked articulation state to be selectively moved to an unlocked articulation state. As described herein, the locked articulation state inhibits articulation, whereas the unlocked articulation state allows articulation. In the present example, articulation control lock (384) includes a plurality of channel teeth (386) extending proximally from a distal channel end (388) and a plurality of shaft teeth (390) radially projecting from lower mount shaft (278). Channel and shaft teeth (386, 390) engage each other and overlap via resilient drive shaft (350), such as by interlocking, to inhibit relative rotation therebetween in the locked articulation state shown in FIGS. 22A and 23A. Specifically, resilient drive shaft (350) biases shaft teeth (390) distally to engage channel teeth (386), because articulation control knob (222) is effectively cantilevered downwardly from bevel drive gear (248).

Figure 22B:
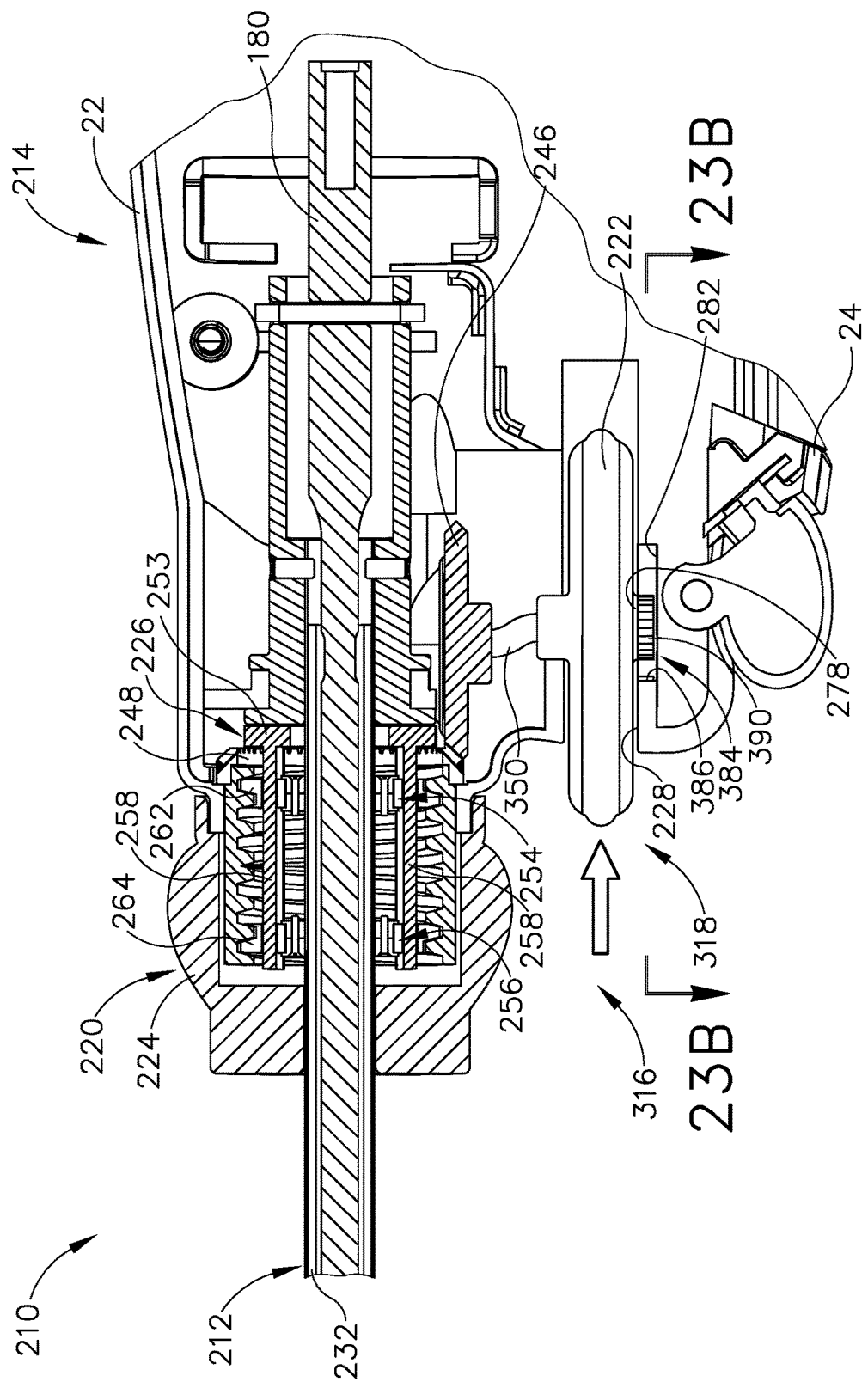
FIG. 22B depicts an enlarged side sectional view of the surgical instrument of FIG. 22A, with the shaft control assembly in an unlocked articulation position.
Figure 23A:
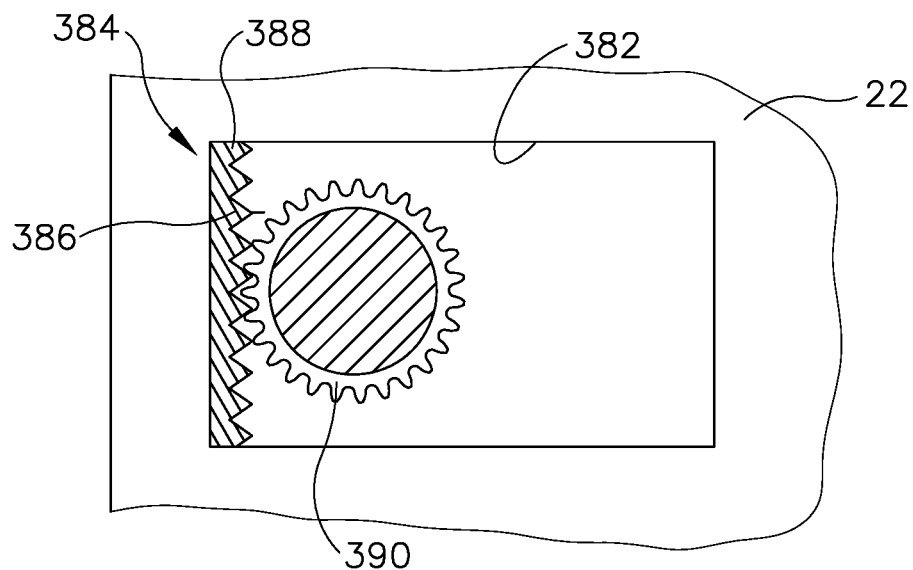
FIG. 23A depicts an enlarged cross-sectional view of the surgical instrument of FIG. 22A, taken along section line 23A-23A of FIG. 22A, with the shaft control assembly in the locked articulation position.
Figure 23B:
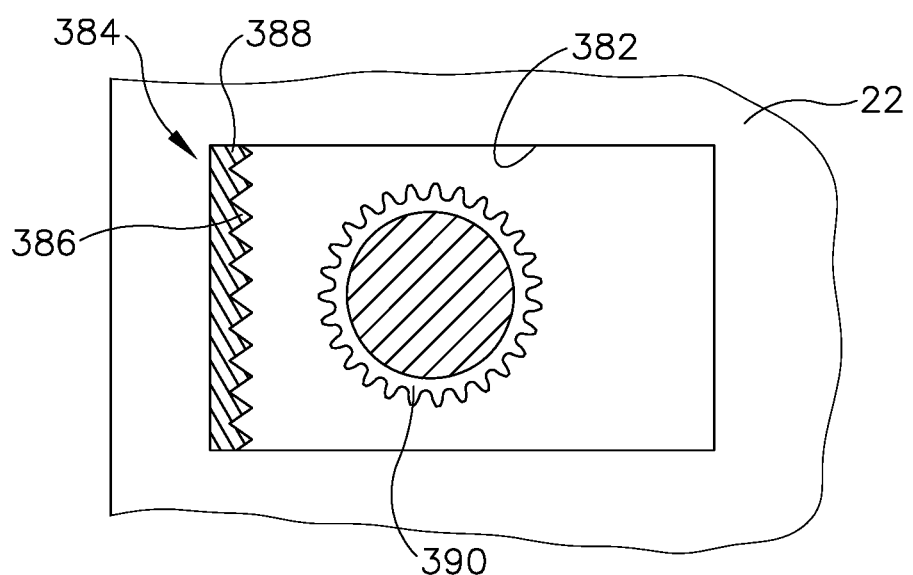
FIG. 23B depicts an enlarged cross-sectional view of the surgical instrument of FIG. 22B, taken along section line 23B-23B of FIG. 22B, with the shaft control assembly in the unlocked articulation position.

In use, the operator urges articulation control knob (222) proximally such that channel and shaft teeth (386, 390) disengage to allow relative rotation for flexing shaft assembly (212) as discussed above in greater detail. FIGS. 22B and 23B show shaft teeth (390) moved proximally in the unlocked articulation state. While exemplary teeth (390, 386), resilient drive shaft (350), and elongated lower mount channel (382) cooperate to define one exemplary articulation control lock (384), alternative locking features may cooperate to directly lock rotation of articulation control knob (222) relative to housing (22). Thus, the invention described herein is not intended to be unnecessarily limited to exemplary articulation control lock (384).

Figure 24A:
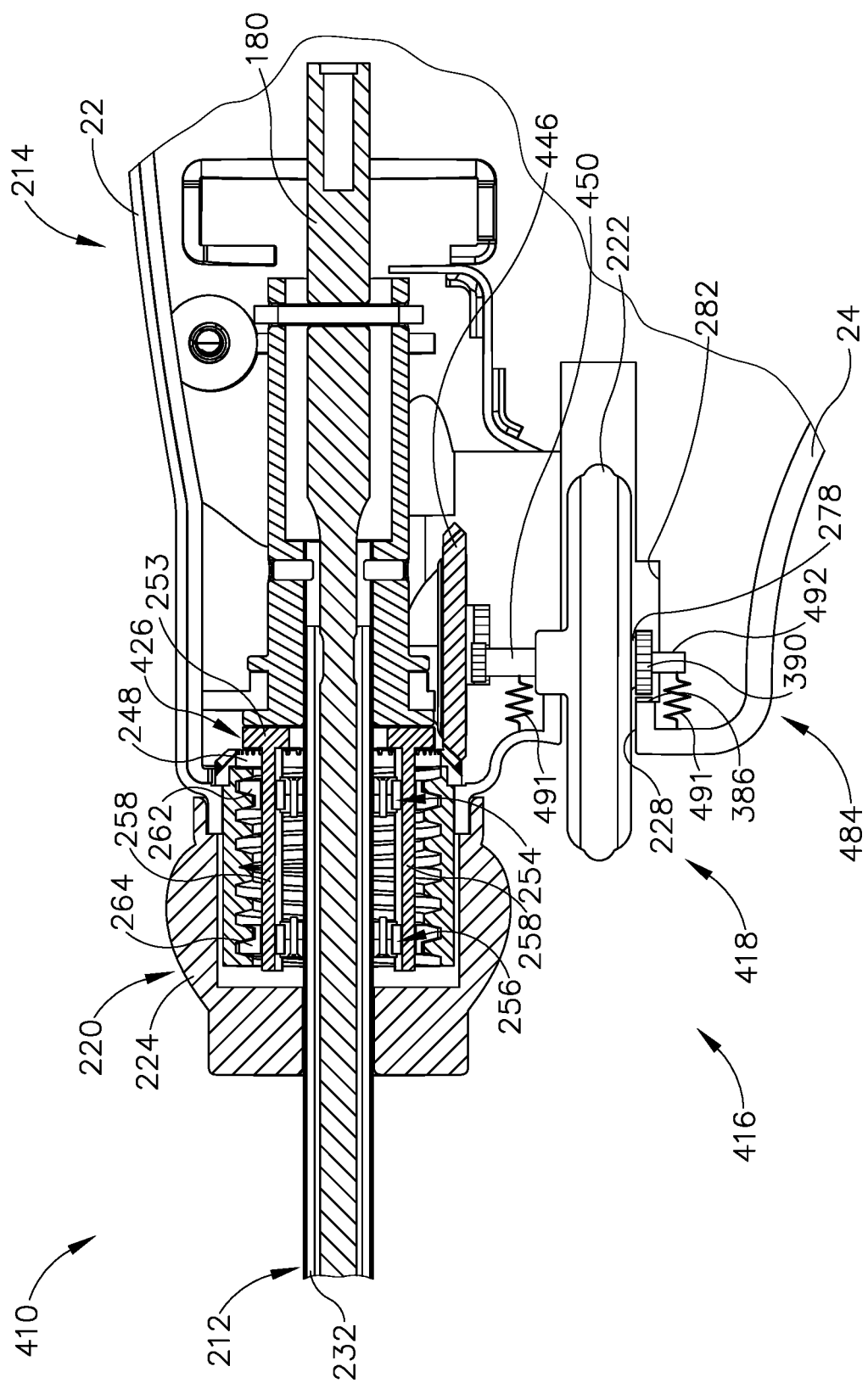
FIG. 24A depicts an enlarged side sectional view of a fourth exemplary ultrasonic surgical instrument having a shaft control assembly in a locked articulation position.
Figure 24B:
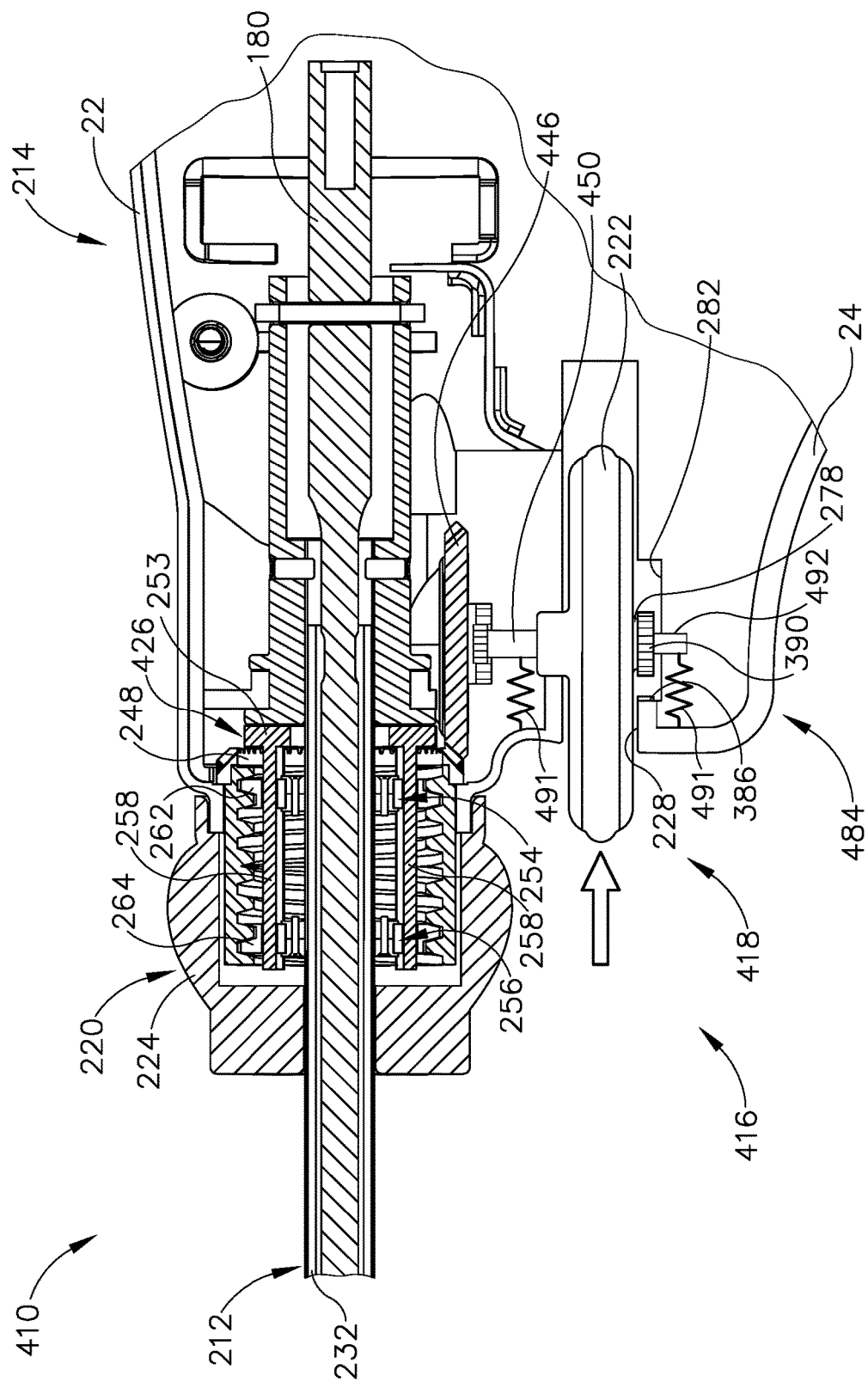
FIG. 24B depicts an enlarged side sectional view of the surgical instrument of FIG. 24A, with the shaft control assembly in an unlocked articulation position.
Figure 25:
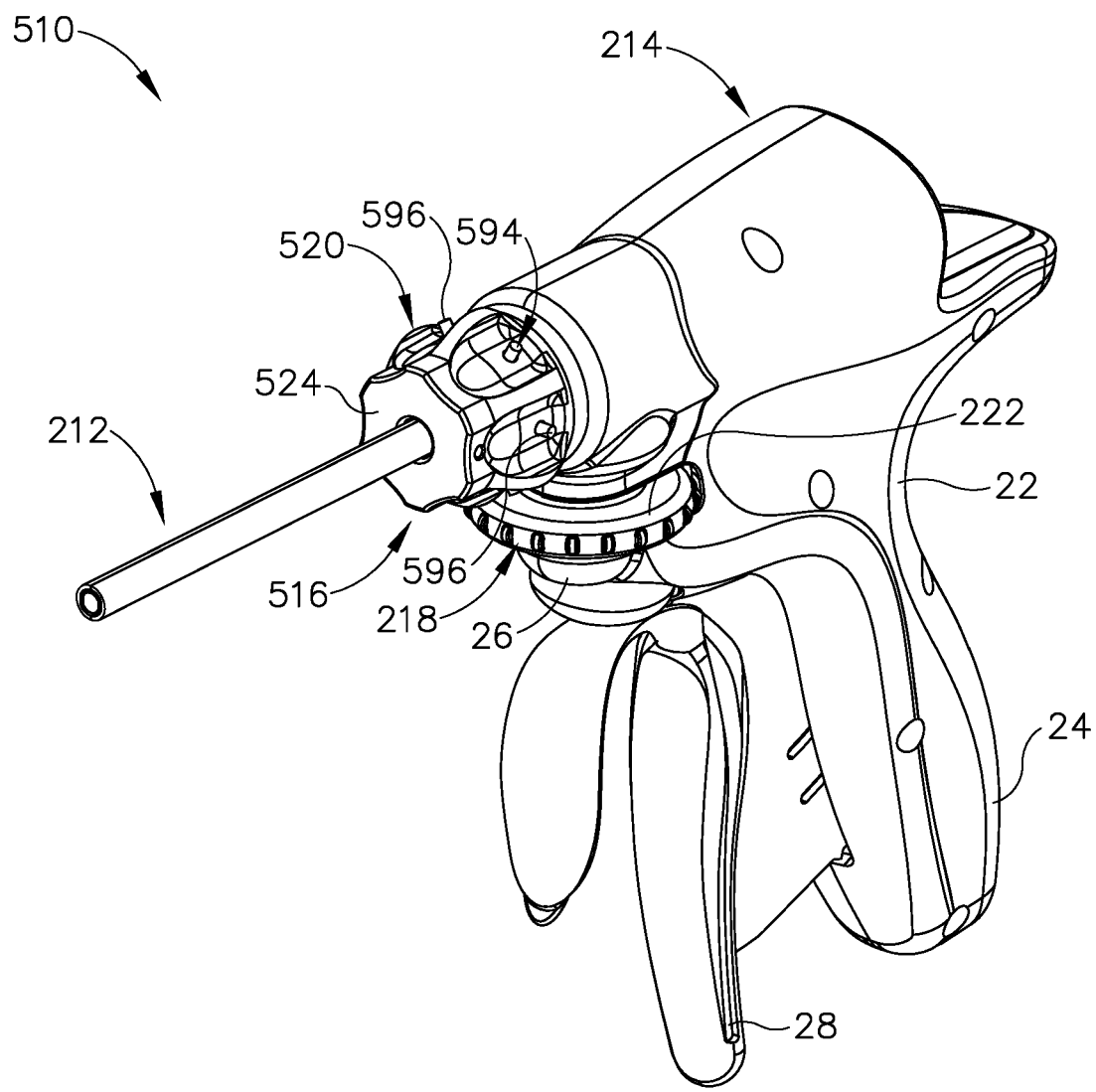
FIG. 25 depicts a front perspective view of a fifth exemplary ultrasonic surgical instrument having a shaft control assembly with a lockable rotation control knob.

C. Exemplary Articulation Control Assembly with a Locking Articulation Control Knob and a Resiliently Mounted Drive Shaft FIGS. 24A-24B show a fourth exemplary surgical instrument (410) having shaft assembly (212), handle assembly (214), and a shaft control assembly (416). Shaft control assembly (416) has rotation control assembly (220) as discussed above, and an articulation control assembly (418). Articulation control assembly (418) has a transmission assembly (426) similar to transmission assembly (226) (see FIG. 21A), but with a bevel drive gear (446) and a rigid drive shaft (450) configured to selectively engage and disengage as discussed below for locking and unlocking an articulation control lock (484). In addition, articulation control lock (484) has channel and shaft teeth (386, 390) biased toward each other for selectively moving articulation control knob (222) from a locked articulation state to an unlocked articulation state. In the present example, articulation control knob (222) is biased via a plurality of springs (491). However, it will be appreciated that alternative biasing elements may instead be used.

A lower rotation support (492) extends transversely below articulation control knob (222), whereas drive shaft (450) extends transversely upwardly from articulation control knob (222). Each of lower rotation support (492) and drive shaft (450) are distally biased such that articulation control knob (222) extending therebetween is translatably pulled distally with channel and shaft teeth (386, 390) engaged in the locked articulation state. In use, the operator urges articulation control knob (222) proximally such that channel and shaft teeth (386, 390) disengage to allow relative rotation for flexing shaft assembly (212) as discussed above in greater detail. Drive shaft (450) also moves proximally to operatively engage bevel drive gear (446) as shown in FIG. 24B for aligning bevel drive gear (446) and articulation control knob (222) with the transverse axis for being rotated. While exemplary teeth (390, 386), rigid drive shaft (450), elongated lower mount channel (382), and lower rotation support (492) cooperate to define one exemplary articulation control lock (484), alternative locking features may cooperate to directly lock rotation of articulation control knob (222) relative to housing (22). Thus, the invention described herein is not intended to be unnecessarily limited to exemplary articulation control lock (484).

D. Exemplary Rotation Control Assembly with a Locking Rotation Control Knob

FIGS. 25-30B show a fifth exemplary ultrasonic surgical instrument (510) having shaft assembly (212) and handle assembly (214) generally as discussed above. In addition, surgical instrument (510) has a shaft control assembly (516) with a locking rotation control assembly (520) that is configured to directly lock a rotation control knob (524) relative to housing (22) for inhibiting rotation of shaft assembly (212). A rotation control lock (594) is configured to be transitioned between a locked rotation state for inhibiting rotation of shaft assembly (212) and an unlocked rotation state for allowing the operator to selectively rotate shaft assembly (212).

Figure 26:
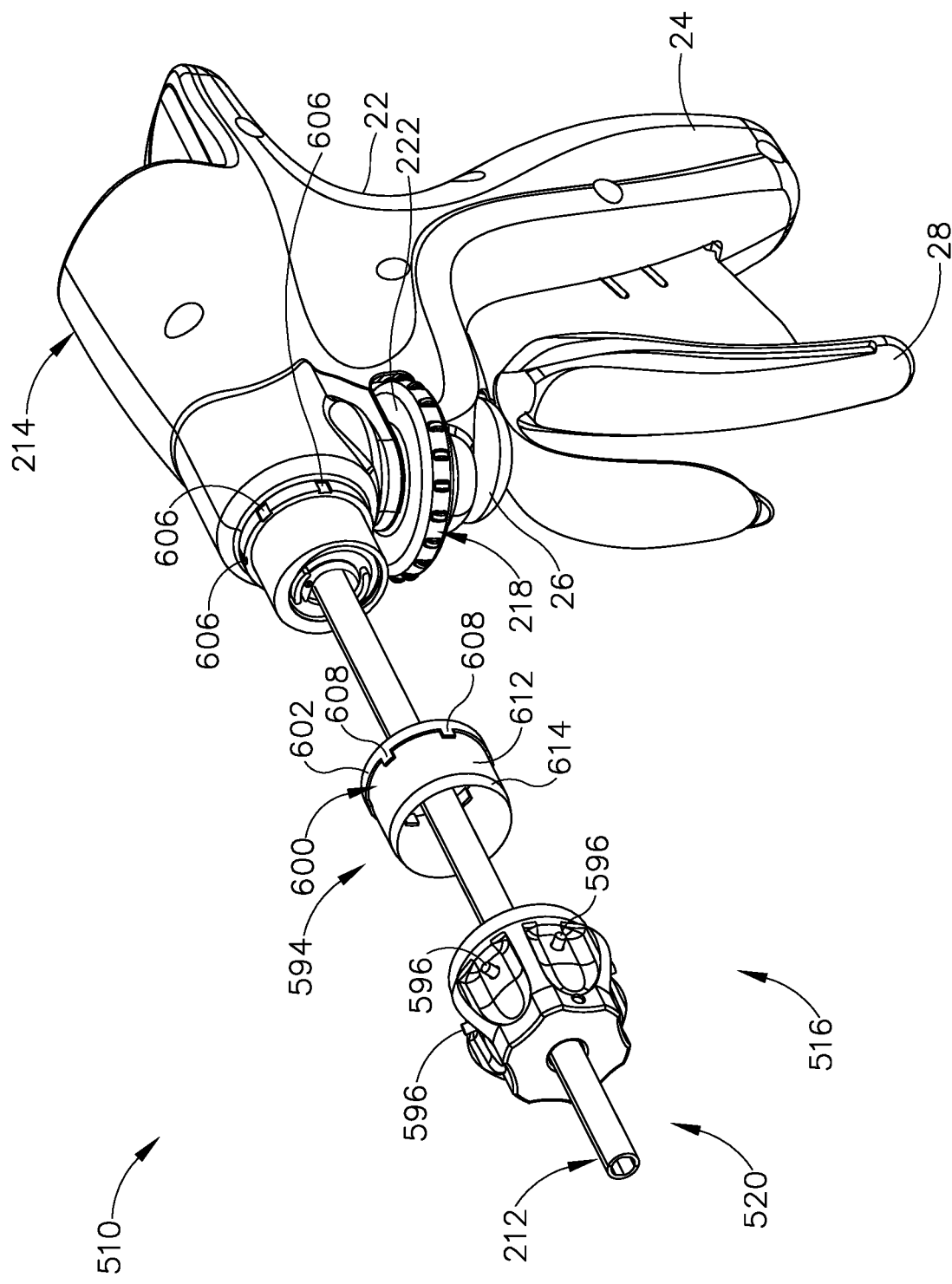
FIG. 26 depicts a partially exploded front perspective view of the surgical instrument of FIG. 25.
Figure 27:
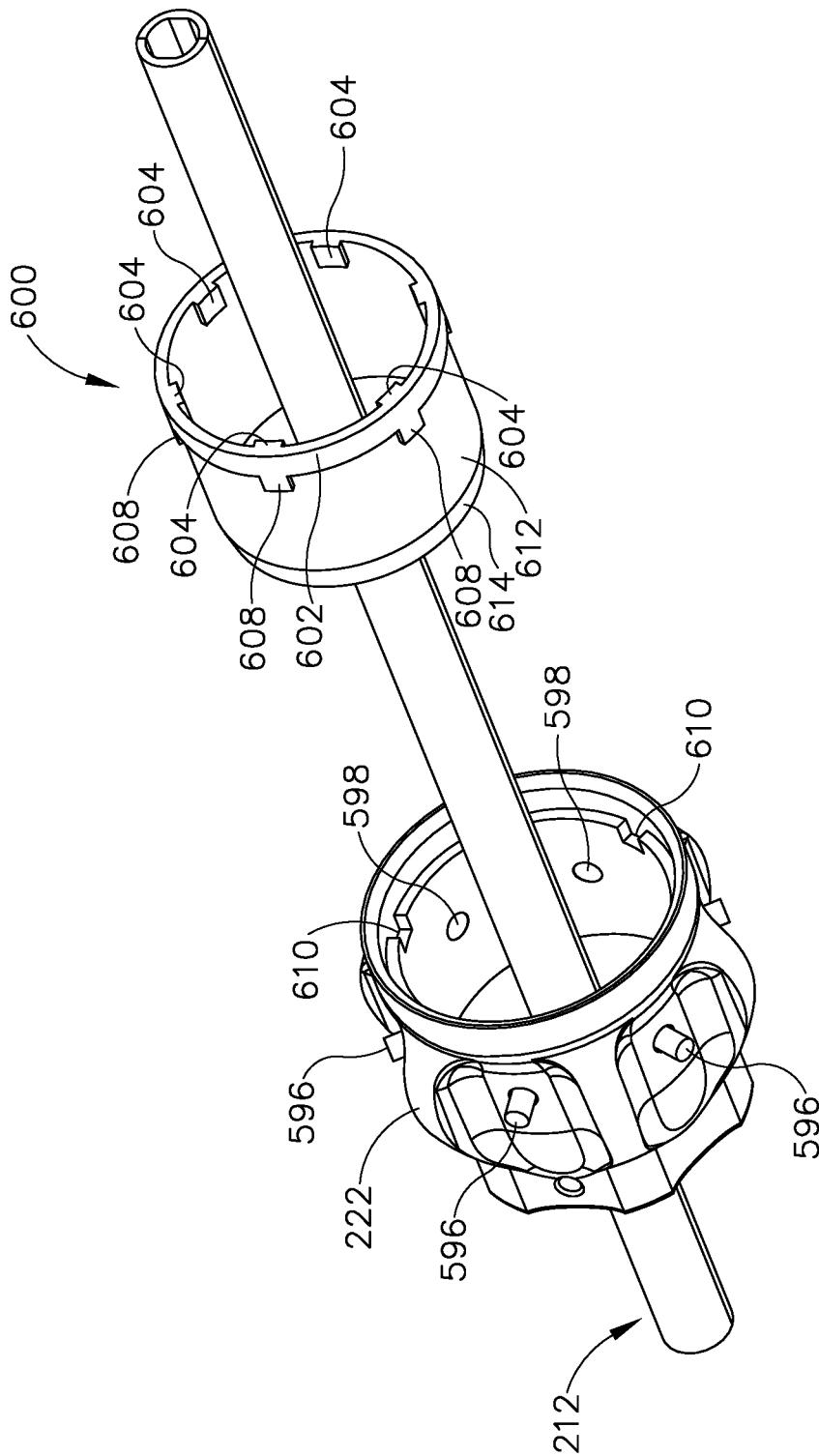
FIG. 27 depicts an enlarged partially exploded rear perspective view of the lockable rotation control knob of FIG. 25.

As shown in FIGS. 26-27, rotation control lock (594) includes a plurality of buttons (596) angularly positioned on the rotation control knob (524) about the longitudinal axis and extending radially through rotation control knob (524). Each button (596) is received within a respective button bore (598) and is configured to slide therethrough for being depressed by the operator. In the present example, rotation control lock (594) has six buttons (596) and six respective button bores (598) positioned equiangularly about rotation control knob (524). The operator may thus easily access at least one of the buttons (596) for manipulating rotation control lock (594) between locked and unlocked rotation states. While exemplary rotation control lock (594) includes buttons (596) supported within rotation control knob (524), it will be appreciated that other forms of actuation members, such as alternative buttons or switches, may instead be used. Moreover, these actuation members may be alternatively sized and/or positioned relative to shaft assembly (212) and handle assembly (214) for inhibiting rotation of shaft assembly (212) relative to handle assembly.

Rotation control lock (594) further includes a rotation lock member in the form of a rotation lock ring (600). Generally, rotation lock ring (600) movably extends between housing (22) and rotation control knob (524) to selectively fix rotation control knob (524) relative to housing (22) for inhibiting rotation therebetween. Rotation lock ring (600) extends about the longitudinal axis and is concentrically nested between rotation control knob (524) and shaft assembly (214). In the present example, rotation lock ring (600) is rotatably secured to housing (22) and is selectively engaged with rotation control knob (524) such that depression of at least one of the buttons (596) disengages rotation lock ring (600) from rotation control knob (524) to allow for relative rotation.

Rotation lock ring (600) includes a proximally positioned annular flange (602) captured between rotation control knob (524) and housing (22), while also being configured to translate between a distal locked position and a proximal unlocked position for the respective locked and unlocked rotation states. Regardless of position, rotation lock ring (600) is fixed to housing (22) by a plurality of angularly positioned and inwardly extending inner key tabs (604). Each inner key tab (604) is received within an outer key channel (606) similarly positioned about the longitudinal axis and defined by a distal end of housing (22). Inner key tabs (604) and outer key channels (606) interlock to inhibit rotation of rotation lock ring (600) relative to housing (22).

Figure 28:
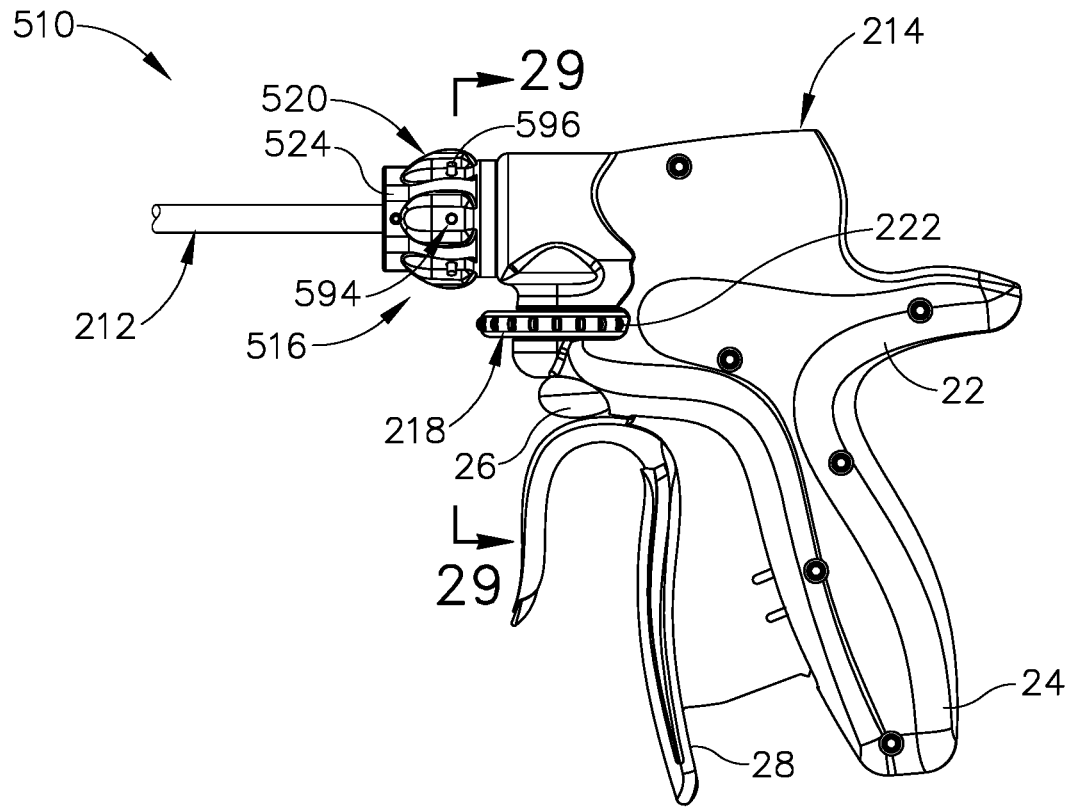
FIG. 28 depicts a side elevational view of the surgical instrument of FIG. 25.
Figure 29:
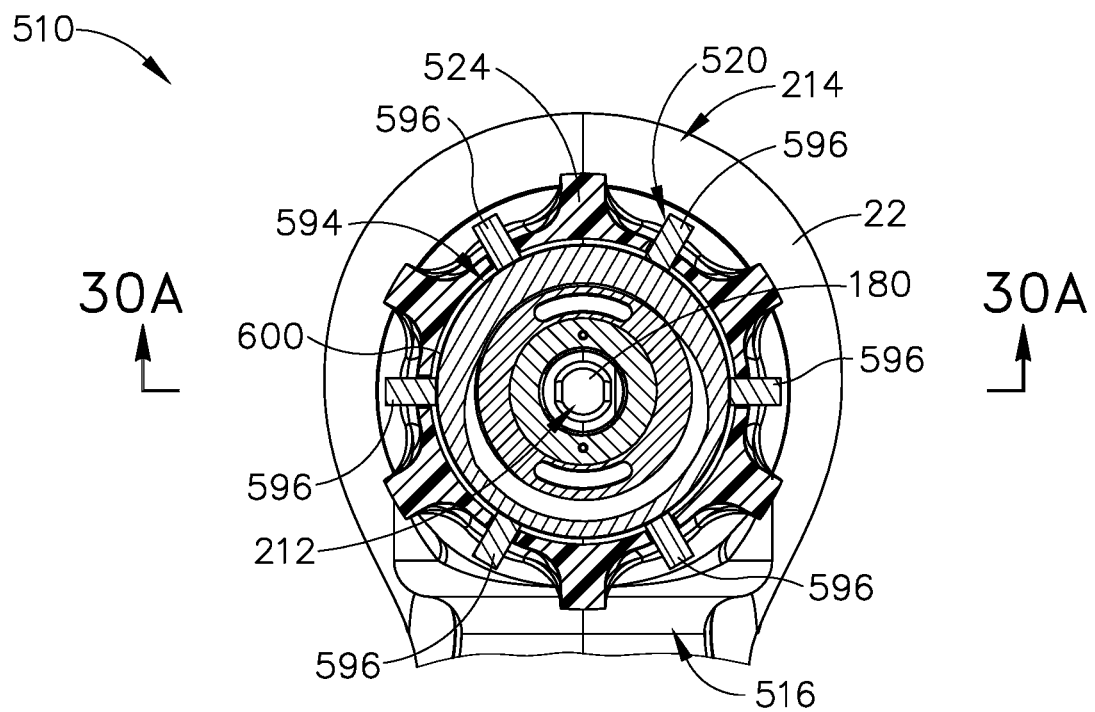
FIG. 29 depicts an enlarged cross-sectional view of the surgical instrument of FIG. 25 taken along section line 29-29 of FIG. 28.

As shown in FIGS. 27-29, rotation lock ring (600) further includes a plurality of distal key tabs (608) that extend distally from annular flange (602) toward rotation control knob (524) for releasable engagement therewith. More particularly, each distal key tab (608) is received within a respective proximal key channel (610) defined within rotation control knob (524). Distal key tabs (608) and proximal key channels (610) selectively interlock to inhibit rotation of rotation control knob (524) relative to rotation lock ring (600) relative to housing (22) when the rotation lock ring (600) is in the distal locked position. In contrast, distal key tabs (608) withdraw from proximal key channels (610) when rotation lock ring (600) is in the proximal unlocked position for being rotatably manipulated by the operator. In some versions, rotation lock ring (600) is biased toward the distal locked position via a biasing member, such as compression spring (not shown), positioned between housing (22) and rotation lock ring (600). However, it will be appreciated that alternative biasing members may be used for biasing rotation lock ring (600).

Figure 30A:
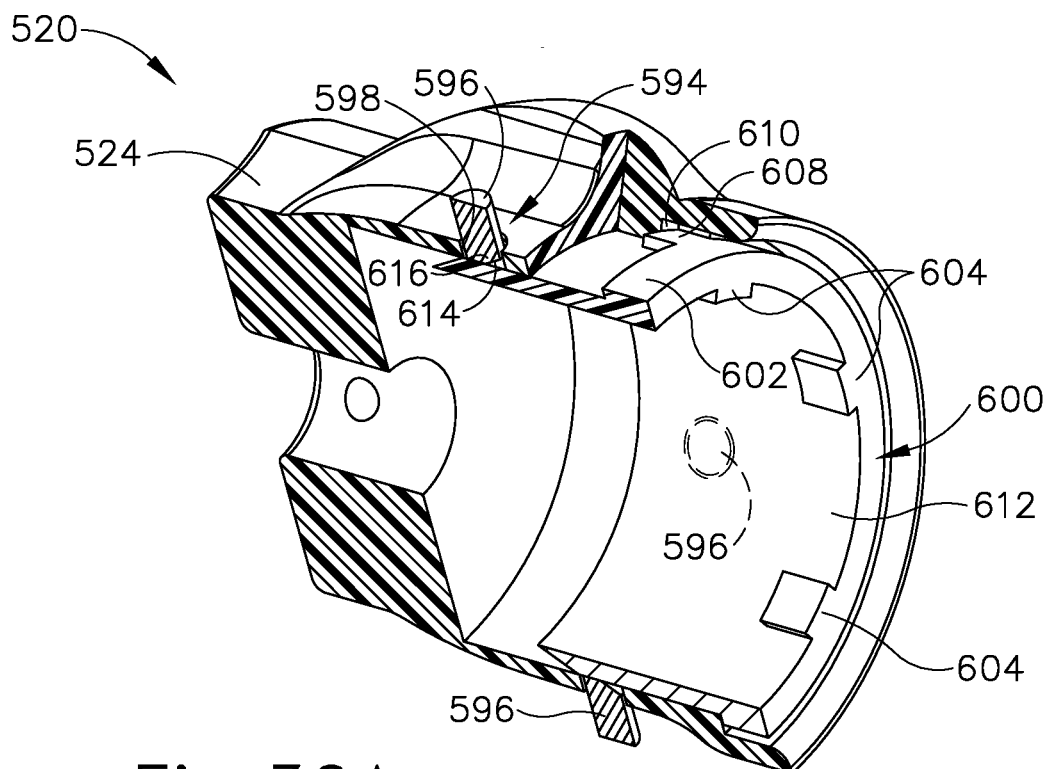
FIG. 30A depicts a rear perspective sectional view of the lockable rotation control knob of FIG. 25, taken along section line 30A-30A of FIG. 29, with the lockable rotation control knob in a locked rotation position.
Figure 30B:
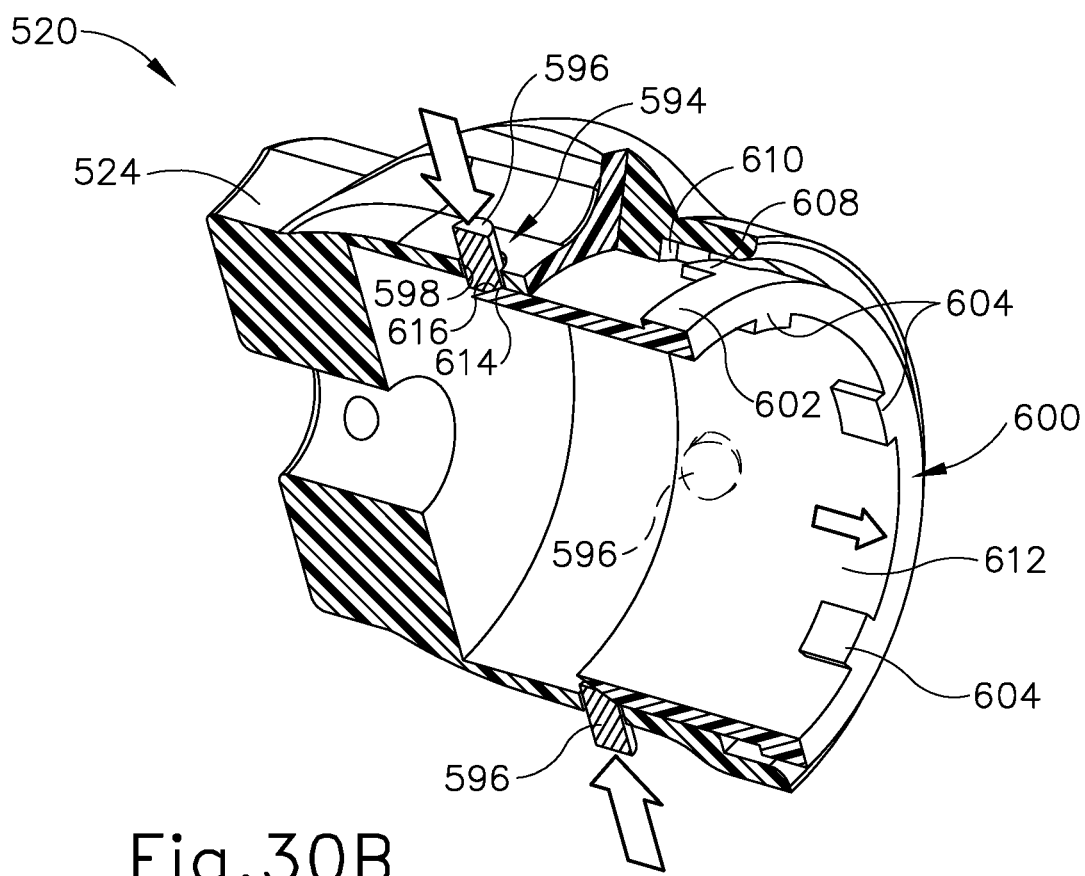
FIG. 30B depicts a rear perspective sectional view of the lockable rotation control knob of FIG. 25, taken along section line 30A-30A of FIG. 29, with the lockable rotation control knob in an unlocked rotation position.

As shown in FIGS. 29-30B, each button (596) is configured to direct rotation lock ring from the distal locked position to the proximal unlocked position. By way of example, rotation lock ring (600) has an annular extension (612) distally projecting from annular flange (602) toward buttons (596). Annular extension (612) has a distal annular cam surface (614) tapering inwardly toward a distal end thereof, while each button (596) has a button cam surface (616) that tapers radially inwardly toward a distal end thereof. FIG. 30A shows rotation lock ring (600) in the distal locked position with the distal annular cam surface (614) engaged with the button cam surface (616).

In use, depressing button (596) radially inwardly as shown in FIG. 30B causes button cam surface (516) to slide against distal annular cam surface (614) and direct distal annular cam surface (614) proximally until rotation lock ring is in the proximal unlocked position. The operator thus manipulates rotation control lock (594) from the locked rotation state to the unlocked rotation state for selectively rotating shaft assembly (212). After rotating shaft assembly (212) to a desirable position, the operator releases button (596), causing the spring (not shown) to direct rotation lock ring (600) back to the distal locked position, which urges buttons (596) radially outwardly for locking rotation control knob (514).

Figure 31A:
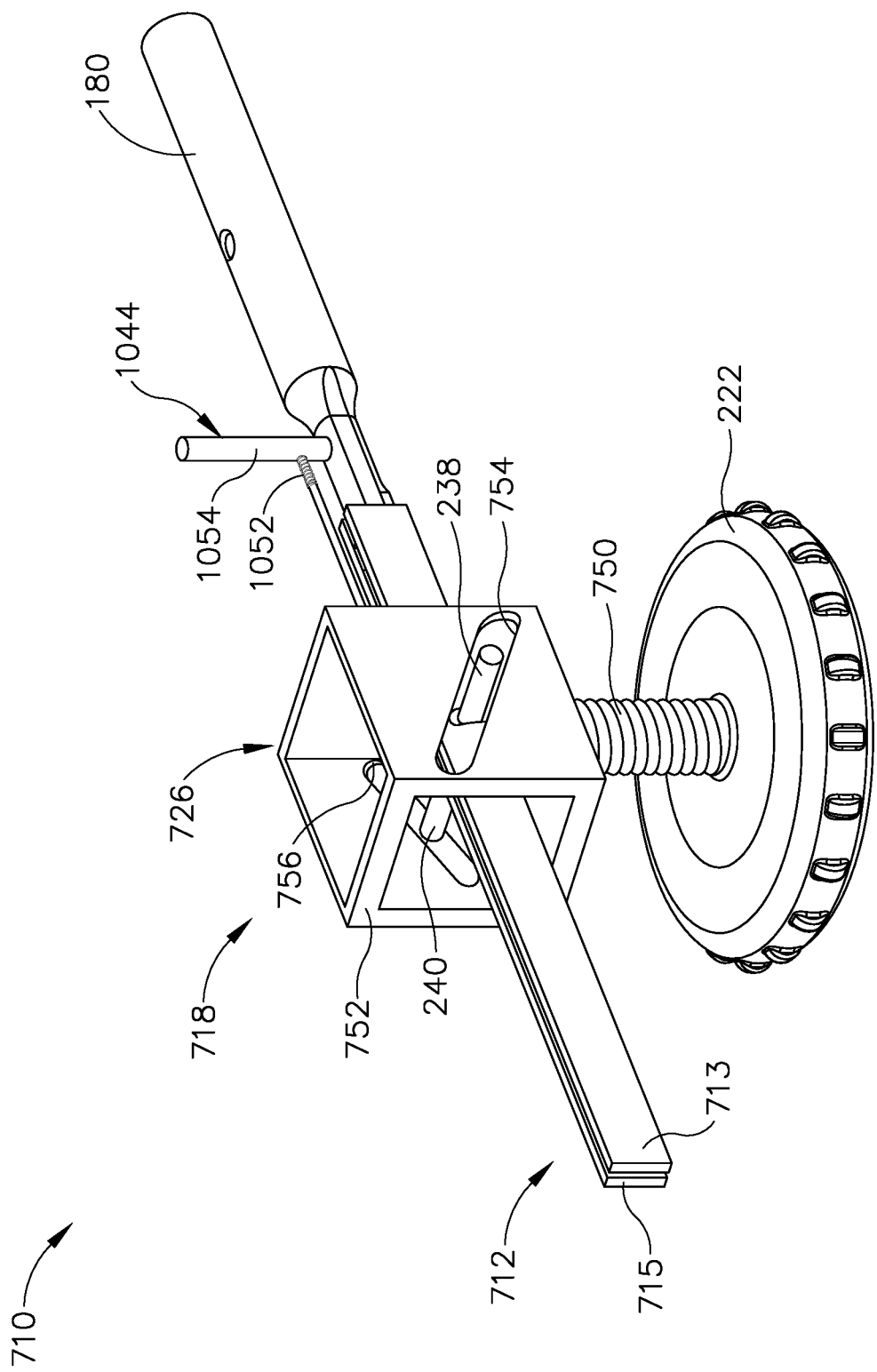
FIG. 31A depicts an enlarged front perspective view of a sixth exemplary ultrasonic surgical instrument with a shaft control assembly in a straight position such that a shaft assembly is in a straight configuration and having various components removed for clarity.
Figure 31B:
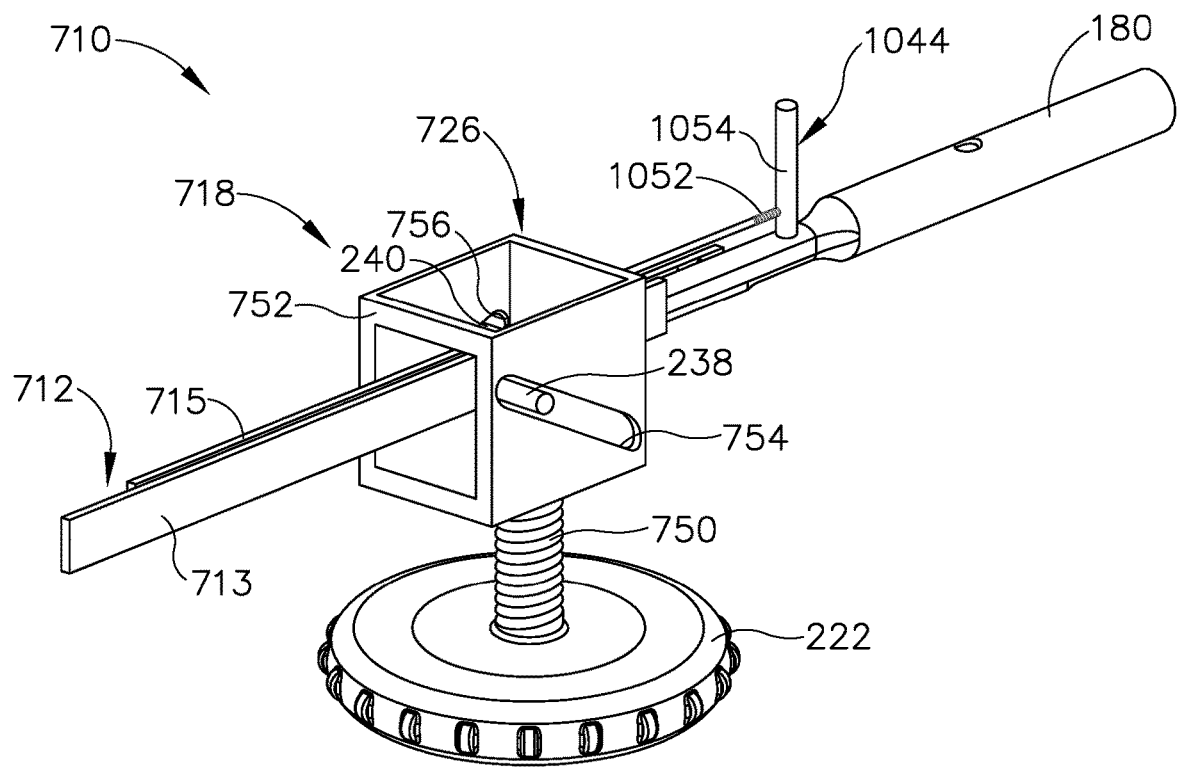
FIG. 31B depicts the front perspective view of the surgical instrument of FIG. 31A, with the shaft control assembly in a right position such that the shaft assembly is in a right articulated configuration.
Figure 31C:
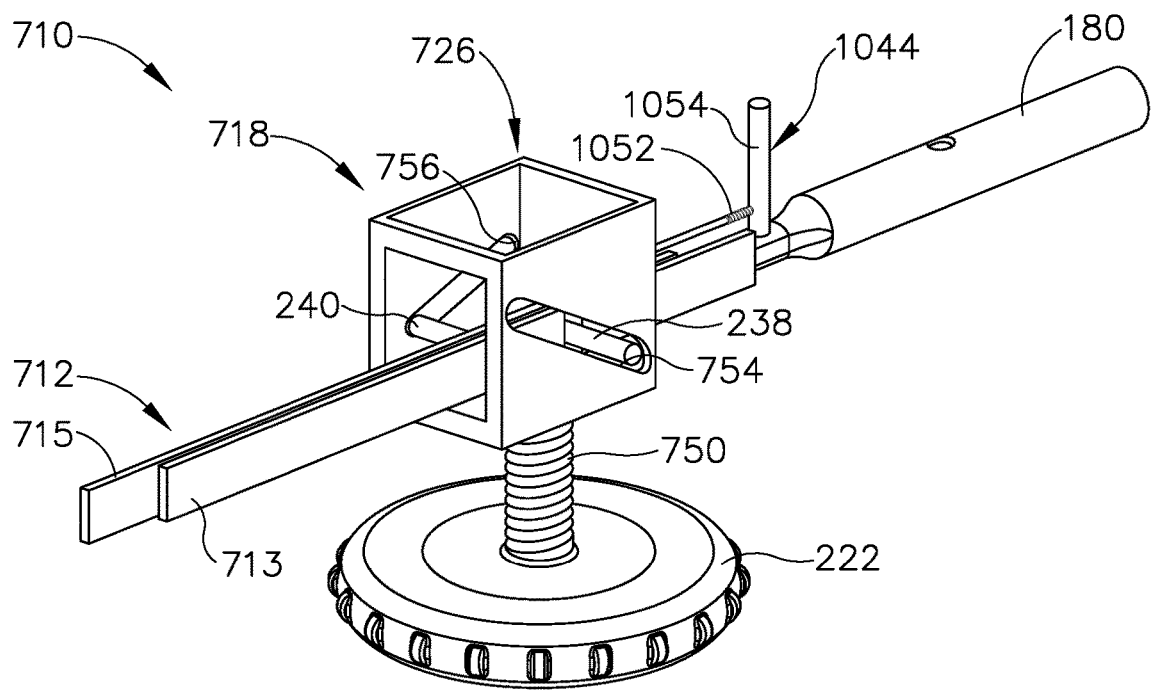
FIG. 31C depicts the front perspective view of the surgical instrument of FIG. 31A, with the shaft control assembly in a left position such that the shaft assembly is in a left articulated configuration.

E. Exemplary Transmission Assembly with Translating Articulation Body and Lock Switch for Variable Tension in Articulation Section FIGS. 31A-31C show a sixth embodiment of an ultrasonic surgical instrument (710) with various components removed to reveal a shaft assembly (712). Shaft assembly (712) includes elongated articulation bands (713, 715) similar to articulation bands (140, 142) (see FIG. 3), but that are longitudinally longer so as to extend into handle assembly (714) (see FIG. 32A). Acoustic waveguide (180) extends along shaft assembly (712) between elongated articulation bands (713, 715) for operative connection with end effector (40) (see FIG. 1).

Surgical instrument (710) also includes an articulation control assembly (718) having articulation control knob (222) connected to a transmission assembly (726) for selectively directing longitudinal movement of elongated articulation bands (713, 715) and articulating articulation section (130) (see FIG. 2) as discussed above. Rather than drum (252), lead screws (254, 256), and other various components shown in FIG. 16, transmission assembly (726) shown in FIG. 31A has an articulation body (752) that is configured to translate between an upper position and a lower position along the transverse axis for flexing shaft assembly (712). As described herein, the upper position may also be referred to as the left position, and the lower position may also be referred to as the right position with respect to the direction of shaft articulation. These terms may thus be used interchangeably with respect to translating exemplary articulation body (752) along the transverse axis and are not intended to limit the invention described herein.

Figure 32A:
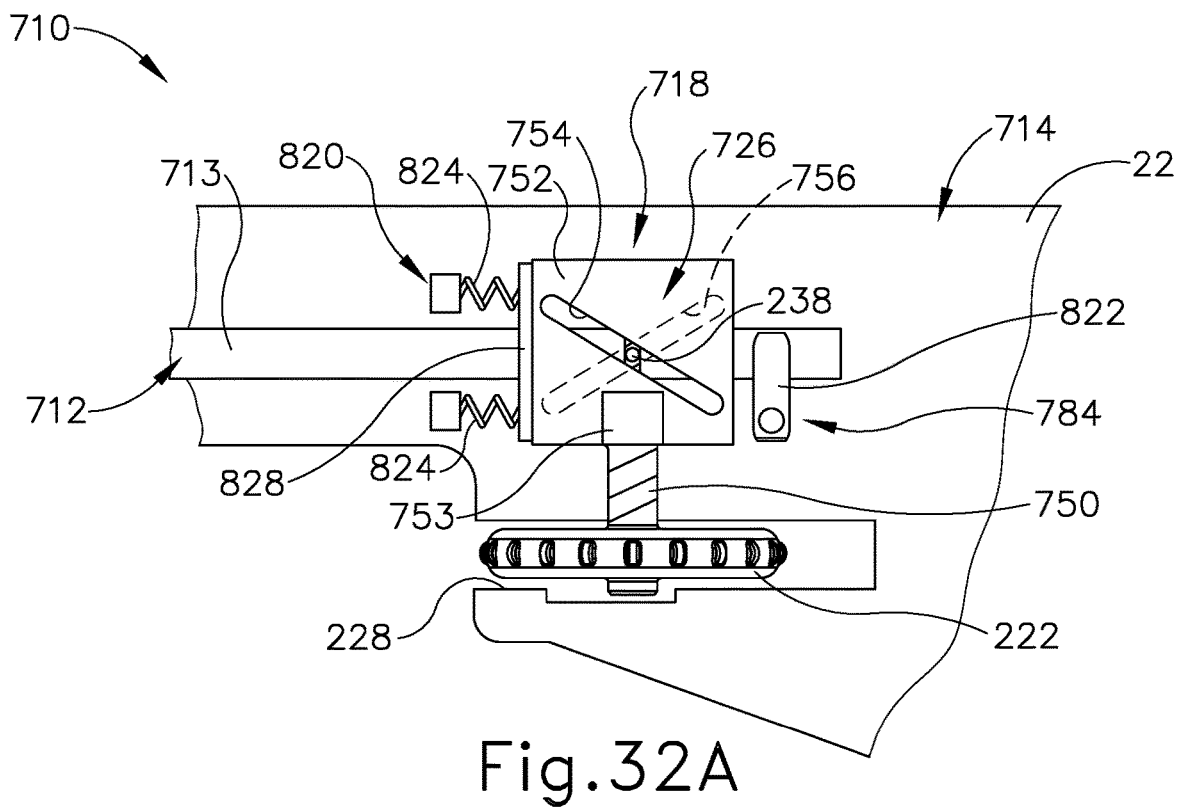
FIG. 32A depicts the side sectional view of the surgical instrument of FIG. 31A, with the shaft control assembly in a locked articulation position.

Articulation control knob (222) is rotatably mounted within knob slot (228) (see FIG. 21A) with a threaded drive shaft (750) rigidly extending upwardly into a threaded hole (753) in articulation body (752) (see FIG. 32A). Threaded drive shaft (750) and articulation body (762) are thus operatively connected such that clockwise rotation of articulation control knob (222) directs articulation body (752) toward the lower position and counterclockwise rotation of articulation control knob (222) directs articulation body (752) toward the upper position.

Articulation bands (713, 715) extend through articulation body (752), which is generally hollow in the present example. Opposing lateral walls of articulation body (752) each include a respective cam channel (754, 756). Pins (238, 240) are respectively received within cam channels (754, 756) and engage articulation bands (713, 715) to transmit longitudinal movement of pins (238, 240) to articulation bands (713, 715). To this end, each cam channel (754, 756) extends in the longitudinal direction and the transverse direction. However, cam channel (754) extends distally upwardly along the longitudinal direction, whereas cam channel (756) extends distally downwardly along the longitudinal direction. A central portion of each opposing cam channel (754, 756) is transversely and longitudinally aligned despite extending in opposite angles relative to the longitudinal axis. Thus, pins (238, 240) are directly opposed from one another in the straight configuration such that each articulation band (713, 715) is in the same longitudinal position. In use, translating articulation body (752) downwardly via articulation control knob (222) causes pin (238) and band (713) to move distally, while pin (240) and band (715) move proximally for the left configuration shown in FIG. 31B. In contrast, translating articulation body (752) upwardly via articulation control knob (222) causes pin (238) and band (713) to move proximally, while pin (240) and band (715) move distally for the right configuration.

Figure 32B:
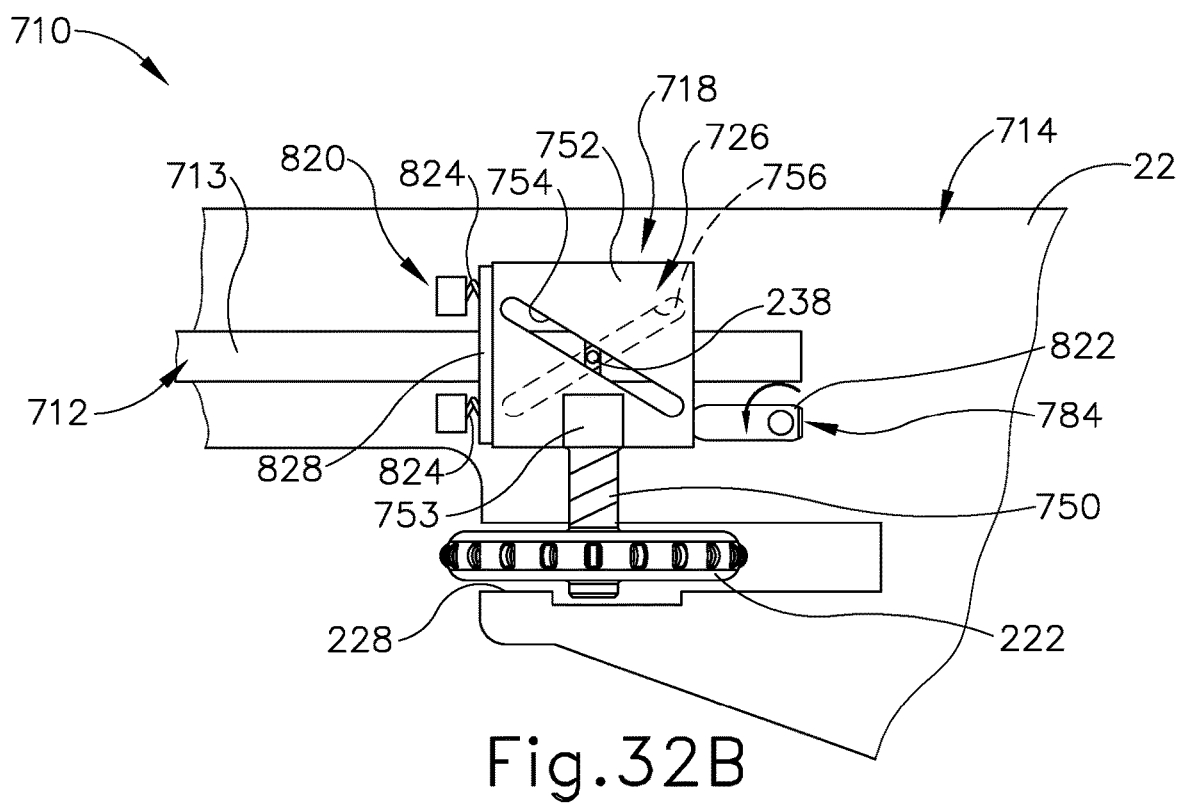
FIG. 32B depicts a side sectional view of the surgical instrument of FIG. 31A, with the shaft control assembly in an unlocked articulation position.

FIGS. 32A-32B also show surgical instrument (710) having articulation control assembly (718) with an articulation control lock (784) including a body tensioner (820) and a cooperative lock member in the form of a lock switch (822). As discussed briefly above, applying proximal tension to articulation bands (713, 715) locks and further rigidizes shaft assembly (712) regardless of shaft position, to inhibit movement at articulation section (130) (see FIG. 11). However, lock switch (822) is configured to unlock and release the tension to enable the operator to more easily articulate articulation section (130) (see FIG. 11) via articulation control knob (222).

In the present example, body tensioner (820) includes a pair of compression springs (824) connected to housing (22) via a pair of respective spring mounts (826). Springs (824) connect to articulation body (752) via a slider (828), which is configured to accommodate translational movement of articulation body (752) along the transverse axis. In a locked articulation state as shown in FIG. 32A, the springs (824) direct articulation body (752) and articulation control knob (222) to a proximal position. Tension is thereby applied to the articulation bands (713, 715) and articulation control knob (222) is at least partially hidden distally within housing (22) to inhibit the operator from accessing articulation control knob (222). Lock switch (822) is also pivoted to a relatively proximal position to allow springs (824) to proximally extend.

In use, and as shown in FIG. 32B, the operator desiring to articulate articulation section (130) (see FIG. 11) pivots lock switch (822) distally to a distal position. In turn, lock switch (822) urges articulation body (752) and articulation control knob (222) distally, thereby compressing springs (824) and releasing tension in articulation bands (713, 715) in the unlocked articulation state. Articulation control knob (222) also distally extends further from housing (22) for improved access and grip by the operator. The operator then selectively rotates articulation control knob (222) as discussed above. Furthermore, the relative position and access of articulation control knob (222) in the locked and unlocked articulation state serves as an indicator to the operator regarding the particular state selected at any given time for improved use.

Figure 33A:
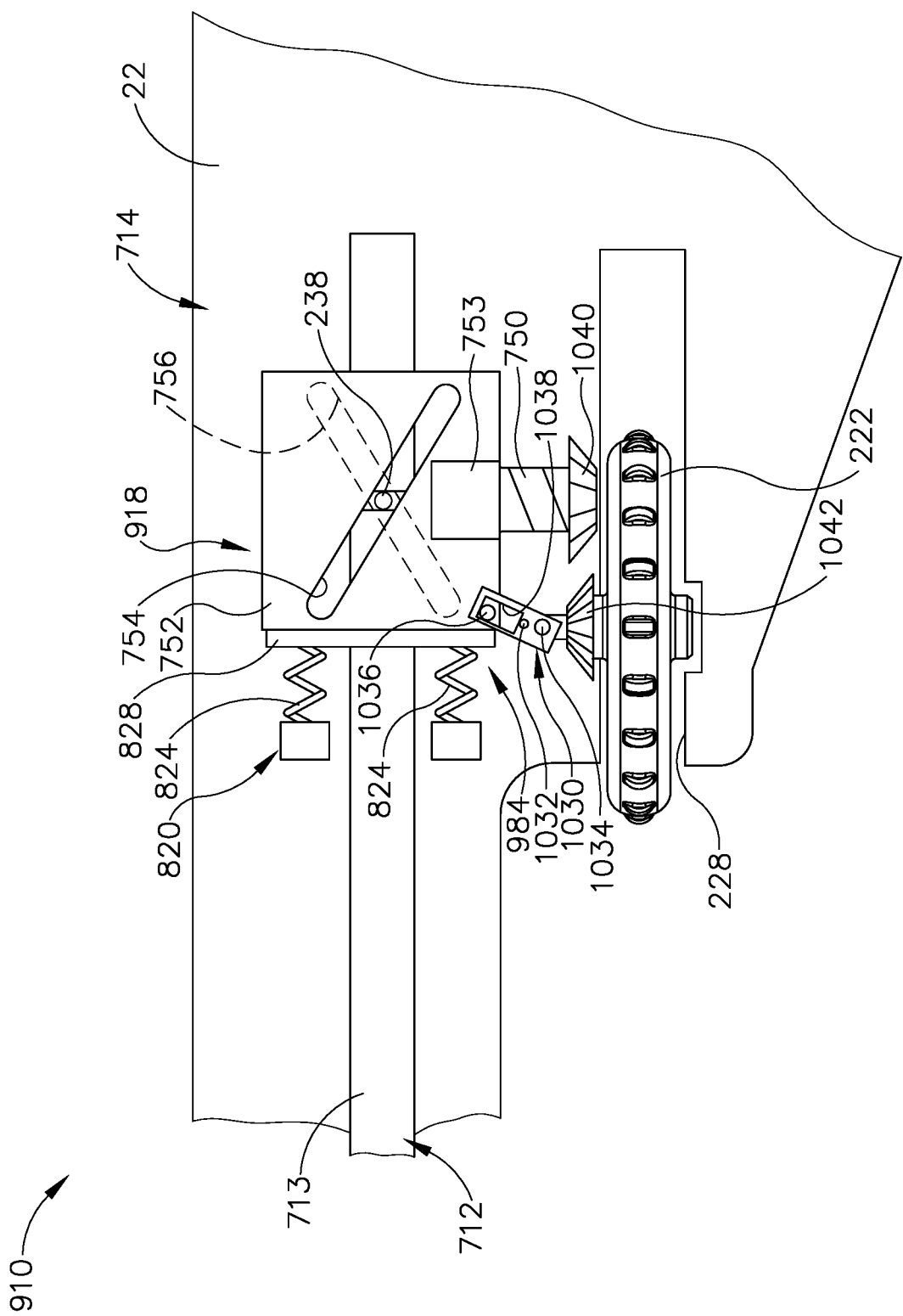
FIG. 33A depicts an enlarged side sectional view of a seventh exemplary ultrasonic surgical instrument with a shaft control assembly in a locked articulation position.
Figure 34A:
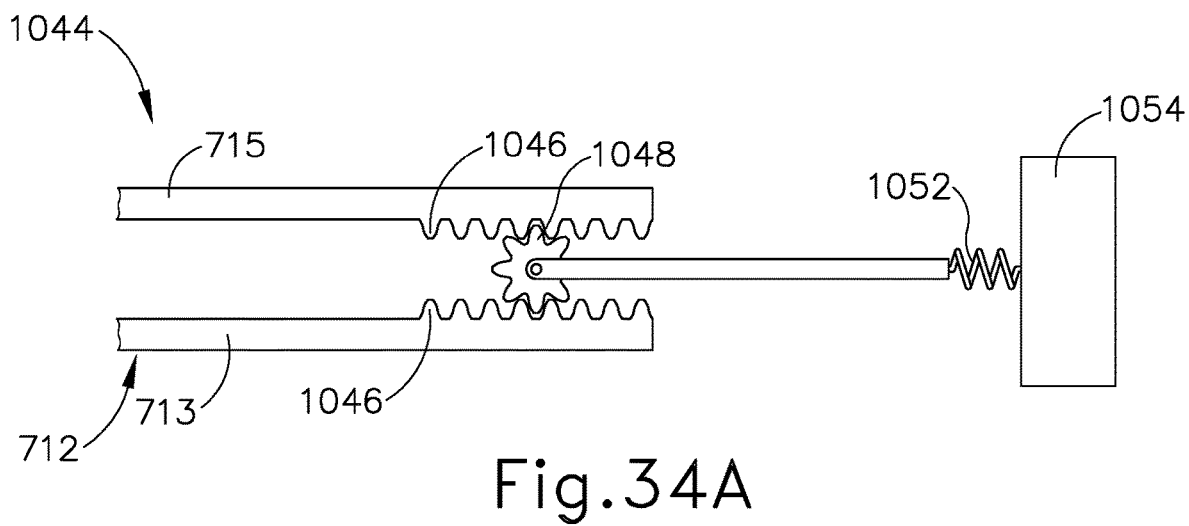
FIG. 34A depicts a top view of an exemplary articulation control lock in a straight configuration.
Figure 34B:
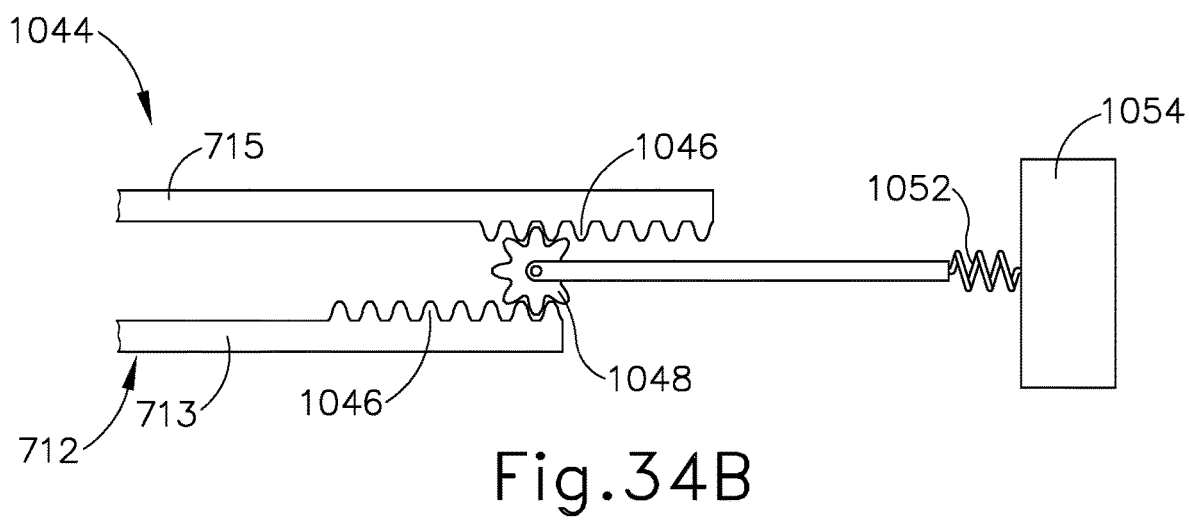
FIG. 34B depicts a top view of the articulation control lock of FIG. 34A, with the articulation control lock in a right configuration.
Figure 34C:
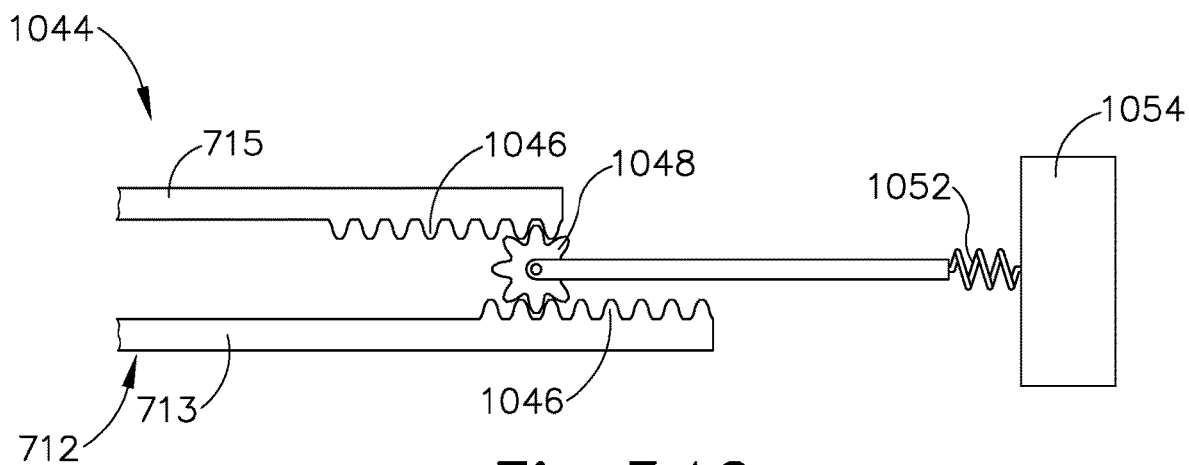
FIG. 34C depicts a top view of the articulation control lock of FIG. 34A, with the articulation control lock in a left configuration.

F. Exemplary Transmission Assembly with Translating Articulation Body Coupled with Articulation Control Knob via a Linkage for Variable Tension in Articulation Section FIGS. 33A-33B show a seventh exemplary ultrasonic surgical instrument (910) having handle assembly (714), shaft assembly (712), and an articulation control assembly (918). Like articulation control assembly (718) (see FIG. 32A) discussed above, articulation control assembly (918) has articulation control knob (222), threaded drive shaft (750), articulation body (752), and body tensioner (820) for locking articulation control assembly (918) in a locked articulated state. In addition, articulation control assembly (918) has an articulation control lock (984) with a linkage (1030) operatively connecting articulation control knob (222) and articulation body (752) such that articulation control knob (222) is selectively connected to drive shaft (750) rather than rigidly connected. In other words, in the locked articulation state (FIG. 33A), articulation control knob (222) effectively freewheels relative to drive shaft (750); but in the unlocked articulation state (FIG. 33B), articulation control knob (222) engages drive shaft (750) for shaft articulation as discussed above.

In the present example, linkage (1030) is rotatably connected to housing (22) and configured to rotate about pin (1032). Articulation control knob (222) includes a lower mount pin (1034) rotatably connected to linkage (1030), and articulation body (752) has an upper mount pin (1036) received within a linkage slot (1038). In the locked articulation state, springs (824) direct articulation body (752) proximally, which urges articulation control knob (222) distally from knob slot (228) via linkage (1030) for improved operator access.

As shown in FIG. 33B, the operator urges articulation control knob (222) proximally within knob slot (228) to unlock articulation control assembly (918) for articulation. Specifically, proximal movement induced at lower mount pin (1034) causes linkage to rotate and pull upper mount pin (1036) distally through linkage slot (1038). Articulation control knob (222) continues to move proximally until engaging drive shaft (750) in the unlocked articulation state. In the present example, a driven gear (1040) extends downwardly from drive shaft (750) and a drive gear (1042) extends upwardly from articulation control knob (222). Drive and driven gears (1040, 1042) are configured to engage to transfer rotation therealong in the unlocked articulation state; and to disengage in the locked articulation state such articulation control knob (222) freewheels. In addition, the distal protrusion of articulation control knob (222) from knob slot (228) as well as the tactile freewheel sensation are configured to indicate to the operator the particular state selected at any given time for improved use.

G. Exemplary Tension Coupling for Increasing Tension in Articulation Section

FIG. 31A and FIGS. 34A-34C show another exemplary articulation control lock (1044), which may be used alone or in combination with other alternative articulation control locks discussed herein. Articulation control lock (144) includes a pair of racks (1046) and a resiliently mounted and rotatable pinion (1048). Racks (1046) are presented by inwardly facing lateral surfaces of articulation bands (713, 715), with pinion (1048) sandwiched therebetween to engage with each rack (1046) simultaneously.

Pinion (1048) in the locked articulation state is pulled proximally via a biasing element, such as a tension spring (1052). In turn, pinion (1048) similarly pulls proximally on each articulation band (713, 715) to rigidize shaft assembly (712) and prevent inadvertent shaft deflection. In the present example, tension spring (1052) is proximally secured to a movable mount (1054) that is configured to be selectively moved toward pinion (1048) to reduce the tension until reaching the unlocked articulation state. In another example, pinion (1048) may be connected to a rotatable knob such as articulation control knob (222) for being selectively rotated to direct longitudinal movement of each articulation band (713, 715). In use, FIGS. 34A-34C respectively show articulation control assembly in a straight configuration, a right configuration, and a left configuration and may be selectively driven as discussed above.

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) a shaft assembly defining a longitudinal axis, wherein the shaft assembly includes: (i) a proximal end portion, (ii) a distal end portion configured to receive an end effector, and (iii) an articulation section configured to deflect the distal end portion from the longitudinal axis; (b) an articulation control assembly connected to the proximal end portion of the shaft assembly, wherein the articulation control assembly includes: (i) an articulation control member rotatably mounted relative to the shaft assembly, wherein the articulation control member is configured to be selectively manipulated by an operator, and (ii) a transmission assembly operatively connected between the articulation control member and the articulation section of the shaft assembly, wherein the transmission assembly is configured to transmit selective manipulation of the articulation control member to the articulation section and selectively actuate the articulation section, wherein the articulation control assembly is configured to lock without selective manipulation of the articulation control member to thereby inhibit actuation of the articulation section and unlock with selective manipulation of the articulation control member to thereby actuate the articulation section.

Example 2

The surgical instrument of Example 1, wherein the transmission assembly further includes: (A) a drive gear fixed to the articulation control member such that the articulation control member is rotatable to rotate the drive gear, and (B) a driven gear engaged with the drive gear, wherein the driven gear is operatively connected to the articulation section such that the driven gear is configured to transmit rotation of the drive gear to the remainder of the transmission assembly to selectively actuate the articulation section.

Example 3

The surgical instrument of Example 2, wherein the drive gear is in the form of a bevel drive gear, and wherein the driven gear is in the form of a bevel driven gear.

Example 4

The surgical instrument of Example 3, wherein the bevel drive gear is configured to rotate about an axis that is transverse to the longitudinal axis of the shaft assembly, and wherein the bevel driven gear is configured to rotate about the longitudinal axis of the shaft assembly.

Example 5

The surgical instrument of Example 4, wherein the transmission assembly further includes: (A) a drum configured to rotate about the longitudinal axis, wherein the drum includes a plurality of inner threads about the longitudinal axis, and (B) at least one lead screw engaged with the plurality of inner threads and configured to translate along the longitudinal axis upon rotation of the drum for actuating the articulation section, wherein the bevel driven gear is affixed to the drum such that the articulation control is rotatable to rotate the drum.

Example 6

The surgical instrument of Example 5, wherein the at least one lead screw is configured to lock without selective manipulation of the articulation control member to thereby inhibit actuation of the articulation section and unlock with selective manipulation of the articulation control member to thereby actuate the articulation section.

Example 7

The surgical instrument of any one or more of Examples 1 through 6, wherein the articulation control member is resiliently mounted relative to the transmission assembly and is configured to be manipulated from a locked articulation state to an unlocked articulation state to respectively lock and unlock the articulation control assembly, and wherein the articulation control member is biased toward the locked articulation state.

Example 8

The surgical instrument of Example 7, wherein the articulation control member is fixed to a drive gear via a drive shaft, and wherein the drive shaft is configured to resiliently deflect from the locked articulation state to the unlocked articulation state.

Example 9

The surgical instrument of any one or more of Examples 7 through 8, wherein the transmission assembly includes a drive gear, wherein the articulation control member is configured to translate from the locked articulation state to the unlocked articulation state, wherein the articulation control member is disengaged from the drive gear in the unlocked articulation state, and wherein the articulation control member is engaged with the drive gear in the unlocked articulation state.

Example 10

The surgical instrument of any one or more of Examples 7 through 9, further comprising, a handle assembly having at least one fixed tooth, wherein the articulation control member includes at least another fixed tooth, wherein the fixed teeth are engaged in the locked articulation state to inhibit the articulation control member from rotating relative to the handle assembly, and wherein the fixed teeth are disengaged in the unlocked articulation state to provide for rotating the articulation control member relative to the handle assembly.

Example 11

The surgical instrument of any one or more of Examples 1 through 10, wherein the transmission assembly further includes an articulation body, wherein the articulation body is resiliently mounted and configured to be moved from a locked articulation state to an unlocked articulation state to respectively lock and unlock the articulation control assembly, and wherein the articulation body is biased toward the locked articulation state.

Example 12

The surgical instrument of Example 11, wherein the articulation control member has a threaded drive shaft threadably received within the articulation body, and wherein the articulation body is configured to move along a transverse axis upon selective rotation of the articulation control member and the threaded drive shaft for actuating the articulation section.

Example 13

The surgical instrument of Example 12, wherein the transmission assembly further includes a lock member configured to selectively move between a first position and a second position, wherein the lock member in the first position allows the articulation body to be biased in the locked articulation state, and wherein the lock member in the second position urges the articulation body to the unlocked articulation state.

Example 14

The surgical instrument of any one or more of Examples 11 through 13, wherein the articulation control member is configured to be manipulated between a distal position and a proximal position, wherein the transmission assembly further comprises: (A) a drive gear fixed to the articulation control member, (B) a driven gear rotatably connected to the articulation body via a threaded drive shaft, wherein the articulation body is configured to move along a transverse axis upon selective rotation of the driven gear and the threaded drive shaft for actuating the articulation section, and (C) a linkage operatively coupling the articulation control member to the articulation body, wherein articulation control member is biased toward the distal position in the locked articulation state via the linkage, and wherein selectively urging the articulation control member to the proximal position is configured to direct the articulation body to the unlocked articulation state via the linkage, wherein the drive gear is disengaged from the driven gear with the articulation control member in the distal position, and wherein the drive gear is engaged with the driven gear with the articulation control member in the proximal position.

Example 15

The surgical instrument of any one or more of Examples 1 through 15, further comprising: (a) a handle assembly, wherein the shaft assembly extends distally from the handle assembly and is configured to rotate about the longitudinal axis relative to the handle assembly; and (b) a rotation control assembly connected to the shaft assembly, wherein the rotation control assembly includes: (i) a rotation control member connected to the shaft assembly and extending along the longitudinal axis, wherein the rotation control member is configured to be selectively rotated about the longitudinal axis and thereby rotate the shaft assembly about the longitudinal axis, and (ii) a rotation lock operatively connected to the shaft assembly and configured to selectively move between a locked rotation state and an unlocked rotation state, wherein the rotation lock is biased toward the locked rotation state and is configured to inhibit rotation of the shaft assembly relative to the handle assembly in the locked rotation state, and wherein the rotation lock in the unlocked rotation state allows rotation of the shaft assembly relative to the handle assembly via the rotation control member.

Example 16

A surgical instrument, comprising: (a) a handle assembly; (b) a shaft assembly defining a longitudinal axis and extending distally from the handle assembly, wherein the shaft assembly includes: (i) a proximal end portion, and (ii) a distal end portion configured to receive an end effector; and (c) a rotation control assembly connected to the shaft assembly, wherein the rotation control assembly includes: (i) a rotation control member connected to the shaft assembly and extending along the longitudinal axis, wherein the rotation control member is configured to be selectively rotated about the longitudinal axis and thereby rotate the shaft assembly about the longitudinal axis, and (ii) a rotation lock operatively connected to the shaft assembly and configured to selectively move between a locked rotation state and an unlocked rotation state, wherein the rotation lock is biased toward the locked rotation state and is configured to inhibit rotation of the shaft assembly relative to the handle assembly in the locked rotation state, and wherein the rotation lock in the unlocked rotation state allows rotation of the shaft assembly relative to the handle assembly via the rotation control member.

Example 17

The surgical instrument of Example 16, wherein the rotation lock further includes at least one button extending through the rotation control member and configured to be depressed toward the longitudinal axis to selectively direct the rotation control assembly from the locked rotation state to the unlocked rotation state.

Example 18

The surgical instrument of Example 17, wherein the at least one button includes a plurality of buttons extending through the rotation control member and arranged angularly about the longitudinal axis, and wherein each of the buttons is configured to be depressed toward the longitudinal axis to selectively direct the rotation control assembly from the locked rotation state to the unlocked rotation state.

Example 19

The surgical instrument of any one or more of Examples 17 through 18, wherein the rotation control assembly further includes an annular lock ring positioned about the longitudinal axis between the rotation control member and the shaft assembly, wherein the annular lock ring is biased toward the locked rotation state such that the annular lock ring engages each of the rotation control member and the handle assembly to inhibit rotation of the shaft assembly relative to the handle assembly, and wherein the at least one button is operable to urge the annular to disengage from at least one of the rotation control member and the handle assembly to allow rotation of the shaft assembly relative to the handle assembly via the rotation control member.

Example 20

A surgical instrument, comprising: (a) a shaft assembly defining a longitudinal axis, wherein the shaft assembly extends distally from the handle assembly and includes: (i) a proximal end portion, (ii) a distal end portion configured to receive an end effector, and (iii) an articulation section configured to deflect the distal end portion from the longitudinal axis; and (b) an articulation control assembly connected to the proximal end portion of the shaft assembly, wherein the articulation control assembly includes: (i) an articulation control member rotatably mounted relative to the shaft assembly, wherein the articulation control member is configured to be selectively manipulated by an operator, and (ii) a transmission assembly operatively connected between the articulation control member and the articulation section of the shaft assembly, wherein the transmission assembly is configured to transmit selective manipulation of the articulation control member to the articulation section and selectively actuate the articulation section, wherein the transmission assembly includes: (A) a bevel drive gear fixed to the articulation control member such that the articulation control member is rotatable to rotate the bevel drive gear, and (B) a bevel driven gear engaged with the bevel drive gear, wherein the bevel driven gear is operatively connected to the articulation section such that the bevel driven gear is configured to transmit rotation of the bevel drive gear to the remainder of the transmission assembly to selectively actuate the articulation section.

IV. MISCELLANEOUS

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Moreover, those of ordinary skill in the art will recognize that various teachings herein may be readily applied to electrosurgical instruments, stapling instruments, and other kinds of surgical instruments. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. A surgical instrument, comprising:
(a) a shaft assembly defining a longitudinal axis extending in a longitudinal direction, wherein the shaft assembly includes:
   (i) a proximal end portion,
   (ii) a distal end portion configured to receive an end effector, and
   (iii) an articulation section configured to deflect the distal end portion from the longitudinal axis;
(b) a handle assembly extending proximally from the shaft assembly, wherein the shaft assembly is selectively rotatable relative to the handle assembly about the longitudinal axis; and
(c) an articulation control assembly connected to the proximal end portion of the shaft assembly, wherein the articulation control assembly includes:
   (i) an articulation control member mounted to the handle assembly such that the articulation control member is configured to rotate about a first axis extending in a first direction, wherein the first axis is fixed relative to the handle assembly and the first direction is different than the longitudinal direction, wherein the articulation control member is configured to be selectively manipulated by an operator, and
   (ii) a transmission assembly operatively connected between the articulation control member and the articulation section of the shaft assembly, wherein the transmission assembly is configured to transmit selective manipulation of the articulation control member to the articulation section and selectively actuate the articulation section, wherein the transmission assembly includes a frame secured relative to the handle assembly and configured to support at least a portion of the transmission assembly thereon,
wherein the first axis is proximally positioned relative to the frame, and
wherein the articulation control assembly is configured to lock without selective manipulation of the articulation control member to thereby inhibit actuation of the articulation section and unlock with selective manipulation of the articulation control member to thereby actuate the articulation section,
wherein the transmission assembly further includes:
   (A) a drive gear fixed to the articulation control member such that the articulation control member is rotatable to rotate the drive gear, and
   (B) a driven gear engaged with the drive gear, wherein the driven gear is operatively connected to the articulation section such that the driven gear is configured to transmit rotation of the drive gear to the remainder of the transmission assembly to selectively actuate the articulation section,
wherein at least a portion of the frame is proximally positioned relative to the driven gear such that the first axis is proximally positioned relative to the at least the portion of the frame.

2. The surgical instrument of claim 1, wherein the drive gear is in the form of a bevel drive gear, and wherein the driven gear is in the form of a bevel driven gear.

3. The surgical instrument of claim 2, wherein the bevel drive gear is configured to rotate about the first axis that is transverse to the longitudinal axis of the shaft assembly, and wherein the bevel driven gear is configured to rotate about the longitudinal axis of the shaft assembly.

4. The surgical instrument of claim 3, wherein the transmission assembly further includes:
(A) a drum configured to rotate about the longitudinal axis, wherein the drum includes a plurality of inner threads about the longitudinal axis, and
(B) at least one lead screw engaged with the plurality of inner threads and configured to translate along the longitudinal axis upon rotation of the drum for actuating the articulation section,
wherein the bevel driven gear is affixed to the drum such that the articulation control member is rotatable to rotate the drum.

5. The surgical instrument of claim 4, wherein the at least one lead screw is configured to lock without selective manipulation of the articulation control member to thereby inhibit actuation of the articulation section and unlock with selective manipulation of the articulation control member to thereby actuate the articulation section.

6. The surgical instrument of claim 1, wherein the shaft assembly includes an end effector and the handle assembly includes a trigger, wherein the trigger is operatively connected to the end effector and configured to selectively manipulate at least a portion of the end effector, and wherein the articulation control member is offset from the longitudinal axis and positioned transversely between the trigger and the longitudinal axis.

7. The surgical instrument of claim 1, wherein the transmission assembly further includes:
(A) a drum configured to rotate about the longitudinal axis, wherein the drum includes a plurality of inner threads about the longitudinal axis, and
(B) at least one lead screw engaged with the plurality of inner threads and configured to translate along the longitudinal axis upon rotation of the drum for actuating the articulation section,
wherein the articulation control member is operatively connected to the drum such that the articulation control member is rotatable to rotate the drum.

8. The surgical instrument of claim 7, wherein the at least the portion of the transmission assembly includes the at least the one lead screw supported on the frame, wherein the frame is further configured to prevent rotation of the at least one lead screw.

9. The surgical instrument of claim 8, wherein the drive gear is spaced apart from the frame in a transverse direction relative to the longitudinal direction.

10. A surgical instrument, comprising:
(a) a shaft assembly defining a longitudinal axis, wherein the shaft assembly includes:
   (i) a proximal end portion having a knob configured to be selectively manipulated by an operator,
   (ii) a distal end portion configured to receive an end effector, and
   (iii) an articulation section configured to deflect the distal end portion from the longitudinal axis; and
(b) an articulation control assembly connected to the proximal end portion of the shaft assembly, wherein the articulation control assembly includes:
   (i) an articulation control member rotatably mounted about a first axis relative to the shaft assembly, wherein the articulation control member is configured to be selectively manipulated by the operator, and
   (ii) a transmission assembly operatively connected between the articulation control member and the articulation section of the shaft assembly, wherein the transmission assembly is configured to transmit selective manipulation of the articulation control member to the articulation section and selectively actuate the articulation section, wherein the transmission assembly further includes:
  (A) a drum positioned at least partially within the knob of the shaft assembly and configured to rotate about the longitudinal axis independent of the knob, wherein the drum includes a plurality of inner threads about the longitudinal axis,
  (B) at least one lead screw positioned within the knob, engaged with the plurality of inner threads, and configured to translate along the longitudinal axis upon rotation of the drum for actuating the articulation section, and
  (C) a frame configured to support the at least one lead screw thereon and prevent rotation of the at least one lead screw,
wherein the first axis is proximally positioned relative to the frame,
wherein the at least one lead screw is configured to lock relative to the drum without selective manipulation of the articulation control member to thereby inhibit actuation of the articulation section, and wherein the at least one lead screw is configured to unlock relative to the drum with selective manipulation of the articulation control member to thereby actuate the articulation section,
wherein at least a portion of the frame is proximally positioned relative to the drum such that the first axis is proximally positioned relative to the at least the portion of the frame.

* * * * *